US010278971B2

(12) United States Patent
Lee et al.

(10) Patent No.: US 10,278,971 B2
(45) Date of Patent: May 7, 2019

(54) FLUOROCYCLOPENTENYLCYTOSINE METHODS OF USE

(71) Applicant: Rexahn Pharmaceuticals, Inc., Rockville, MD (US)

(72) Inventors: Young Bok Lee, Clarksburg, MD (US); Deog Joong Kim, Rockville, MD (US); Godefridus J. Peters, Amsterdam (NL); Reza Mazhari, Rockville, MD (US); Dzjemma Sarkisjan, Amsterdam (NL)

(73) Assignee: REXAHN PHARMACEUTICALS, INC., Rockville, MD (US)

( * ) Notice: Subject to any disclaimer, the term of this patent is extended or adjusted under 35 U.S.C. 154(b) by 0 days.

(21) Appl. No.: 15/683,408

(22) Filed: Aug. 22, 2017

(65) Prior Publication Data
US 2018/0021338 A1 Jan. 25, 2018

Related U.S. Application Data

(62) Division of application No. 15/178,390, filed on Jun. 9, 2016, now Pat. No. 9,782,410.
(Continued)

(51) Int. Cl.
A61K 9/00 (2006.01)
A61K 9/20 (2006.01)
(Continued)

(52) U.S. Cl.
CPC .......... A61K 31/513 (2013.01); A61K 9/0053 (2013.01); A61K 9/20 (2013.01);
(Continued)

(58) Field of Classification Search
CPC .............. A61K 31/513; A61K 2300/00; A61K 2039/505; A61K 39/00; A61K 39/3955;
(Continued)

(56) References Cited

U.S. PATENT DOCUMENTS 4,369,174 A 1/1983 Nagai et al.
4,842,866 A 6/1989 Horder et al.
(Continued)

FOREIGN PATENT DOCUMENTS

WO WO-2005/097757 A2 10/2005

OTHER PUBLICATIONS

Baas et al., "Concurrent chemotherapy (carboplatin, paclitaxel, etoposide) and involved-field radiotherapy in limited stage small cell lung cancer: a Dutch multicenter phase II study." Br J Cancer 94: 625-30, 2006.
(Continued)

Primary Examiner — Savitha M Rao
(74) Attorney, Agent, or Firm — Keith G. Haddaway; Annette K. Kwok; Venable LLP

(57) ABSTRACT

The disclosed subject matter provides methods using and kits comprising a compound of formula (I)

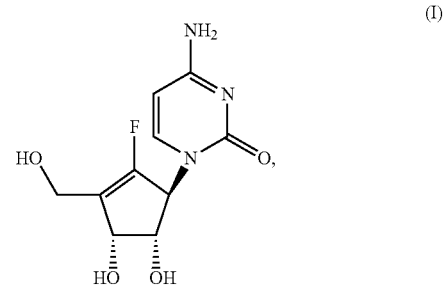

or a hydrate, a solvate, or a pharmaceutically acceptable salt thereof. The disclosed subject matter further provides a method of treating one or more symptoms of cancer comprising administering to a subject in need thereof a compound of formula (I) and a process for preparing such.

17 Claims, 37 Drawing Sheets

Related U.S. Application Data

(60) Provisional application No. 62/173,174, filed on Jun. 9, 2015, provisional application No. 62/210,708, filed on Aug. 27, 2015, provisional application No. 62/289,801, filed on Feb. 1, 2016, provisional application No. 62/319,369, filed on Apr. 7, 2016.

(51) Int. Cl.
 A61K 9/48 (2006.01)
 A61K 39/00 (2006.01)
 A61K 45/06 (2006.01)
 C07K 16/28 (2006.01)
 A61K 31/513 (2006.01)
 A61K 39/395 (2006.01)
 C07D 239/47 (2006.01)
 G01N 33/574 (2006.01)

(52) U.S. Cl.
 CPC .......... A61K 9/48 (2013.01); A61K 39/00 (2013.01); A61K 39/3955 (2013.01); A61K 45/06 (2013.01); C07D 239/47 (2013.01); C07K 16/2818 (2013.01); C07K 16/2827 (2013.01); C12Y 207/01048 (2013.01); G01N 33/57496 (2013.01); A61K 9/2004 (2013.01); A61K 9/4841 (2013.01); A61K 2039/505 (2013.01); C07K 2317/76 (2013.01); G01N 2333/91215 (2013.01); G01N 2800/52 (2013.01)

(58) Field of Classification Search
 CPC ........ A61K 45/06; A61K 9/0053; A61K 9/20; A61K 9/48; C07D 239/47; C07K 16/2818; C07K 16/2827; C07K 2317/76; C12Y 207/01048; G01N 2333/91215; G01N 33/57496
 See application file for complete search history.

(56) References Cited

U.S. PATENT DOCUMENTS

| | | | |
|---|---|---|---|
| 5,217,720 | A | 6/1993 | Sekigawa et al. |
| 6,569,457 | B2 | 5/2003 | Ullah et al. |
| 6,638,534 | B1 | 10/2003 | Ishibashi et al. |
| 7,405,214 | B2 | 7/2008 | Lee et al. |
| 9,150,520 | B2 | 10/2015 | Yin et al. |
| 2014/0275537 | A1 | 9/2014 | Yin et al. |
| 2015/0210769 | A1 | 7/2015 | Freeman |

OTHER PUBLICATIONS

Bijnsdorp et al., "Radiosensitizing potential of the selective cyclooygenase-2 (COX-2) inhibitor meloxicam on human glioma cells." *J Neurooncol* 85: 25-31, 2007.
Choi et al., "Fluorocyclopentenyl-cytosine with Broad Spectrum and Potent Antitumor Activity +," Journal of Medicinal Chemistry, vol. 55, No. 9, May 10, 2012, pp. 4521-4525.
El-Nagger, et al., "Radiosensitization by thymidine phosphorylase inhibitor in thymidine phosphorylase negative and overexpressing bladder cancer cell lines." *Nucleosides Nucleotides Nucleic Acids* 33: 413-21, 2014.
Galvani et al., "Molecular mechanisms underlying the antitumor activity of 3-aminopropanamide irreversible inhibitors of the epidermal growth factor receptor in non-small cell lung cancer." *Neoplasia* 15: 61-72, 2013.
Glover et al., "Biochemistry of azacitidine: a review." *Cancer Treat Rep* 71: 959-64, 1987.
Gonen N., et al., "PCTF/SLC46A1 promoter methylation and restoration of gene expression in human leukemia cells", BBRC 376, 787-92, 2008.
Hwang et al., "Radiosensitivity of thymidylate synthase-deficient human tumor cells is affected by progression through the G1 restriction point into S-phase: implications for fluoropyrimidine radiosensitization." *Cancer Res* 60: 92-100, 2000.
Ingraham et al., "Nucleotide levels and incorporation of 5-fluorouracil and uracil into DNA of cells treated with 5-fluorodeoxyuridine." *Mol Pharmacol* 21: 211-6, 1982.
Jansen G., et al., "A Structurally Altered Human Reduced Folate Carrier with Increased Folic Acid Transport Mediates a Novel Mechanism of Antifolate Resistance", JBC 273, 30189-30198, 1998.
Jones, "Effects of 5-azacytidine and its 2'-deoxyderivative on cell differentiation and DNA methylation." *Pharmacol Ther* 28: 17-27, 1985.
Kaminskas, et al. "Approval summary: azacitidine for treatment of myelodysplastic syndrome subtypes." *Clin Cancer Res* 11: 3604-8, 2005.
Keiser et al., Correlation of Multidrug Resistance with Decreased Drug Accumulation, Altered Subcellular Drug Distribution, and Increased P-Glycoprotein Expression on Cultured SW-1573 Human Lung Tumor Cells, *Cancer Research*, 49:2988-2993 (1989).
Lawrence et al., "The mechanism of action of radiosensitization of conventional chemotherapeutic agents." *Semin Radial Oncol* 13: 13-21, 2003.
Lemos et al., "Impact of cellular folate status and epidermal growth factor receptor expression on BCRP/ABCG2-mediated resistance to gefitinib and erlotinib," British Journal of Cancer vol. 100, pp. 1120-1127 (2009).
Morgan et al., "Improving gemcitabine-mediated radiosensitization using molecularly targeted therapy: A review," Clin. Cancer Res. 14(21): 6744-6750 (2008).
Peters et al., "Fluorocyclopentenylcytosine (RX-3117) is activated by uridine-cytidine kinase 2, a potential biomarker," Presented at the American Association for Cancer Research (AACR) 106th Annual Meeting, Philadelphia, Pennsylvania, Apr. 18-22, 2015.
Peters et al., "Metabolism, mechanism of action and sensitivity profile of fluorocyclopentenylcytosine (RX-3117)," Invest New Drugs, Dec. 2013, vol. 31, No. 6, pp. 1444-1457.
Peters, et al., "Inhibition of DNA Methyltransferase by RX-3117 Leads to Upregulation of Hypomethylated Targets," Presented at American Association for Cancer Research (AACR) 107th Annual Meeting, Apr. 16-20, 2016.
Peters, et al., "Novel developments in the use of antimetabolites." *Nucleosides Nucleotides Nucleic Acids* 33: 358-74, 2014.
Rasco et al., A Phase 1 Study of RX-3117 an Oral Agent Activated by Uridine Cytidine Kinase 2 to Treat Subjects with Advanced Solid Tumors 2015 (Poster).
Rasco, et al., "Preliminary phase 1 data of single agent RX-3117, an oral antimetabolite nucleoside," Presented at the 2015 The European Cancer Congress (ECC 2015) Annual Meeting, Vienna, Austria, Sep. 25-29, 2015.
Sarkisjan et al., "The Cytidine analog fluorocyclopentenylcytosine (RX-3117) is activated by uridine-cytidine kinase 2," pp. 1-23, Sep. 9, 2016.
Sarkisjan et al., "The radiosensitizing effect of fluorocyclopentenyl-cytosine (RX-3117) in ovarian and lung cancer cell lines," pp. 0-23, 2016.
Sarkisjan et al., Concentration and cell line dependent effects of fluorocyclopentenylcytosine (RX-3117) in non-small cell lung cancer cells (Poster) Jun. 9, 2015.
Shewach et al., "Antimetabolite radiosensitizers." *J Clin Oncol* 25: 4043-50, 2007.
Simon et al., "Accellerated Titration Designs for Phase I Clinical Trials in Oncology," J. Nat. Can. Inst., vol. 89, No. 15, pp. 1138-1147 (1997).
Sripayap et al., "Mechanisms of resistance to azacitidine in human leukemia cell lines," Exp. Hematol 42: 294-306.e2, 2014.
Udvaros et al., "A phase 1 exploratory study of RX-3117 to determine oral bioavailability in cancer subjects with solid tumors," Journal of Clinical Oncology, vol. 33, No. 15 (suppl), pp. e13545, May 20, 2015.
Vesely, "Mode of action and effects of 5-azacytidine and of its derivatives in eukaryotic cells," Pharmacol. Ther. 28: 227-35, 1985.

(56) References Cited

OTHER PUBLICATIONS

Yang et al., "A novel small molecule cytidine analog, RX-3117, shows potent efficacy in xenograft models, even in tumors that are resistant to gemcitabine." (Poster) (*Presented at the AACR Annual Meeting*, San Diego, CA, Apr. 4-9, 2014.
Results of a Phase 1 Study of Single Agent RX-3117: An Oral Antimetabolite Nucleoside to Treat Solid Tumors, (Poster) 2015 (Presented at the 2016 American Society of Clinical Oncology (ASCO) Annual Meeting, Chicago, IL, Jun. 3-7, 2016).
FDA guidelines for animal to human dosage conversion, Pharmacology and toxicology, pp. 1-30, Jul. 2005.
Yang et al., (Anticancer Research), (34) pp. 6951-6960, 2014.

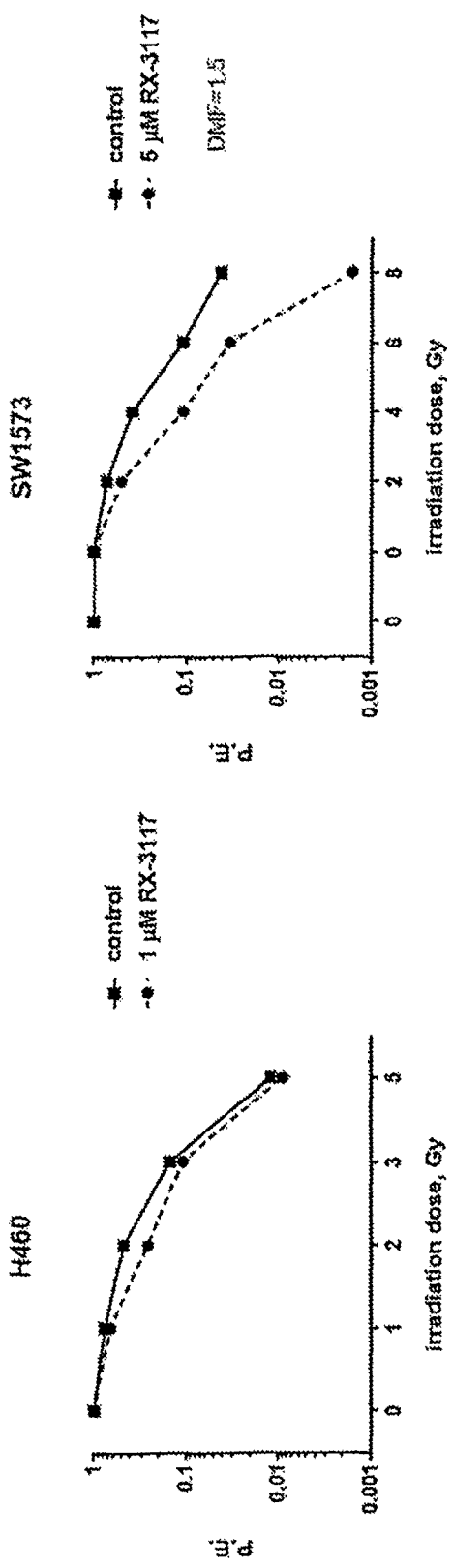

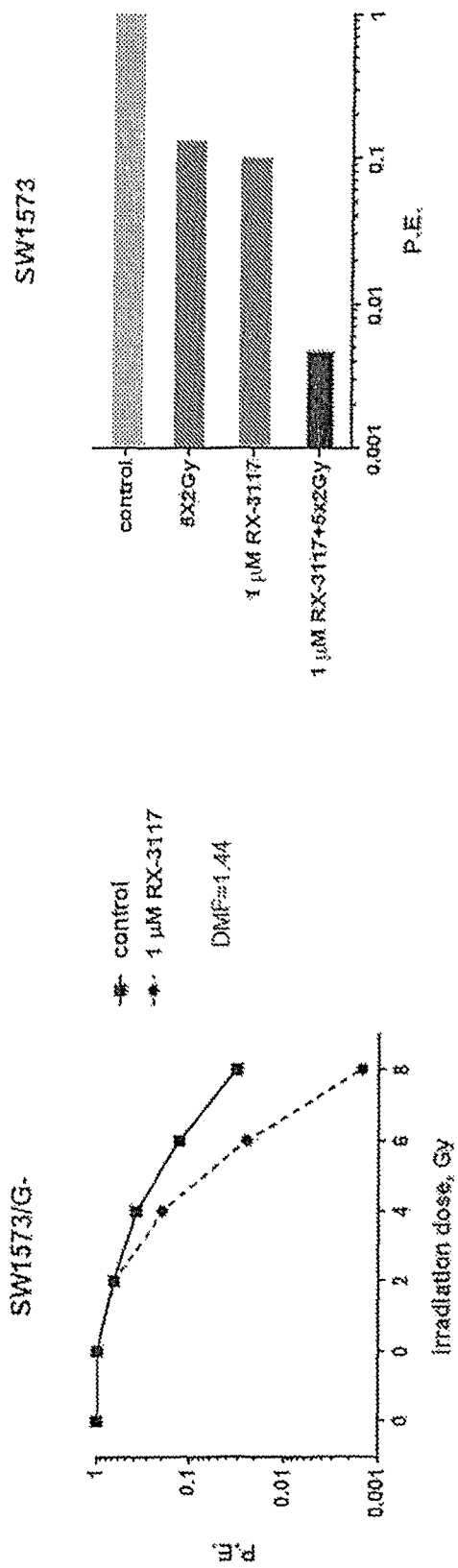

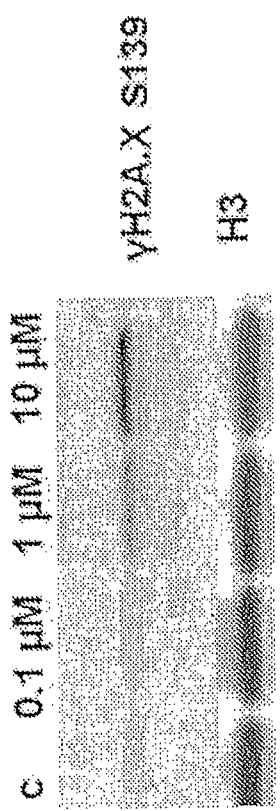
FIG. 18A
FIG. 18B

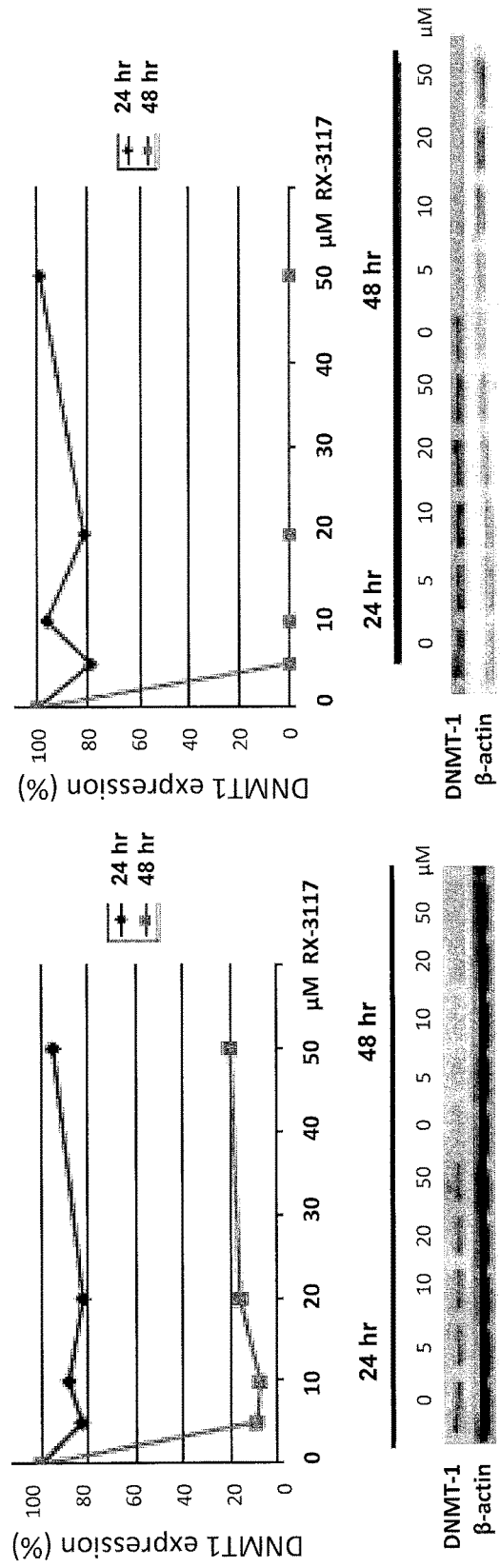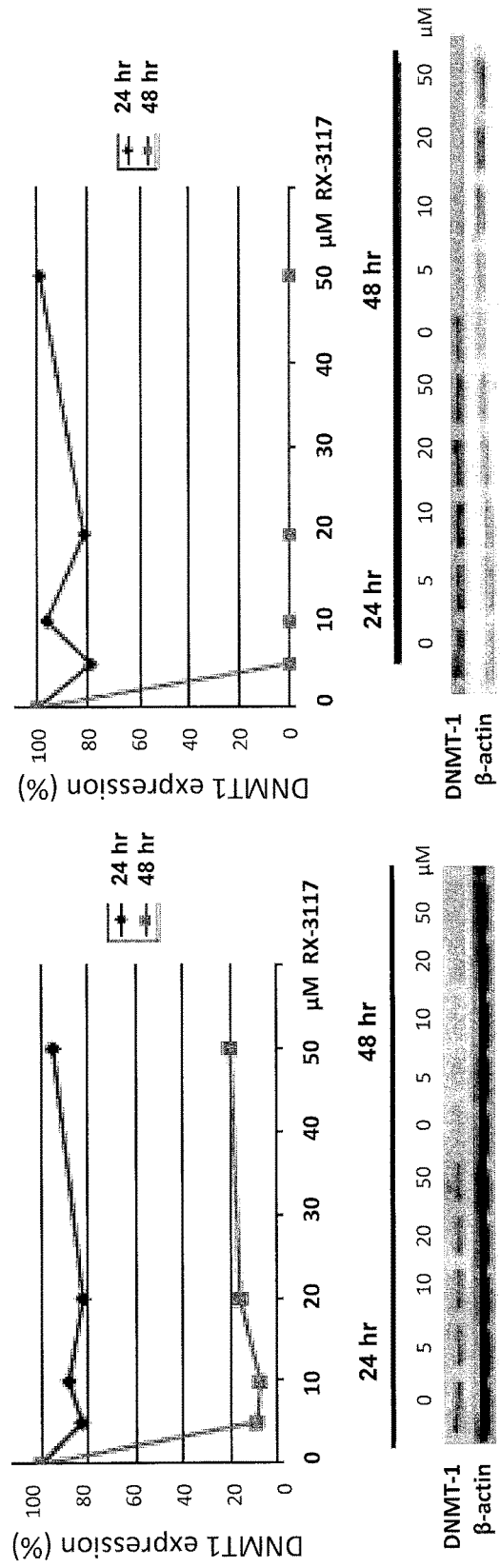
FIG. 25B
FIG. 25A

| pH (SN) | MTX uptake (pmol/min/1*10⁷ cells) | |
|---|---|---|
| | CEM | CEM/MTX |
| pH 5.5 | 1.11 ± 0.14 | 0.49 ± 0.13 |
| pH 5.5 + 1mM FA | 0.66 ± 0.11 | 0.51 ± 0.21 |
| pH 7.4 | 2.8 ± 0.52 | 0.03 ± 0.02 |
| pH 7.4 + 1mM LV | 0.046 ± 0.01 | 0.01 ± 0.01 |

FIG. 28A

FLUOROCYCLOPENTENYLCYTOSINE METHODS OF USE

PRIORITY

This application is a divisional of U.S. patent application Ser. No. 15/178,390, filed Jun. 9, 2016; claims priority to U.S. Provisional Application No. 62/173,174, filed Jun. 9, 2015; U.S. Provisional Application No. 62/210,708, filed Aug. 27, 2015; U.S. Provisional Application No. 62/289,801, filed Feb. 1, 2016; and U.S. Provisional Application No. 62/319,369 filed Apr. 7, 2016, the contents of which are hereby incorporated by reference in the entirety.

BACKGROUND OF THE INVENTION

U.S. Pat. No. 7,405,214 (issued Jul. 29, 2008) discloses a compound of formula (I)

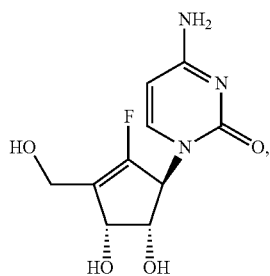

also referred to as RX-3117, fluorocyclopentenylcytosine or 4-amino-1-((1S,4R,5S)-2-fluoro-4,5-dihydroxy-3-hydroxymethyl-cyclopent-2-enyl)-1H-pyrimidin-2-one. U.S. Pat. No. 7,405,214 also discloses an 11-steps total synthesis of RX-3117 from D-ribose and the synthesis uses an expensive catalyst which poses a challenge for implementation in plant production.

U.S. Pat. No. 9,150,520 (issued Oct. 6, 2015) discloses a short route for the preparation of RX-3117 through (3R,4R,6aR)-tert-butyl-(5-fluoro-2,2-dimethyl-6-trityloxymethyl-4,6a-dihy-dro-3aH-cyclopenta[1,3]dioxol-4-yloxy)-diphenylsilane to 4-amino-1-(3aS,4S,6aR)-5-fluoro-2,2-dimethyl-6-((trityloxy)methyl)-4,6a-d-ihydro-3aH-cyclopenta[d][1,3]dioxol-4-yl)pyrimidin-2(1H)-one. The synthesis requires the intermediates to be isolated in each step. Thus, the process is unsatisfactory for scaled up production of the final product due to time and cost constraints. Therefore, there is a need to provide an improved process, for example by reducing the number of steps and/or removing the need to purify each intermediate.

SUMMARY OF THE INVENTION

The present invention is directed to new uses and methods of using the compound of formula (I). The present invention also provides an improved process to significantly reduce the cost of manufacturing by, among other things, combining multiple steps without isolation and purification of the intermediate materials. In addition, the present invention provides dosage and exposure levels for using the compound of formula (I) in a subject.

One aspect of the disclosure provides a method of treating a tumor by administering to a subject in need thereof an oral dosage form having an effective amount of a compound of formula (I)

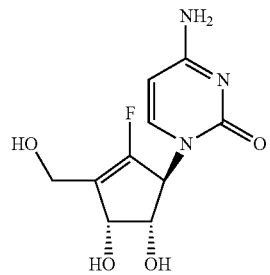

or a hydrate, a solvate or a pharmaceutically acceptable salt thereof, at a dosage of about 300-2,000 mg/day.

In embodiments, the compound of formula (I) is administrated as a monohydrate. In other embodiments, the compound of formula (I) is administrated free of solvates, hydrates and salts.

Embodiments of the method can include administering an oral dosage 5 to 7 days per week. Embodiments of the method can include administering an oral dosage 5 to 7 days per week for 4 consecutive weeks or for 3 consecutive weeks followed by 1 off-week during which the oral dosage form is not administered.

Embodiments of the method can include a dosing cycle consists of either 3 consecutive weeks of treatment followed by 1 off week, or 4 consecutive weeks of treatment, and the oral dosage form is administered for up to 12 dosing cycles.

Embodiments of the method can include an oral dosage form that provides a $C_{max}$ of about 700-1,100 ng/mL after a single administration. Embodiments of the method can include an oral dosage form that provides an $AUC_{0-t}$ (0-24 hours) of about 8,000-10,000 hr·ng/mL after a single administration.

Embodiments of the method can be used to treat tumors, including treating pancreatic, bladder or colorectal cancer.

Embodiments of the method can include administering the oral dosage form with a second agent or anti-tumor agent selected from the group consisting of antimetabolites, DNA-fragmenting agents, DNA-crosslinking agents, intercalating agents, protein synthesis inhibitors, topoisomerase I poisons, topoisomerase II poisons, microtubule-directed agents, kinase inhibitors, polyphenols, hormones, hormone antagonists, death receptor agonists, immune checkpoint inhibitors, anti-programmed cell death 1 (PD-1) receptor antibodies and anti-programmed cell death ligand 1 (PD-L1) antibodies. Embodiments of the method can include administering a PD-L1 antibody to the subject. Embodiments of the method can include administering PD-1 antibody to the subject. Embodiments of the method can include administering a solid oral dosage form. The second agent or anti-tumor agent can be administered in the same oral dosage form or in a separate oral dosage form.

In embodiments, the subject in need thereof is a human subject.

Another aspect of the disclosure provides a method of predicting efficacy of treatment of a subject in need thereof with a compound of formula (I)

(I)

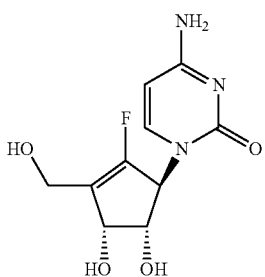

or a hydrate, a solvate, or a pharmaceutically acceptable salt thereof, including the steps of: (i) collecting a sample of tumor cell or tissue from the subject; and (ii) measuring the level of UCK2 expression in the tumor cell or tissue; wherein the expression level of UCK2 indicates a likelihood of efficacy of treatment with a compound of formula (I).

Another aspect of the disclosure is a kit for testing potential efficacy of a compound of formula (I) or a hydrate, a solvate, or a pharmaceutically acceptable salt in the treatment of tumor, by use of an assay that measures levels of kinases, p53, or UCK2 protein in a tumor cell sample.

Another aspect of the disclosure provides a method of treating one or more symptoms by administering to a subject in need thereof a compound of formula (I)

(I)

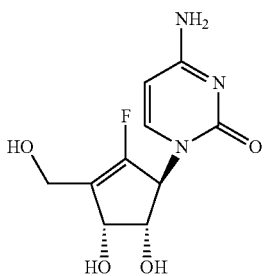

at an amount effective to inhibit methyltransferase and to upregulate at least one hypomethylated target in the subject. In embodiments, the compound of formula (I) is administrated as a monohydrate. In other embodiments, the compound of formula (I) is administrated free of solvates, hydrates and salts.

Another aspect of the disclosure provides a for preparing of 4-amino-1-((1S,4R,5S)-2-fluoro-4,5-dihydroxy-3-(hydroxymethyl)cyclopent-2-en-1-yl)pyrimidin-2(1H)-one 1H$_2$O (RX-3117-MH), by converting tert-butyl(((3aR,4R,6aR)-5-fluoro-2,2-dimethyl-6-((trityloxy)methyl)-4,6a-dihydro-3aH-cyclopenta[d][1,3]dioxol-4-yl)oxy)diphenylsilane (ASM11) to 4-amino-1-((3aS,4S,6aR)-5-fluoro-2,2-dimethyl-6-((trityloxy)methyl)-4,6a-dihydro-3aH-cyclopenta[d][1,3]dioxol-4-yl)pyrimidin-2(1H)-one (INT14) in a continuous process with more than one step without isolation of any intermediate.

Embodiments of the method can include dissolving tert-butyl(((3aR,4R,6aR)-5-fluoro-2,2-dimethyl-6-((trityloxy)methyl)-4,6a-dihydro-3aH-cyclopenta[d][1,3]dioxol-4-yl)oxy)diphenylsilane (ASM11) in 2-methyl tetrahydrofuran; adding tetra-n-butylammonium fluoride to form ((3aS,4R,6aR)-5-fluoro-2,2-dimethyl-6-((trityloxy)methyl)-4,6a-dihydro-3aH-cyclopenta[d][1,3]dioxol-4-ol) (INT12) in a reaction solution; and recovering INT12 in an organic phase.

Embodiments of the recovering INT12 in the organic phase can include washing the reaction solution with an aqueous solution; separating an aqueous extraction from the organic phase having INT12; washing the aqueous extraction with 2-methyl tetrahydrofuran to extract INT12 from the aqueous extraction; and combining the extracted INT12 with the organic phase having INT12.

Embodiments of the method can include adding triethylamine and methanesulphonyl chloride in 2-methyl tetrahydrofuran to the INT12 in the organic phase to form ((3aR,4R,6aR)-5-fluoro-2,2-dimethyl-6-((trityloxy)methyl)-4,6a-dihydro-3aH-cyclopenta[d][1,3]dioxol-4-yl methanesulfonate) (INT13) in a second reaction solution; and recovering INT13 in DMSO.

Embodiments of the recovering INT13 in DMSO can include adding the DMSO to the second reaction solution with INT13; and removing at least 90% w/w of 2-methyl tetrahydrofuran by distillation.

Embodiments of the method can include adding 2.5 equivalents of cesium carbonate and cytosine to the INT13 in DMSO to form 4-amino-1-((3aS,4S,6aR)-5-fluoro-2,2-dimethyl-6-((trityloxy)methyl)-4,6a-dihydro-3aH-cyclopenta[d][1,3]dioxol-4-yl)pyrimidin-2(1H)-one (INT14) in a third reaction solution.

Embodiments of the method can include maintaining reaction temperature at about 33 to 37° C.

In embodiments, the INT14 has a ratio of N- to O-isomers of over about 95:5.

Embodiments of the method can include adding an acid to the third reaction solution with INT14 to form 4-amino-1-((1S,4R,5S)-2-fluoro-4,5-dihydroxy-3-(hydroxymethyl)cyclopent-2-en-1-yl)pyrimidin-2(1H)-one (RX-3117); washing the RX-3117 with methyl tert-butyl ether and water to form an organic phase and an aqueous phase having RX-3117; and purifying the RX-3117 to form RX-3117-MH.

Embodiments of the method can include charging the reaction mixture with methanol and distilling the reaction mixture to remove acetonide until less than about 1.0% area of the acetonide is detected prior to the washing step.

Embodiments of the washing step can include separating the aqueous phase having RX-3117 from the organic phase; washing the aqueous phase having RX-3117 with methyl tert-butyl ether until less than about 0.5% w/w of trityl alcohol is detected in the aqueous phase; adding a basic anion resin to the aqueous phase having RX-3117 to form a slurry; filtering the slurry to retain a mother liquor; concentrating the mother liquor to form a concentrate; and adding acetonitrile to the concentrate to form purified RX-3117-MH.

Another aspect of the disclosure provides a continuous process for preparing 4-amino-1-((3aS,4S,6aR)-5-fluoro-2,2-dimethyl-6-((trityloxy)methyl)-4,6a-dihydro-3aH-cyclopenta[d][1,3]dioxol-4-yl)pyrimidin-2(1H)-one (INT14) from tert-butyl(((3aR,4R,6aR)-5-fluoro-2,2-dimethyl-6-((trityloxy)methyl)-4,6a-dihydro-3aH-cyclopenta[d][1,3]dioxol-4-yl)oxy)diphenylsilane (ASM11), including the steps of: dissolving the ASM11 in 2-methyl tetrahydrofuran; adding tetra-n-butylammonium fluoride to form ((3aS,4R,6aR)-5-fluoro-2,2-dimethyl-6-((trityloxy)methyl)-4,6a-dihydro-3aH-cyclopenta[d][1,3]dioxol-4-ol) (INT12); adding trimethylamine and methanesulphonyl chloride in 2-methyl tetrahydrofuran to the INT12 to form ((3aR,4R,6aR)-5-fluoro-2,2-dimethyl-6-((trityloxy)methyl)-4,6a-dihydro-3aH-cyclopenta[d][1,3]dioxol-4-yl methanesulfonate) (INT13); and adding cesium carbonate and cytosine to the INT13 to form 4-amino-1-((3aS,4S,6aR)-5-fluoro-2,2-dimethyl-6-((trityloxy)methyl)-4,6a-dihydro-3aH-cyclopenta

[d][1,3]dioxol-4-yl)pyrimidin-2(1H)-one (INT14); wherein the steps are performed in one or more fixed reactors without isolation of INT12 or INT13.

Another aspect of the disclosure provides a continuous process for preparing 4-amino-1-((1S,4R,5S)-2-fluoro-4,5-dihydroxy-3-(hydroxymethyl)cyclopent-2-en-1-yl)pyrimidin-2(1H)-one 1H$_2$O (RX-3117-MH) from 4-amino-1-((3aS,4S,6aR)-5-fluoro-2,2-dimethyl-6-((trityloxy)methyl)-4,6a-dihydro-3aH-cyclopenta[d][1,3]dioxol-4-yl)pyrimidin-2(1H)-one (INT14), including the steps of: reacting the INT14 with an acid to form 4-amino-1-((1S,4R,5S)-2-fluoro-4,5-dihydroxy-3-(hydroxymethyl)cyclopent-2-en-1-yl)pyrimidin-2(1H)-one (RX-3117); washing the RX-3117 with methyl tert-butyl ether and water to form an organic phase and an aqueous phase having RX-3117; separating the aqueous phase having RX-3117 from the organic phase; washing the aqueous phase having RX-3117 with methyl tert-butyl ether until less than about 0.5% w/w trityl alcohol is detected in the aqueous phase; adding a strongly basic anion resin to the aqueous phase having RX-3117 to form a slurry; filtering the slurry to retain a mother liquor; concentrating the mother liquor to form a concentrate; adding acetonitrile to the concentrate to form purified RX-3117-MH; and isolating the purified RX-3117-MH; wherein the steps are performed in one or more fixed reactors.

Another aspect of the disclosure provides a method of inducing apoptosis in a cell by contacting the cell with an effective amount of a compound of formula (I)

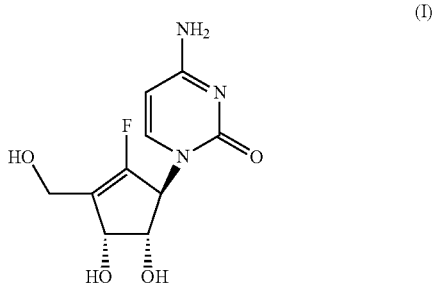 [SMILES: Nc1ccn([C@@H]2C(F)=C(CO)[C@@H](O)[C@H]2O)c(=O)n1]

(I)

or a hydrate, a solvate, or a pharmaceutically acceptable salt thereof.

Another aspect of the disclosure provides a method of sensitizing a cell to an apoptotic signal by contacting the cell with an effective amount of a compound of formula (I)

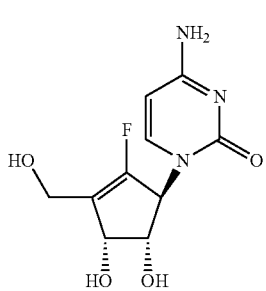

(I)

or a hydrate, a solvate, or a pharmaceutically acceptable salt thereof.

Another aspect of the disclosure provides a method of modulating protein kinase in a cell by contacting the cell with an effective amount of a compound of formula (I) or a hydrate, a solvate, or a pharmaceutically acceptable salt thereof.

Another aspect of the disclosure provides a method of treating non-small cell lung cancer by the steps of: (i) diagnosing a subject with non-small lung cancer cell; and (ii) administering to the subject an effective amount of a compound of formula (I) or a hydrate, a solvate, or a pharmaceutically acceptable salt thereof.

BRIEF DESCRIPTION OF FIGURES

FIGS. 16A-16F is a series of graphs showing the radiosensitizing effect of 1 µM RX-3117 (5 µM RX-3117 for SW1573 cells) with different doses of irradiation using a clonogenic assay. Cells were pre incubated with RX-3117 for 24 h. FIG. 16A: A2780 cells had a dose modifying factor (DMF) of 1.8. FIG. 16B: A549 cells had a DMF of 1.8. FIG. 16C: H460 cells showed a poor radiosensitizing effect. FIG. 16D: SW1573 cells had DMF of 1.5. FIG. 16E: SW1573/G-cells had DMF of 1.4. FIG. 16F: Fractionated irradiation of SW1573 cells for 5 days with 2 Gy at 24 h after incubation with 1 µM RX-3117.

FIG. 17A: SW1573, normalized spheroid volume over 15 days. Control; 1 µM RX-3117 treated; RT treatment of 2 Gy for 5 days; RT treatment of 2 Gy for 5 days and pre incubated with 1 µM RX-3117. FIG. 17B: A549 spheres, normalized spheroid volume over 15 days. Control; 1 µM RX-3117 treated; RT treatment of 2 Gy during 5 days; RT treatment of 2 Gy for 5 days and pre incubated for 24 h with 1 µM RX-3117.

FIGS. 18A-18B shows western blot analysis of DNA damage. FIG. 18A; The expression of the DSB damage marker γH2A.X in A2780 cells exposed to increasing concentrations starting from 0.1 µM-10 µM RX-3117 for 48 h. FIG. 18B: Time dependent induction of the DNA damage in SW1573 cells in combination with radiation. C* means DNA damage by 50 µM etoposide after 2 days, which served as a positive control.

FIG. 19A: Histogram of cell phases of cell lines treated with 1 µM RX-3117 for 24 h with or without radiation of 4 Gy. Cells were harvested 24 h post treatment. FIG. 19B: Cell cycle protein analysis with western blot 24 h after drug incubation and 30 min after irradiation.

FIGS. 25A-25D is a series of graphs and associated western blots showing the effect of RX-3117 on A549 and SW1573 cells at 5 µM, 10 µM, 20 µM and 50 µM for 24 or 48 hours. Cells were harvested and protein expression was measured using western blotting (FIGS. 25A and 25B). RNA was isolated and gene expression was measured using RT-PCR (FIGS. 25C and 25D). RX-3117 down regulates DNMT1 protein and gene expression.

FIGS. 28A-28C shows the effect of RX-3117 on PCFT mediated transport of MTX for 24 hours. Folic acid (FA) was added to inhibit PCFT and L-LV to inhibit RFC mediated MTX transport. Aza-CdR and aza-CR were included as a positive control.

DETAILED DESCRIPTION

Definitions

Figure 1:
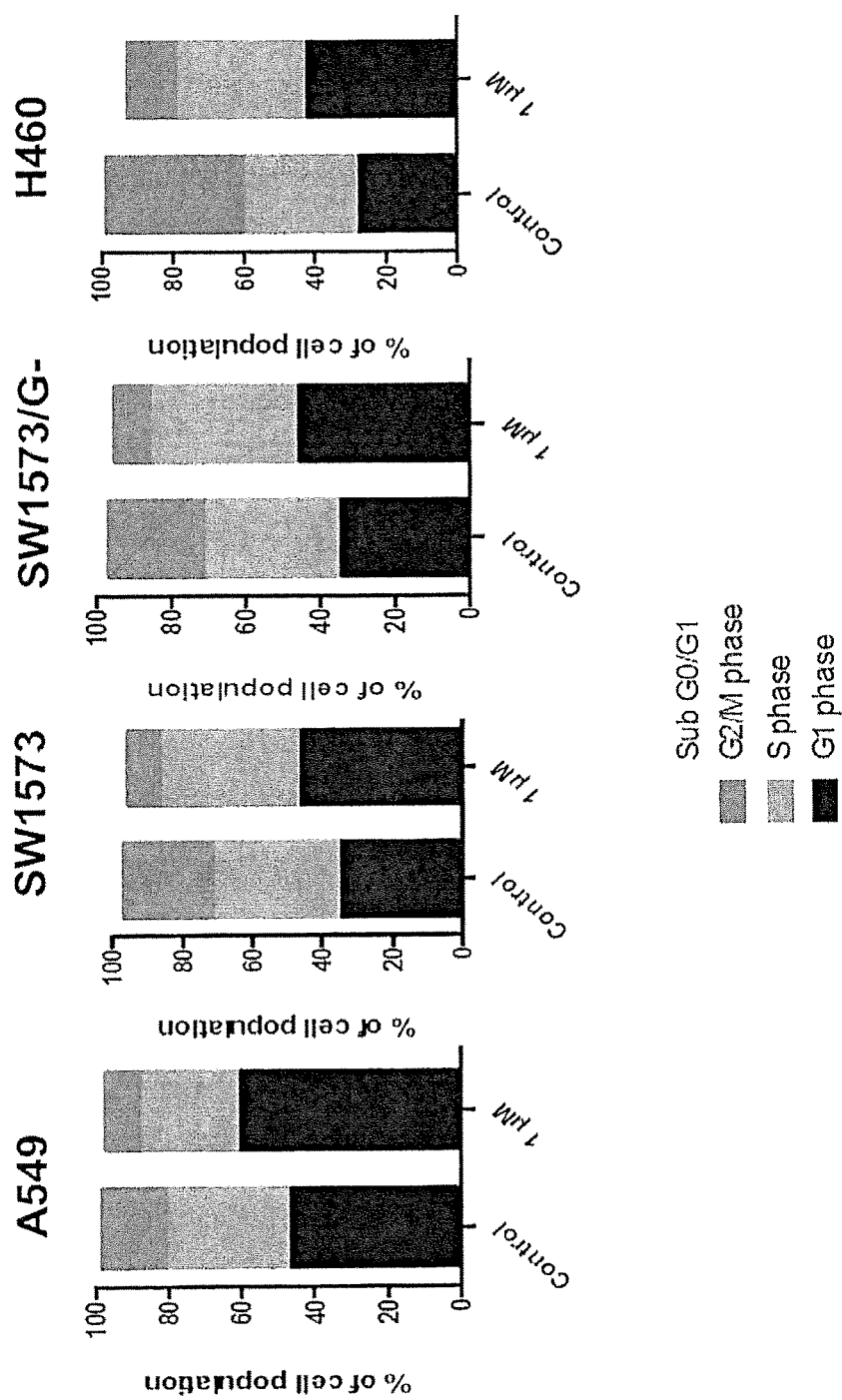
FIG. 1 is a series of bar graphs showing the effect of RX-3117 (1 μM) on A549, SW1573, SW1573/G- and H460 cells in the G1 phase after 24 hours. At a dose of 1 μM, RX-3117 induced accumulation of A549, SW1573, SW1573/G- and H460 cells in the G1 phase after 24 hours exposure.

Unless defined otherwise, the meanings of all technical and scientific terms used herein are those commonly understood by one of ordinary skill in the art to which the disclosed subject matter belongs. One of ordinary skill in the art will appreciate that any methods and materials similar or equivalent to those described herein can also be used to practice or test the disclosed subject matter.

Unless clearly indicated otherwise, the following terms as used herein have the meanings indicated below. These meanings are intended to supplement, rather than alter, the meanings of these terms as understood in the art.

"$C_{max}$" refers to the maximum observed plasma concentration.

"$T_{max}$" refers to the time at which $C_{max}$ is attained.

"$T_{1/2}$" refers to the time required for the plasma concentration of a drug to reach half of its original value. "Terminal $T_{1/2}$" refers to $T_{1/2}$ in the terminal phase.

"$AUC_{0-t}$" refers to the area under the plasma concentration versus time curve (AUC) from time zero to time t, where "t" is the last sampling time point with measurable concentration. For example, $AUC_{0-24}$ or $AUC_{0-t}$ (0-24 hours) refers to the AUC from time zero to 24 hours.

"Oral dosage form" refers to a pharmaceutical composition formulated for oral administration. The oral dosage form can be formulated to provide immediate, sustained, extended, delayed or controlled release. Examples of an oral dosage form include tablets, capsules, granulations and gel-caps.

"Effective amount" refers to an amount of a compound or pharmaceutical composition that, based on its parameters of efficacy and potential for toxicity and the knowledge of one skilled in the art, produces a desired effect, such as treating or preventing a condition. An effective amount can be administered in one or more doses.

"Contacting" refers to causing, either directly or indirectly, a compound and a cell to be in sufficient proximity to produce a desired effect, such as inducing apoptosis or modulating protein kinase. The contacting may be performed in vitro or in vivo. For example, contacting a cell with a compound may involve delivering the compound directly into the cell using known techniques such as microinjection, administering the compound to a subject carrying the cell, or incubating the cell in a medium that includes the compound.

"Treating" refers to attaining a beneficial or desired result, such as a clinical result. In some embodiments, the beneficial or desired result is any one or more of the following: inhibiting or suppressing the onset or development of a condition, reducing the severity of the condition, reducing the number or severity of symptoms associated with the condition, increasing the quality of life of a subject suffering from the condition, decreasing the dose of another medication required to treat the condition, enhancing the effect of another medication a subject is taking for the condition, and prolonging the survival of a subject having the condition.

"Preventing" refers to reducing the probability that a subject develops a condition which the subject does not have but is at risk of developing. "At risk" denotes that a subject has one or more risk factors, which are measurable parameters that correlate with the development of a condition and are known in the art. A subject having one or more of risk factors has a higher probability of developing the condition than a subject without such risk factors.

"Subject" refers to an animal, such as a mammal, including, but not limited to, a human. Hence, the methods disclosed herein can be useful in human therapy and veterinary applications. In one embodiment, the subject is a mammal. In other embodiments, the subject is a human.

"Fasted" refers to a subject that has fasted from food for at least 8 hours prior to treatment.

"Apoptosis" or "apoptotic process" refers to a programmed cell death process which begins when a cell receives an internal or external signal (apoptotic signal), and proceeds through a series of biochemical events (signaling pathway phase) which trigger an execution phase. In the execution phase, effector caspases cleave vital cellular proteins leading to the morphological changes that characterize apoptosis. These changes can include, for example, cell shrinkage, dilation of endoplasmic reticulum, cell fragmentation, formation of membrane vesicles (apoptotic bodies), deoxyribonucleic acid (DNA) fragmentation, chromatin condensation, chromosome migration, margination in cell nuclei, mitochondrial swelling, widening of the mitochondrial cristae, opening of the mitochondrial permeability transition pores, dissipation of the mitochondrial proton gradient, and/or plasma membrane blebbing. Exemplary assays used to detect and measure apoptosis include microscopic examination of pyknotic bodies as well as enzymatic assays such as Terminal deoxynucleotidyl transferase dUTP nick end labeling (TUNEL), caspase assay, annexin assay and DNA laddering. Apoptotic cells can be quantitated, for example, by FACS analysis of cells stained with propidium iodide for DNA hypoploidy.

"Inducing apoptosis" refers to causing apoptosis directly or indirectly, and may be characterized by an increased number of cells in a given cell population that undergo apoptosis, an increased rate by which a cell undergoes apoptosis, or an increased intensity, number or rate of onset of one or more morphological characteristics of apoptosis.

"Sensitizing" refers to increasing a cell's sensitivity to, or reducing a cell's resistance in responding to, an apoptotic signal.

"Apoptotic signal" refers to a stimulus that activates an apoptotic signaling pathway.

"Apoptotic signaling pathway" refers to a series of molecular signals that triggers apoptotic cell death. The pathway starts with the reception of a signal, and ends when the execution phase of apoptosis is triggered.

"Modulating" refers to altering the expression and/or activity of a biomolecule such as a protein kinase. In one embodiment, modulating refers to increasing the expression and/or activity of a biomolecule. In other embodiments, modulating refers to decreasing the expression and/or activity of a biomolecule.

"Protein kinase" refers to a kinase enzyme that modifies other proteins by phosphorylation. Examples of a protein kinase include serine/threonine protein kinase (e.g., checkpoint kinase 1, checkpoint kinase 2), tyrosine-specific protein kinase, histidine-specific protein kinase, and mixed kinase (e.g., mitogen-activated protein kinase kinase). In one embodiment, the protein kinase is a serine/threonine protein kinase. In one embodiment, the protein kinase is a serine/threonine protein kinase. In other embodiments, the protein kinase is checkpoint kinase 1 (Chk1) or checkpoint kinase 2 (Chk2). In other embodiments, the protein kinase is Chk1. In other embodiments, the protein kinase is Chk2.

"p53" refers to a protein encoded by the p53 tumor suppressor gene.

"UCK2" refers to Uridine Cytidine Kinase 2 expressed predominantly in tumor cell or tissue.

"Tumor cell" refers to a cell derived from a tumor.

"Tumor" refers to an abnormal growth of tissue or cells, whether benign or malignant. Examples include tumors found in prostate, lung, brain, breast, kidney, liver, lung, intestines, lymph, muscle, bone, bone marrow, uterus, ovary, vagina, vulva, pancreas, adrenal gland, central nervous system, peripheral nervous system, cervix, bladder, endometrium, throat, esophagus, larynx, thyroid, blood, penal, testicular, thymus, skin, spine, stomach, bile duct, small bowel, hepatobiliary tract, colorectal, colon, rectum, anus, endocrine, eye, and gall bladder.

"Cancer" refers to a malignant tumor. Cancer cells may or may not invade the surrounding tissue and, hence, may or may not metastasize to new body sites. Cancer encompasses carcinomas, which are cancers of epithelial cells; carcinomas include squamous cell carcinomas, adenocarcinomas, melanomas, and hepatomas. Cancer also encompasses sarcomas, which are tumors of mesenchymal origin; sarcomas include osteogenic sarcomas, leukemias, and lymphomas. Cancers may involve one or more neoplastic cell type.

"Anti-tumor agent" refers to any agent useful for treating or preventing tumor. Examples of an anti-tumor agent include the active agents described in Pharmaceutical Compositions, infra. In embodiments, the anti-tumor agent in addition to RX-3117 is selected from antimetabolites, DNA-fragmenting agents, DNA-crosslinking agents, intercalating agents, protein synthesis inhibitors, topoisomerase I poisons, topoisomerase II poisons, microtubule-directed agents, kinase inhibitors, polyphenols, hormones, hormone antagonists, death receptor agonists, immune checkpoint inhibitors, anti-programmed cell death 1 (PD-1) receptor antibodies and anti-programmed cell death ligand 1 (PD-L1) antibodies. In other embodiments, the additional anti-tumor agent is a PD-1 receptor antibody. In other embodiments, the additional anti-tumor agent is pembrolizumab. In other embodiments, the additional anti-tumor agent is nivolumab. In other embodiments, the additional anti-tumor agent is duryalumab. In other embodiments, the additional anti-tumor agent is combination of nivolumab and pembrolizumab.

"Radiation" refers to any radiation useful for treating or preventing tumor. Examples of radiation include X-rays, gamma rays, and charged particles. The radiation may be delivered by any form of radiation therapy, such as external beam radiotherapy (EBRT, XBRT or teletherapy), brachytherapy (internal radiation therapy or sealed source therapy), intraoperative radiotherapy, or systemic radiation therapy.

"Isolation" refers to any process by which an intermediate is separated from a reaction mixture by purification such as by chromatography, distillation, filtration, extraction, drying or recrystallization.

"Fixed reactor or vessel" refers to a reactor system in a fixed place in the plan that cannot be moved.

"Such as" has the same meaning as "such as but not limited to." Similarly, "include" has the same meaning as "include but not limited to," while "including" has the same meaning as "including but not limited to."

The singular forms "a," "or," and "the" include plural references unless the context dictates otherwise. Thus, for example, a reference to "a compound" may include one or more compound(s) and/or equivalent(s) thereof.

Any numerical range disclosed herein encompasses the upper and lower limits and each intervening value, unless otherwise specified.

Other than in the working examples, or where otherwise indicated, numerical values (such as numbers expressing quantities of ingredients, reaction conditions) as used in the specification and claims are modified by the term "about". Accordingly, unless indicated to the contrary, such numbers are approximations that may vary depending upon the desired properties sought to be obtained. At the very least, and not as an attempt to limit the application of the doctrine of equivalents to the scope of the claims, each numerical parameter should be construed in light of the number of significant digits and ordinary rounding techniques.

While the numerical parameters setting forth the scope of the disclosed subject matter are approximations, the numerical values set forth in the working examples are reported as precisely as possible. Any numerical value, however, inherently contains certain errors necessarily resulting from the standard deviation found in its respective testing measurements.

Methods of Inducing Apoptosis or Sensitizing a Cell to an Apoptotic Signal

One aspect of the disclosure provides a method of inducing apoptosis by the steps of administering an effective amount of a compound of formula (I) (RX-3117)

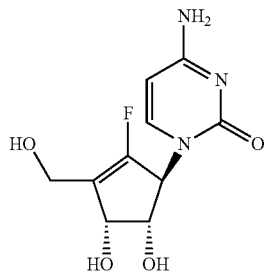

(I)

or a hydrate, a solvate, or a pharmaceutically acceptable salt thereof. In embodiments, the compound of formula (I) may be administrated as a monohydrate or free form.

Another aspect of the disclosure provides a method of inducing apoptosis in a cell by the steps of contacting the cell with an effective amount of a compound of formula (I) or a hydrate, a solvate, or a pharmaceutically acceptable salt thereof.

In one embodiment, the method induces apoptosis through single-strand break (SSB) or double-strand break (DSB). In other embodiments, the method induces apoptosis through SSB. In other embodiments, the method induces apoptosis through DSB.

Another aspect of the disclosure provides a method of sensitizing a cell to an apoptotic signal by contacting the cell with an effective amount of a compound of formula (I) or a hydrate, a solvate, or a pharmaceutically acceptable salt thereof.

In one embodiment of any the methods provided herein, the cell is a tumor cell. In other embodiments, the cell is a malignant tumor cell. In other embodiments, the cell is a lung cancer cell. In other embodiments, the cell is a non-small cell lung cancer cell. In other embodiments, the cell is a pancreatic cancer cell. In other embodiments, the cell is a bladder cancer cell. In other embodiments, the cell is a colorectal cancer cell. In other embodiments, the cell is a mammalian cell or a cell in a mammal. In other embodiments, the cell is a human cell or a cell in a human.

Methods of Modulating Protein Kinase

Another aspect of the disclosure provides a method of modulating a protein kinase in a cell in which the method includes contacting the cell with an effective amount of a compound of formula (I) or a hydrate, a solvate, or a pharmaceutically acceptable salt thereof. In embodiments, the protein kinase is modulated by increasing the protein kinase. The increase can be by, for example, 5% or more, 10% or more, 20% or more, 25% or more, 30% or more, 40% or more, 50% or more, 60% or more, 70% or more, 75% or more, 80% or more, 90% or more, or 95% or more.

In embodiments, the protein kinase is a checkpoint protein kinase. In other embodiments, the protein kinase is checkpoint kinase 1 (Chk1) or checkpoint kinase 2 (Chk2). In other embodiments, the protein kinase is Chk1. In other embodiments, the protein kinase is Chk2.

In embodiments, the cell is in a mammal. In other embodiments, the cell is in a human.

In embodiments, the method increases the protein kinase expression level.

Methods of Treating or Preventing Non-Small Cell Lung Cancer

Another aspect of the disclosure provides a method of treating or preventing a non-small cell lung cancer by the steps of:

(i) diagnosing a subject with non-small lung cancer cell; and (ii) administering to the subject an effective amount of a compound of formula (I) or a hydrate, a solvate, or a pharmaceutically acceptable salt thereof.

Methods of Predicting Efficacy of Treatment

Another aspect of the disclosure provides a method of predicting efficacy of treatment of a subject in need thereof with a compound of formula (I) or a hydrate, a solvate, or a pharmaceutically acceptable salt thereof, by the steps of:

(i) collecting a sample of tumor cell or tissue from the subject;

(ii) measuring one of protein kinases or p53 expression level in the sample, (iii) contacting the tumor cell or tissue with a compound of formula (I);

(iv) measuring one of protein kinases or p53 expression level in the tumor cell or tissue after contact with the compound of formula (I), wherein an increase in protein kinases or p53 expression level indicates likelihood of efficacy.

In embodiments, contacting the tumor cell or tissue with a compound of formula (I) is accomplished by contacting the sample of tumor cell or tissue. In such embodiments, measuring one of protein kinases or p53 expression level in the tumor cell or tissue after contact with the compound of formula (I) is conducted on the sample. In other embodiments, contacting the tumor cell or tissue with a compound of formula (I) is accomplished by administering the compound of formula (I) to the subject. In such embodiments, measuring one of protein kinases or p53 expression level in the tumor cell or tissue after contact with the compound of formula (I) is conducted by collecting a second sample of tumor cell or tissue from the subject and measuring one of protein kinases or p53 expression level in the second sample.

In embodiments, the method further comprises administering the subject with the compound of formula (I) if an increase in one of protein kinases or p53 expression level is detected. The protein kinase is considered to have increased if the amount of protein kinase is greater by a statistically significant amount. Thus the increase may be by 5% or more, 10% or more, 20% or more, or 25% or more. In other embodiments, the method further comprises the step of measuring protein Cdc25C or p-Cdc25C expression level in the sample in steps (ii) and (iv), wherein a decrease in protein Cdc25C or p-Cdc25C expression level indicates likelihood of efficacy. The protein Cdc25C or p-Cdc25C expression level is considered to have decreased if the protein Cdc25C or p-Cdc25C expression level is reduced by a statistically significant amount. Thus the reduction may be by 5% or more, 10% or more, 20% or more, or 25% or more. In other embodiments, the method further comprises administering the subject with the compound of formula (I) if an increase in one of protein kinases or p53 expression level and a decrease in protein Cdc25C or p-Cdc25C expression level are detected.

In embodiments, the compound of formula (I) is administrated as a monohydrate. In other embodiments, the compound of formula (I) is administrated free of solvates, hydrates and salts.

In embodiments, the method comprises measuring protein kinase expression level in steps (ii) and (iv). In other embodiments, the protein kinase is a checkpoint kinase. In other embodiments, the protein kinase is Chk1 or Chk2. In other embodiments, the protein kinase is Chk1. In other embodiments, the protein kinase is Chk2.

Another aspect of the disclosure provides a method of predicting efficacy of treatment of a subject in need thereof with a compound of formula (I) or a hydrate, a solvate, or a pharmaceutically acceptable salt thereof, by the steps of:

(i) collecting a sample of tumor cell or tissue from the subject; and (ii) measuring the level of UCK2 expression in the tumor cell or tissue;

wherein the expression level of UCK2 indicates a likelihood of efficacy of treatment with a compound of formula (I).

In embodiments, the method further comprises administering the subject with the compound of formula (I) if an increased expression of UCK2 is measured in the tumor cell or tissue. In embodiments, UCK2 expression is measured by immunoblotting the protein level of UCK2 normalized to beta-actin. The UCK2 is considered to have an increased expression level if the amount of UCK2 expression is greater by a statistically significant amount compared to a predetermined level. Thus the increase may be by 5% or more, 10% or more, 20% or more, or 25% or more. In embodiments, the predetermined level may be the level of UCK2 expression on a non-tumor cell. In embodiments, the predetermined level may be the level of UCK2 expression on a non-tumor cell of the subject.

In embodiments, the subject is a mammal. In other embodiments, the subject is a human.

In embodiments, the tumor cell is lung cancer cell. In other embodiments, the tumor cell is non-small cell lung cancer cell.

Methods of Treating or Preventing a Tumor

Another aspect of the disclosure provides a method of treating or preventing a tumor by the steps of administering to a subject in need thereof an oral dosage form that includes an effective amount of a compound of formula (I)

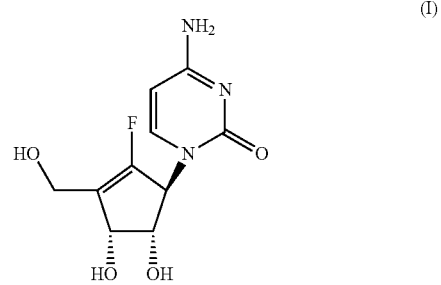 [SMILES: Nc1ccn([C@@H]2C(F)=C(CO)[C@@H](O)[C@H]2O)c(=O)n1]

or a hydrate, a solvate, or a pharmaceutically acceptable salt thereof, at a dosage of about 300-2,000 mg/day. In other embodiments, the dosage is about 400-800 mg/day. In other embodiments, the dosage is about 500-700 mg/day. In other embodiments, the dosage is about 300 mg/day. In other embodiments, the dosage is about 400 mg/day. In other embodiments, the dosage is about 500 mg/day. In other embodiments, the dosage is about 600 mg/day. In other embodiments, the dosage is about 700 mg/day. In other embodiments, the dosage is about 800 mg/day.

The dosage of about 300-2,000 mg/day is based upon an adult human having a weight or body mass of about 60-80 kg. Thus, the dosage can range from about 5-33 mg/kg/day. Additional dosages based on subject weight may be readily calculated from these values. Similarly, persons skilled in the art will be able to calculate dosages for other species based on known correlations to human dosages.

In embodiments, the oral dosage form is administered 3-7 days per week. In other embodiments, the oral dosage form is administered 4-7 days per week. In other embodiments, the oral dosage form is administered 5-7 days per week. In other embodiments, the oral dosage form is administered 5 or 7 days per week. In other embodiments, the oral dosage form is administered 3 days per week. In other embodiments, the oral dosage form is administered 4 days per week. In other embodiments, the oral dosage form is administered 5 days per week. In other embodiments, the oral dosage form is administered 6 days per week. In other embodiments, the oral dosage form is administered 7 days per week.

In embodiments, the total daily dose is administered in one or more doses. In other embodiments, the oral dosage form is administered once daily. In other embodiments, the oral dosage form is administered twice daily. In other embodiments, the oral dosage form is administered three times daily. In other embodiments, the oral dosage form is administered four times daily.

In embodiments, the oral dosage form is administered at a dosage of up to about 20,000 mg/month. The total monthly dose can be administered 1-7 days per week either for three weeks followed by one week of rest ("off week"), or for four weeks without rest. For each week of treatment, the oral dosage form may be administered 1-7 days per week. In one embodiment, the oral dosage form is administered for three weeks followed by one week of rest. In other embodiments, the oral dosage form is administered 3-7 days per week for three weeks followed by one week of rest. In other embodiments, the oral dosage form is administered 5-7 days per week for three weeks followed by one week of rest. In other embodiments, the oral dosage form is administered daily for three weeks followed by one week of rest. In other embodiments, the oral dosage form is administered daily for 28 days. Each dosing cycle consists of either 3 weeks of treatment followed by 1 week of rest, or 4 continuous/consecutive weeks of treatment. The dosing cycle may be repeated as often as necessary as determined by a person skilled in the art. In one embodiment, the oral dosage form is administered for up to 12 dosing cycles. In other embodiments, the oral dosage form is administered for up to 6 dosing cycles.

In embodiments, the oral dosage form is administered at a dosage of about 300-2,000 mg/day 5-7 days per week. In other embodiments, the dosage is about 400-800 mg/day 5-7 days per week. In other embodiments, the dosage is about 500-700 mg/day 5-7 days per week. In other embodiments, the dosage is about 500-700 mg/day 5 or 7 days per week. In other embodiments, the dosage is about 500 mg/day 5 days per week. In other embodiments, the dosage is about 500 mg/day 7 days per week. In other embodiments, the dosage is about 600 mg/day 5 days per week. In other embodiments, the dosage is about 600 mg/day 7 days per week. In other embodiments, the dosage is about 700 mg/day 5 days per week. In other embodiments, the dosage is about 70 mg/day 7 days per week.

In embodiments, the oral dosage form is administered once daily at about 400 mg/day 5 days per week. In other embodiments, the oral dosage form is administered once daily at about 500 mg/day 5 days a week. In other embodiments, the oral dosage form is administered once daily at about 600 mg/day 5 days per week. In other embodiments, the oral dosage form is administered once daily at about 700 mg/day 5 days per week. In other embodiments, the oral dosage form is administered once daily at about 800 mg/day 5 days per week.

In embodiments, the oral dosage form is administered once daily at about 400 mg/day 7 days per week. In other embodiments, the oral dosage form is administered once daily at about 500 mg/day 7 days per week. In other embodiments, the oral dosage form is administered once daily at about 600 mg/day 7 days per week. In other embodiments, the oral dosage form is administered once daily at about 700 mg/day 7 days per week. In other embodiments, the oral dosage form is administered once daily at about 800 mg/day 7 days per week.

In embodiments, the oral dosage form is administered at about 3-35 mg/kg/day 5-7 days per week. In other embodiments, the oral dosage form is administered at about 3-35 mg/kg/day 5 days per week. In other embodiments, the oral dosage form is administered at about 3-35 mg/kg/day 6 days per week. In other embodiments, the oral dosage form is administered at about 3-35 mg/kg/day 7 days per week. In other embodiments, the oral dosage form is administered at about 6-12 mg/kg/day 5-7 days per week. In other embodiments, the oral dosage form is administered at about 6-12 mg/kg/day 5 days per week. In other embodiments, the oral dosage form is administered at about 6-12 mg/kg/day 6 days per week. In other embodiments, the oral dosage form is administered at about 6-12 mg/kg/day 7 days per week.

In some embodiments, the oral dosage form is a solid. In other embodiments, the oral dosage form is a tablet. In other embodiments, the oral dosage form is a capsule. In other embodiments, the oral dosage form is immediate release. In other embodiments, the oral dosage form is extended release.

In embodiments, the oral dosage form is administered after the subject has fasted from food for at least about 8 hours. In other embodiments, the subject continues to fast from food for at least about 1 hour after administration. In other embodiments, the oral dosage form is administered to the subject with food.

In embodiments, the compound of formula (I) is administrated as a monohydrate. In other embodiments, the compound of formula (I) is administrated free of solvates, hydrates and salts.

In embodiments, the oral dosage form provides a $T_{1/2}$ of about 3-20 hours after a single administration. In other embodiments, the oral dosage form provides a $T_{1/2}$ of about 5-10 hours after a single administration. In other embodiments, the oral dosage form provides a $T_{1/2}$ of about 6-9 hours after a single administration. In other embodiments, the oral dosage form provides a $T_{1/2}$ of about 9-11 hours after a single administration. In other embodiments, the oral dosage form provides a $T_{1/2}$ of about 6-7 hours after a single administration. In other embodiments, the oral dosage form provides a $T_{1/2}$ of about 6 hours after a single administration. In other embodiments, the oral dosage form provides a $T_{1/2}$ of about 7 hours after a single administration. In other embodiments, the oral dosage form provides a $T_{1/2}$ of about 8 hours after a single administration. In other embodiments, the oral dosage form provides a $T_{1/2}$ of about 9 hours after a single administration. In other embodiments, the oral dosage form provides a $T_{1/2}$ of about 10 hours after a single administration. In other embodiments, the oral dosage form provides a $T_{1/2}$ of about 11 hours after a single administration.

In embodiments, the oral dosage form provides a $T_{max}$ of about 2-6 hours after a single administration. In other embodiments, the oral dosage form provides a $T_{max}$ of about 4-6 hours after a single administration. In other embodiments, the oral dosage form provides a $T_{max}$ of about 2-4 hours after a single administration. In other embodiments, the oral dosage form provides a $T_{max}$ of about 2 hours after a single administration. In other embodiments, the oral dosage form provides a $T_{max}$ of about 3 hours after a single administration. In other embodiments, the oral dosage form provides a $T_{max}$ of about 4 hours after a single administration. In other embodiments, the oral dosage form provides a $T_{max}$ of about 5 hours after a single administration. In other embodiments, the oral dosage form provides a $T_{max}$ of about 6 hours after a single administration.

In embodiments, the oral dosage form provides a $C_{max}$ of about 30-3,000 ng/mL after a single administration. In other embodiments, the oral dosage form provides a $C_{max}$ of about 600-2,000 ng/mL after a single administration. In other embodiments, the oral dosage form provides a $C_{max}$ of about 700-1,500 ng/mL after a single administration. In other embodiments, the oral dosage form provides a $C_{max}$ of about 600-1,100 ng/mL after a single administration. In other embodiments, the oral dosage form provides a $C_{max}$ of about 700-1,100 ng/mL after a single administration. In other embodiments, the oral dosage form provides a $C_{max}$ of about 600-700 ng/mL after a single administration. In other embodiments, the oral dosage form provides a $C_{max}$ of about 700-800 ng/mL after a single administration. In other embodiments, the oral dosage form provides a $C_{max}$ of about 800-900 ng/mL after a single administration. In other embodiments, the oral dosage form provides a $C_{max}$ of about 900-1,000 ng/mL after a single administration. In other embodiments, the oral dosage form provides a $C_{max}$ of about 1,000-1,100 ng/mL after a single administration.

In embodiments, the oral dosage form provides an $AUC_{0-t}$ (0-24 hours) of about 200-18,000 hr·ng/mL after a single administration. In other embodiments, the oral dosage form provides an $AUC_{0-t}$ (0-24 hours) of about 7,000-14,000 hr·ng/mL after a single administration. In other embodiments, the oral dosage form provides an $AUC_{0-t}$ (0-24 hours) of about 8,000-12,000 hr·ng/mL after a single administration. In other embodiments, the oral dosage form provides an $AUC_{0-t}$ (0-24 hours) of about 8,000-10,000 hr·ng/mL after a single administration. In other embodiments, the oral dosage form provides an $AUC_{0-t}$ (0-24 hours) of about 8,000-9,000 hr·ng/mL after a single administration. In other embodiments, the oral dosage form provides an $AUC_{0-t}$ (0-24 hours) of about 9,000-10,000 hr·ng/mL after a single administration. In other embodiments, the oral dosage form provides an $AUC_{0-t}$ (0-24 hours) of about 10,000-11,000 hr·ng/mL after a single administration. In other embodiments, the oral dosage form provides an $AUC_{0-t}$ (0-24 hours) of about 11,000-12,000 hr·ng/mL after a single administration.

In embodiments, the tumor is ovarian cancer; metastatic breast cancer; adenocarcinoma of the pancreas; gastrointestinal cancer such as colorectal adenocarcinoma or cancer of the esophagus, stomach, pancreas, small bowel, hepatobiliary tract, colon, rectum or anus; bladder cancer such as metastatic bladder cancer, muscle invasive bladder cancer or non-muscle invasive bladder cancer; cervical cancer; lung cancer; non-small cell lung cancer; or renal cell carcinoma. In other embodiments, the tumor is pancreatic, bladder or colorectal cancer. In other embodiments, the tumor is pancreatic cancer. In other embodiments, the cancer is bladder cancer. In other embodiments, the cancer is colorectal cancer. In other embodiments, the cancer is colon cancer. In other embodiments, the cancer is rectal cancer. In other embodiments, the tumor is non-small cell lung cancer and the compound of formula (I) or a hydrate, a solvate, or a pharmaceutically acceptable salt thereof is administered with cisplatin. In other embodiments, the tumor is resistant to gemcitabine. See Yang et al., *Anticancer Research*, 34:6951-6960 (2014) (showing efficacy of RX-3117 in various xenograft models, even in tumors resistant to gemcitabine).

In embodiments, the subject is a mammal. In other embodiments, the subject is a human.

Kits for Testing Efficacy of Treatment

Another aspect of the disclosure provides a kit for testing potential efficacy of a compound of formula (I)

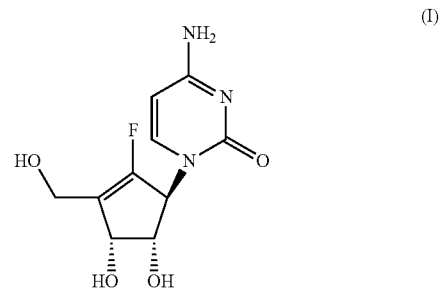 [SMILES: Nc1ccn([C@@H]2C(F)=C(CO)[C@@H](O)[C@H]2O)c(=O)n1]

or a hydrate, a solvate, or a pharmaceutically acceptable salt in the treatment of tumor, using an assay that measures one of protein kinases, p53, or UCK2 expression level in a sample of tumor cell.

In embodiments, the kit further comprises an assay that measures protein Cdc25C or p-Cdc25C expression level in a sample of tumor cell.

In any embodiment, the tumor cell is lung cancer cell. In other embodiments, the tumor cell is non-small cell lung cancer cell. In other embodiments, the tumor cell is pancreatic cancer cell or bladder cancer cell.

Pharmaceutical Compositions

In any of the methods and kits provided herein, the compound of formula (I) may be in a pharmaceutical composition. Such pharmaceutical composition can be prepared as any appropriate unit dosage form. For example, the pharmaceutical compositions can be formulated for administration in solid or liquid form, including those adapted for the following: (1) oral administration, for example, as drenches, tablets (such as those targeted for buccal, sublingual and systemic absorption, including over-encapsulation tablets), capsules (such as dry filled, hard gelatin, soft gelatin or over-encapsulation capsules), caplets, boluses, powders, sachets, granules, pastes, mouth sprays, troches, lozenges, pellets, syrups, suspensions, elixirs, liquids, liposomes, emulsions and microemulsions; or (2) parenteral administration by, for example, subcutaneous, intramuscular, intravenous or epidural injection as, for example, a sterile solution or suspension. Additionally, the pharmaceutical compositions can be formulated for immediate, sustained, extended, delayed or controlled release.

In one embodiment, the pharmaceutical composition is formulated for oral administration. In embodiments, the pharmaceutical composition is in tablet or capsule form. In other embodiments, the pharmaceutical composition is in tablet form. In other embodiments, the pharmaceutical composition is in capsule form. In other embodiments, the tablet or capsule is formulated for immediate release. In other embodiments, the tablet or capsule is formulated for sustained, extended, delayed or controlled release.

Tablets can be made by compression or molding, optionally with one or more accessory ingredients. Compressed tablets can be prepared by compressing in a suitable machine Compound (I) in a free-flowing form such as a powder or granules, optionally mixed with a binder, lubricant, inert diluent, preservative, surface-active or dispersing agent. Molded tablets can be made by molding in a suitable machine a mixture of the powdered compound moistened with an inert liquid diluent. The tablets can be optionally coated or scored and can be formulated so as to provide sustained, extended, delayed or controlled release of Compound (I). Methods of formulating such sustained, extended, delayed or controlled release compositions are known in the art and disclosed in issued U.S. patents, including but not limited to U.S. Pat. Nos. 4,369,174; 4,842,866; and the references cited therein. Coatings can be used for delivery of compounds to the intestine (see, e.g., U.S. Pat. Nos. 6,638,534; 5,217,720; 6,569,457; and the references cited therein). In addition to tablets, other dosage forms, such as capsules, granulations and gel-caps, can be formulated to provide sustained, extended, delayed or controlled release of Compound (I).

In embodiments, the pharmaceutical composition is formulated for parenteral administration. Examples of a pharmaceutical composition suitable for parenteral administration include aqueous sterile injection solutions and non-aqueous sterile injection solutions, each containing, for example, anti-oxidants, buffers, bacteriostats and/or solutes that render the formulation isotonic with the blood of the intended recipient; and aqueous sterile suspensions and non-aqueous sterile suspensions, each containing, for example, suspending agents and/or thickening agents. The formulations can be presented in unit-dose or multi-dose containers, for example, sealed ampules or vials, and can be stored in a freeze dried (lyophilized) condition requiring only the addition of a sterile liquid carrier, such as water, immediately prior to use. In one embodiment, the pharmaceutical composition is formulated for intravenous administration.

In embodiments, the pharmaceutical composition further comprises a pharmaceutically acceptable excipient. A pharmaceutically acceptable excipient may be any substance, not itself a therapeutic agent, used as a carrier, diluent, adjuvant, binder, and/or vehicle for delivery of a therapeutic agent to a patient, or added to a pharmaceutical composition to improve its handling or storage properties or to permit or facilitate formation of a compound or pharmaceutical composition into a unit dosage form for administration. Pharmaceutically acceptable excipients are known in the pharmaceutical arts and are disclosed, for example, in *Remington: The Science and Practice of Pharmacy,* 21st Ed. (Lippincott Williams & Wilkins, Baltimore, Md., 2005). As will be known to those in the art, pharmaceutically acceptable excipients can provide a variety of functions and can be described as wetting agents, buffering agents, suspending agents, lubricating agents, emulsifiers, disintegrants, absorbents, preservatives, surfactants, colorants, flavorants, and sweeteners. Examples of pharmaceutically acceptable excipients include without limitation: (1) sugars, such as lactose, glucose and sucrose; (2) starches, such as corn starch and potato starch; (3) cellulose and its derivatives, such as sodium carboxymethyl cellulose, ethyl cellulose, cellulose acetate, hydroxypropyl methylcellulose, and hydroxypropylcellulose; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) pH buffered solutions; (21) polyesters, polycarbonates and/or polyanhydrides; and (22) other non-toxic compatible substances employed in pharmaceutical formulations.

In some embodiments, the pharmaceutical composition further comprises at least one active agent in addition to RX-3117. The active agent may be an antineoplastic, chemotherapeutic, cytotoxic, radiotherapeutic (external-beam radiation therapy, internal radiation therapy, or systemic radiation therapy) or any other agent capable of inducing apoptosis, sensitizing a cell to apoptosis, modulating protein kinase or treating neoplasm, tumor or cancer. Examples of the active agent include: (1) antimetabolites, such as cytarabine, fludarabine, 5-fluoro-2'-deoxyuiridine, gemcitabine, hydroxyurea or methotrexate; (2) DNA-fragmenting agents, such as bleomycin, (3) DNA-crosslinking agents, such as chlorambucil, cisplatin, cyclophosphamide and nitrogen mustard; (4) intercalating agents such as adriamycin (doxorubicin) and mitoxantrone; (5) protein synthesis inhibitors, such as L-asparaginase, cycloheximide, puromycin and diphtheria toxin; (6) topoisomerase I poisons, such as camptothecin and topotecan; (7) topoisomerase II poisons, such as etoposide (VP-16) and teniposide; (8) microtubule-directed agents, such as colcemid, colchicine, paclitaxel, vinblastine and vincristine; (9) kinase inhibitors such as flavopiridol, staurosporin and 7-hydroxystaurosporine; (10) polyphenols such as quercetin, resveratrol, piceatannol, epigallocatechine gallate, theaflavins, flavanols, procyanidins, betulinic acid and derivatives thereof; (11) hormones such as glucocorticoids and fenretinide; (12) hormone antagonists, such as tamoxifen, finasteride and LHRH antagonists; and (13) death receptor agonists, such as tumor necrosis factor a (TNF-α), tumor necrosis factor β (TNF-β), LT-β (lymphotoxin-β), TRAIL (Apo2L, DR4 ligand), CD95 (Fas, APO-1) ligand, TRAMP (DR3, Apo-3) ligand, DR6 ligand and fragments and derivatives thereof.

In embodiments, the amount of the compound of formula (I) or hydrate, solvate, or pharmaceutically acceptable salt in the pharmaceutical composition is between about 0.1% and about 100% by weight. In other embodiments, the amount is between about 0.5% and about 99.5% by weight. In embodiments, the amount is between about 10% and about 95% by weight. In embodiments, the amount is between about 15% and about 90% by weight. In embodiments, the amount is between about 80% and about 90% by weight. In embodiments, the amount is between about 80% and about 85% by weight. In embodiments, the amount is at least 30%, at least 40%, at least 50%, at least 60%, at least 70%, or at least 80%. In embodiments, the pharmaceutical composition is an oral dosage form. In embodiment, the pharmaceutical composition is a tablet.

Methods of Administration

In any of the methods provided herein, administration of the compound or pharmaceutical composition may be via any accepted mode known in the art, such as orally or parenterally. The term "parenterally" includes without limitation subcutaneously, intravenously, intramuscularly, intraperitoneally, intravesically, intrathecally, intraventricularly, intrasternally, intracranially, by intraosseous injection and by infusion techniques. In one embodiment, the compound or pharmaceutical composition is administered orally. In other embodiments, the compound or pharmaceutical composition is administered parenterally. In other embodiments, the compound or pharmaceutical composition is administered intravenously.

In one embodiment, the compound or pharmaceutical composition is administered orally at a dose or dosage as disclosed herein, such as in Methods of Treating or Preventing Tumor, supra. In any of the methods disclosed herein, the compound or pharmaceutical composition may be administered based on a weight based dose. In other embodiments, the effective amount is about 0.01 to about 100 mg/kg/day or about 3 to about 35 mg/kg/day. In embodiments, the effective amount is about 6 to 12 mg/kg/day.

The dose level can be adjusted for intravenous administration. In such case, the compound or pharmaceutical composition can be administered in an amount of between about 0.01 µg/kg/min to about 100 µg/kg/min.

Combination Therapy

In any of the methods of treating or preventing a tumor provided herein, the method may further comprise administering RX-3117 with one or more additional anti-tumor agent or radiation to the subject. In one embodiment, the method further comprises administering radiation to the subject. In other embodiments, the method further comprises administering one or more additional anti-tumor agent to the subject.

The additional anti-tumor agent or radiation may be administered before, after, or during administration of the compound of formula (I) or hydrate, solvate, or pharmaceutically acceptable salt thereof. In one embodiment, the additional anti-tumor agent or radiation is administered before administration of the compound of formula (I) or hydrate, solvate, or pharmaceutically acceptable salt thereof. In other embodiments, the additional anti-tumor agent or radiation is administered after administration of the compound of formula (I) or hydrate, solvate, or pharmaceutically acceptable salt thereof. In other embodiments, the additional anti-tumor agent or radiation is administered during administration of the compound of formula (I) or hydrate, solvate, or pharmaceutically acceptable salt thereof. In other embodiments, the additional anti-tumor agent and the compound of formula (I) or hydrate, solvate, or pharmaceutically acceptable salt thereof are formulated into a pharmaceutical composition for concurrent administration.

Radiosensitizing Effect

The radiosensitizing effect of RX-3117 was studied in A2780 ovarian cancer cells and NSCLC cell lines. RX-3117 was found to have a schedule dependent radiosensitizing effect, but only at preincubation (dose modifying factors: 1.4-1.8), observed at pulse and fractionated irradiation. Radiosensitizion was also seen in a 3-dimensional spheroid model. At a low radiosensitizing concentration, RX-3117 in combination with radiation led to an accumulation of cells in S-phase, which was accompanied by an increase of all cell cycle proteins such as p-Chk2 and p-cdc25C. In addition, RX-3117 caused cell killing due to DNA damage. In conclusion, the in vitro experiments showed radiosensitizing effect of RX-3117.

Lung cancer patients are standardly being treated with surgery and those in advanced disease receive chemotherapy (Baas P, Belderbos J S A, Senan S, Kwa H B, van Bochove A, van Tinteren H, Burgers J A and van Meerbeeck J P: Concurrent chemotherapy (carboplatin, paclitaxel, etoposide) and involved-field radiotherapy in limited stage small cell lung cancer: a Dutch multicenter phase II study. *Br J Cancer* 94: 625-30, 2006). A combination of the cytidine analog, gemcitabine and cisplatin is being used in the clinic to treat the disease (El-Naggar M, Ebbing E, Bijnsdorp I, van den Berg J and Peters G J: Radiosensitization by thymidine phosphorylase inhibitor in thymidine phosphorylase negative and overexpressing bladder cancer cell lines. *Nucleosides Nucleotides Nucleic Acids* 33: 413-21, 2014). However, resistance is a limiting factor, and, therefore, there is a need for novel drugs which bypass the resistance mechanism and ideally show effective combination properties.

Mechanism of RX-3117 Action

Figure 14:
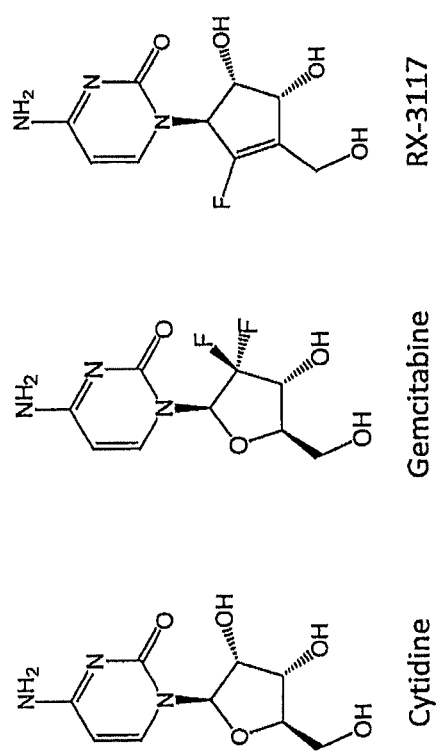
FIG. 14 shows structural formulas for Cytidine, Gemcitabine, and the novel cytidine analog RX-3117.
Figures 21, 22:
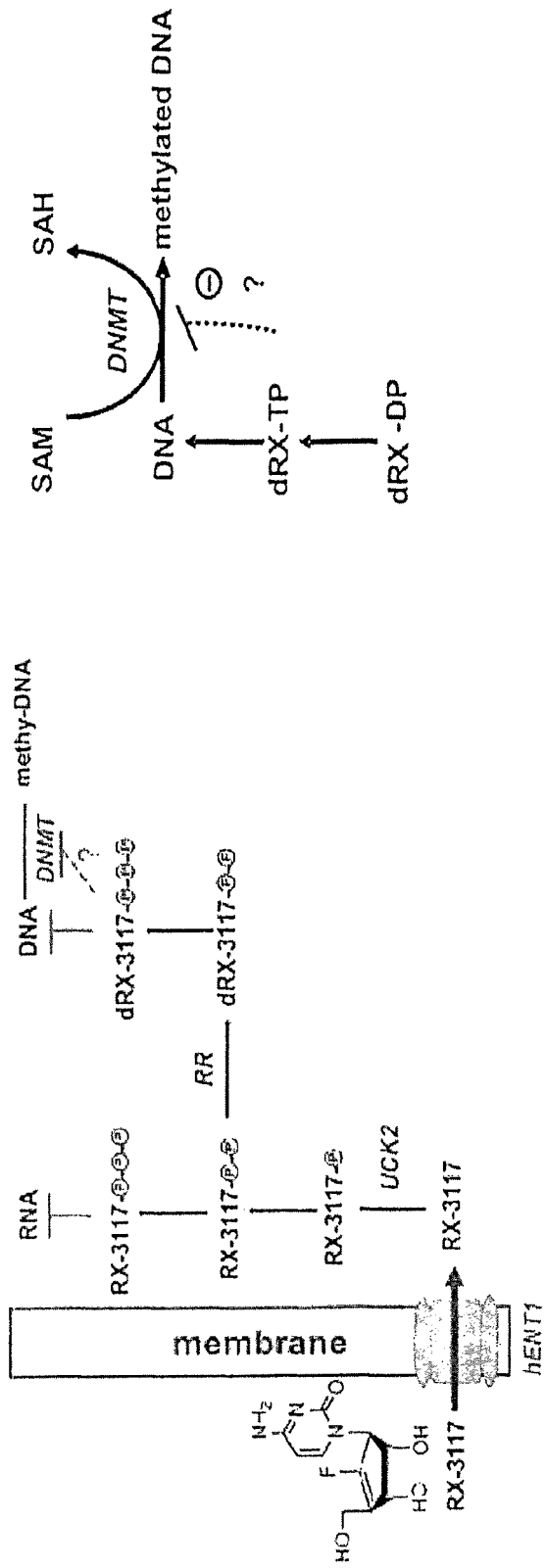
FIG. 21 shows an overview metabolic pathway of RX-3117.
FIG. 22 shows a schematic of the mechanism of down-regulation of maintenance DNA methyltransferase (DNMT1) by RX-3117.

RX-3117 is an analog of cytidine (FIG. 14). It has a modification on the ribose molecule consisting of a carbon-fluorine bond instead of oxygen and a double bond (Choi W J, Chung H-J, Chandra G, Alexander V, Zhao L X, Lee H W, Nayak A, Majik M S, Kim H O, Kim J-H, Lee Y B, Ahn C H, Lee S K and Jeong L S: Fluorocyclopentenyl-cytosine with broad spectrum and potent antitumor activity. *J Med Chem* 55: 4521-5, 2012). As shown in FIG. 21, RX-3117 enters the cell via human equilibrative nucleoside transporter (hENT) (Peters G J, Smid K, Vecchi L, Kathmann I, Sarkisjan D, Honeywell R J, Losekoot N, Ohne O, Orbach A, Blaugrund E, Jeong L S, Lee Y B, Ahn C-H and Kim D J: Metabolism, mechanism of action and sensitivity profile of fluorocyclopentenylcytosine (RX-3117). *Invest New Drugs* 31:1444-57, 2013). In the cell RX-3117 is phosphorylated by uridine/cytidine kinase 2 (UCK2) to its monophosphate form, i.e., RX-3117 is activated by UCK2 to RX-3117 MP. RX-3117 tri-phosphate (RX-3117 TP) is incorporated into the RNA. Its RX-3117 di-phosphate (RX-3117 DP) is reduced to deoxy-di-phosphate (dRX-3117 DP) by ribonucleotide reductase (RR) before the incorporation into the DNA. RX-3117 is a poor substrate for cytidine deaminase (CDA) (id.). Potent tumor growth inhibition by RX-3117 in gemcitabine resistant mouse models was recently demonstrated (Yang M Y, Lee Y B, Ahn C-H, Kaye J, Fine T, Kashi R, Ohne O, Smid K, Peters G J and Kim D J: A novel cytidine analog, RX-3117, shows potent efficacy in xenograft models, even in tumors that are resistant to gemcitabine. *Anticancer Res* 34: 6951-9, 2014). A radiosensitizing effect of RX-3117 has been investigated and results shown below.

RX-3117 is categorized as a pyrimidine analog (Peters G J: Novel developments in the use of antimetabolites. *Nucleosides Nucleotides Nucleic Acids* 33: 358-74, 2014), similar to other analogs such as gemcitabine and azacytidine, which are extensively being used in the clinic. Gemcitabine is a potent radiosensitizer, which increases ionization induced DNA damage repair (Morgan M a, Parsels L a, Maybaum J and Lawrence T S: Improving gemcitabine-mediated radiosensitization using molecularly targeted therapy: a review. *Clin Cancer Res* 14: 6744-50, 2008).

In addition, the cytidine analogs 5-azacytidine (aza-C, Vidaza™) and 5-aza-2'-deoxycytidine (decitabine, Dacogen®) are being used in the clinic for treatment of myelodysplastic syndrome (MDS) (Peters G J: Novel developments in the use of antimetabolites. *Nucleosides Nucleotides Nucleic Acids* 33: 358-74, 2014). Two main mechanisms of anti-tumor effect of these drugs are DNA methyltransferase (DNMT) inhibition and cytotoxic incorporation in RNA and/or DNA (Kaminskas E, Farrell A, Abraham S, Baird A, Hsieh L-S, Lee S-L, Leighton J K, Patel H, Rahman A, Sridhara R, Wang Y-C and Pazdur R: Approval summary: azacitidine for treatment of myelodysplastic syndrome subtypes. *Clin Cancer Res* 11: 3604-8, 2005). After uptake into the cells, aza-C is phosphorylated to 5-azacytidine monophosphate (aza-CMP) by UCK2 and to aza-CDP and aza-CTP by pyrimidine nucleotide kinases. However, aza-C is inactivated by deamination by CDA. RR reduces aza-CDP to aza-dCDP, which is phosphorylated by nucleoside diphosphate kinase to aza-dCTP. Aza-dCTP is then incorporated into DNA, resulting in DNA synthesis inhibition (Veselý J: Mode of action and effects of 5-azacytidine and of its derivatives in eukaryotic cells. *Pharmacol Ther* 28: 227-35, 1985). Stoichiometric binding of aza-dCTP with DNMT will result in DNA hypomethylation (Jones P A: Effects of 5-azacytidine and its 2'-deoxyderivative on cell differentiation and DNA methylation. *Pharmacol Ther* 28: 17-27, 1985). Aza-dCTP can also be formed from 5-aza-2'-deoxycytidine by direct phosphorylation catalyzed by deoxycytidine kinase (dCK) and nucleotide kinases. DNA hypermethylation at CpG islands has been described in different malignancies including MDS (Kaminskas E, Farrell A, Abraham S, Baird A, Hsieh L-S, Lee S-L, Leighton J K, Patel H, Rahman A, Sridhara R, Wang Y-C and Pazdur R: Approval summary: azacitidine for treatment of myelodysplastic syndrome subtypes. *Clin Cancer Res* 11: 3604-8, 2005). On the other hand, aza-CTP incorporates into RNA disrupting metabolism of cytoplasmic and nuclear RNA protein synthesis (Glover A B and Leyland-Jones B: Biochemistry of azacitidine: a review. *Cancer Treat Rep* 71: 959-64, 1987). One mechanism of resistance to azacytidine is a point mutation in the UCK2 gene, which results in an inactive metabolite (Sripayap P, Nagai T, Uesawa M, Kobayashi H, Tsukahara T, Ohmine K, Muroi K and Ozawa K: Mechanisms of resistance to azacitidine in human leukemia cell lines. *Exp Hematol* 42: 294-306.e2, 2014). The mechanism underlying resistance to aza-dCTP is a deficiency of dCK (Peters G J: Novel developments in the use of antimetabolites. *Nucleosides Nucleotides Nucleic Acids* 33: 358-74, 2014).

As shown in FIG. 22, RX-3117 can also down-regulate DNMT1 (Peters G J, Smid K, Vecchi L, Kathmann I, Sarkisjan D, Honeywell R J, Losekoot N, Ohne O, Orbach A, Blaugrund E, Jeong L S, Lee Y B, Ahn C-H and Kim D J: Metabolism, mechanism of action and sensitivity profile of fluorocyclopentenylcytosine (RX-3117). *Invest New Drugs* 31:1444-57, 2013), but seems to act differently than aza-C. Furthermore, several cytidine analogs, but not all, show a radiosensitizing effect. Therefore, the potential radiosensitizing effects as well as the potential mechanisms, such as cell cycle effects and cell killing, of RX-3117 were evaluated. RX-3117 was accordingly shown to have a radiosensitizing effect.

Pre-incubation with RX-3117 had the best radiosensitizing effect and 4 of the 5 cell lines tested were sensitized by RX-3117. The gemcitabine resistant SW1573/G- was sensitized by RX-3117 with almost the same efficacy as its wild type. RX-3117 also showed a radiosensitizing effect in two spheroid models.

Nucleoside analogs have been shown to enhance irradiation induced cell kill (Shewach D S and Lawrence T S; Antimetabolite radiosensitizers. *J Clin Oncol* 25: 4043-50, 2007.). The radiosensitizing effect is thought to be carried out by targeting deoxyribonucleotide biosynthesis (which are needed for DNA replication) or DNA polymerases (Shewach D S and Lawrence T S: Antimetabolite radiosensitizers. *J Clin Oncol* 25: 4043-50, 2007; Lawrence T S, Blackstock A W and McGinn C: The mechanism of action of radiosensitization of conventional chemotherapeutic agents. *Semin Radiat Oncol* 13: 13-21, 2003). An example of deoxynucleotide pool deregulation is the TS inhibitor 5-fluoro-2'-deoxyuridine (FdUrd). TS inhibitors cause deoxynucleotide pools imbalance resulting in DNA synthesis inhibition and S phase arrest (Hwang H S, Davis T W, Houghton J a and Kinsella T J: Radiosensitivity of thymidylate synthase-deficient human tumor cells is affected by progression through the G1 restriction point into S-phase: implications for fluoropyrimidine radiosensitization. *Cancer Res* 60: 92-100, 2000). Imbalance in deoxynucleotide pools causes incorporation of incorrect nucleotides (Ingraham H A, Tseng B Y and Goulian M: Nucleotide levels and incorporation of 5-fluorouracil and uracil into DNA of cells treated with 5-fluorodeoxyuridine. *Mol Pharmacol* 21: 211-6, 1982). The concentration that is needed for radiosensitizing effect to be achieved is not necessarily the concentration which is needed for cytotoxic effect. Lower concentrations of drugs can establish the radiosensitization (Hwang H S, Davis T W, Houghton J a and Kinsella T J: Radiosensitivity of thymidylate synthase-deficient human tumor cells is affected by progression through the G1 restriction point into S-phase: implications for fluoropyrimidine radiosensitization. *Cancer Res* 60: 92-100, 2000). A low dose of RX-3117 induced radiosensitizing effect in the clonogenic assay, in the 3-dimensional model and fractionated irradiation schedule. Also, the double strand DNA breaks induced by RX-3117 were dose dependent.

RX-3117 has been shown to be a potent schedule dependent radiosensitizer in four out of five cell lines, with potential for clinical application where combination treatment is considered in NSCLC. This combination treatment may apply to other tumor types (such as prostate, skin, head and neck, throat, larynx, breast, brain, colorectal, bone, leukemia, ovarian, and uterine cancer.)

Improvements of the Process for Making RX-3117

U.S. Pat. No. 7,405,214 discloses an 11-step synthesis of RX-3117 from D-ribose. The synthesis uses an expensive catalyst which poses a challenge for implementation in large scale plant production. U.S. Pat. No. 9,150,520 improved the synthesis disclosing a shorter route for the preparation of RX-3117 through (3R,4R,6aR)-tert-butyl-(5-fluoro-2,2-dimethyl-6-trityloxymethyl-4,6a-dihy-dro-3aH-cyclopenta[1,3]dioxol-4-yloxy)-diphenyl-silane (ASM11) to 4-amino-1-(3aS,4S,6aR)-5-fluoro-2,2-dimethyl-6-((trityloxy)methyl)-4,6a-d-ihydro-3aH-cyclopenta[d][1,3]dioxol-4-yl) pyrimidin-2(1H)-one (INT14). However, the prior synthesis of ASM11 to INT14 required the intermediates to be isolated in each step. Thus, the process poses cost and time constraints, particularly if scaled up for commercial manufacturing.

The present invention provides an improved process of preparing RX-3117, which is commercially viable for large scale production. The process telescope the synthesis of ASM11 to INT14 without the requirement of isolating each of the intermediate materials, thereby reducing cost while improving efficiency. More specifically, the current invention provides a continuous process with three stages to telescope the synthesis of ASM11 to INT14. The present invention also provides a process to afford RX-3117 monohydrate (RX-3117-MH) in fixed vessels to significantly reduce the cost of manufacture. By telescoping three steps into a single step, the present process removes the requirement to concentrate an intermediate to a residue. These improvements are based on unexpected benefits when substituting reagents that are not readily apparent to person skilled in the art.

Furthermore, the present invention provides optimized reaction and isolation conditions to increase the nitrogen to oxygen (N/O) selectivity at Stage 3, where cytosine is added to (3aR,4R,6aR)-5-fluoro-2,2-dimethyl-6-((trityloxy) methyl)-4,6a-dihydro-3aH-cyclopenta[d][1,3]dioxol-4-yl methanesulfonate (INT13) to make INT14. In the improved process, the ratio of the N- to O-isomers was improved to 99.03:0.97 from the previously optimized value of 88:12. The fixed vessel manufacturing process of the present invention achieves the cost benefits of operation of a scaled-up manufacturing of the desired product in monohydrate form.

Scheme 1 below illustrates an improved process for preparing RX-3117MH.

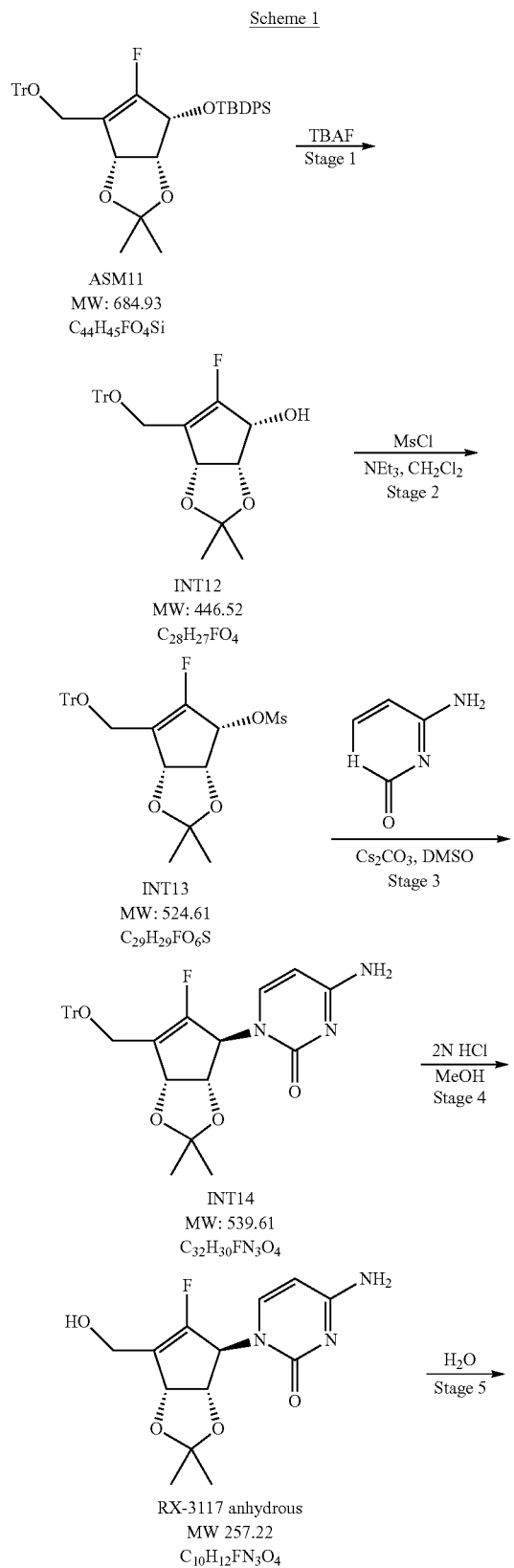

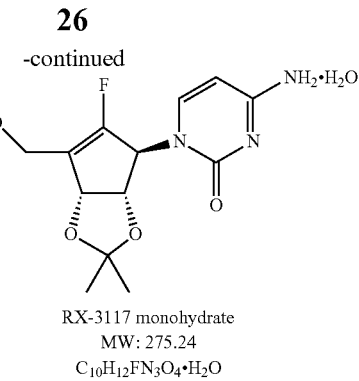

RX-3117 monohydrate
MW: 275.24
$C_{10}H_{12}FN_3O_4 \cdot H_2O$

Stage 1—Process Improvements for Deprotection of ASM11 to Form INT12

In Stage 1 of the process, 2-methyl-tetrahydrofuran was used as the process solvent. This modification allows a work-up to be performed without the need to concentrate the intermediate (3aS,4R,6aR)-5-fluoro-2,2-dimethyl-6-((trityloxy)methyl)-4,6a-dihydro-3aH-cyclopenta[d][1,3]dioxol-4-ol (INT12) and avoid the solvent exchange of the intermediate into methyl tert-butyl ether (MTBE), which was used in the prior process.

In addition, the reaction in-process control (IPC) was changed from using TLC to quantitative $^1$H NMR method. The process was further optimized by using azeotropic removal of water instead of chemical drying. The use of 2-methyl-tetrahydrofuran as the process solvent allowed INT12 in solution to be used directly in Stage 2 of the process without further isolation or purification.

Stage 2—Process Improvements for Mesylation of INT12 to Form INT13

The solution of INT12 in 2-methyl-tetrahydrofuran was telescoped directly into Stage 2 to prepare (3aR,4R,6aR)-5-fluoro-2,2-dimethyl-6-((trityloxy)methyl)-4,6a-dihydro-3aH-cyclopenta[d][1,3]dioxol-4-yl methanesulfonate (INT13). This improved process eliminated the use of the environmentally undesirable dichloromethane as the reaction solvent. Furthermore, the process used an ammonium chloride wash to further control residual triethyl amine. The work up volumes were reduced to a maximum process volume at 12.5 vol., a reduction from 14 volumes. Again, the process was further optimized by using azeotropic removal of water instead of chemical drying. The use of 2-methyl-tetrahydrofuran as the process solvent allowed INT13 in solution to be used directly in Stage 3 of the process.

Stage 3—Process Improvements for the Addition of Cytosine to INT13 to Form INT14

The solution of INT13 in 2-methyl-tetrahydrofuran was telescoped directly into Stage 3 to make INT14. Dimethyl sulfoxide (DMSO) was retained as the reaction solvent and the removal of 2-methyl-tetrahydrofuran was performed by distillation. A specification of 27% w/w of 2-methyl-tetrahydrofuran versus product was found to allow the stage 3 reaction to perform well. The inventors conducted a screening of bases (inorganic and amine) and found that cesium carbonate offered the highest chemo-selectivity and most rapid reaction rate. The inventors also conducted a screening of reaction solvents and found DMSO to be the most suitable solvent for the reaction.

Furthermore, the inventors studied the impact of reagent charges, temperature and concentration on the selectivity of the N- vs O-isomers of INT14. In accordance with the improved process of the present invention, the ratio of the N- to O-isomers was improved to 99.03:0.97 using solvent extraction and recrystallization/precipitation from the previously optimized 88:12, which was isolated using SiO$_2$ column chromatography. The inventive process eliminates the need of column chromatography and also provides the desired N-isomers at over 99%. In particular, the inventors found that chemoselectivity was effected primarily by the reaction temperature. In particular, lowering the reaction temperature slowed the rate of conversion to product. The reaction condition was further improved by increasing the charging of base and cytosine from 2.0 equivalents to 2.5 equivalents. The reaction temperature was reduced from 40° C. to 35° C. In addition, the work up procedure was modified to reduce the total process volume from 22 vol to 12.5 vol to improve throughput. The work up solvent was changed from ethyl acetate to isopropyl acetate to allow the reaction mixture to move directly into isolation without the requirement to exchange solvent. The work up procedure was also modified to start with the tautomerization as it was found that INT14 was more soluble following the acetic acid treatment. The isolation of INT14 was modified to initially precipitate the product from isopropyl acetate at high volume prior to reducing the volume and adding n-heptane. This improvement was found to prevent oiling and adherence to the vessel prior to isolation. Thus, an overall improved synthesis with increased selectivity was achieved by simultaneously changing multiple reaction parameters. The modification of temperature and concentration were found to have a positive impact on rate of conversion and chemoselectivity of the N/O alkylation.

Stage 4—Process for Deprotecting INT14 to Form RX-3117 Anhydrous

The original conditions of 2 M HCl in ethanol were found to be the most stable for the product and were retained. However, the process was improved by reducing the reaction temperature from 60° C. to 50° C. to aid solubility. The trityl alcohol by-product was removed using methyl tert-butyl ether (MTBE) washes. The product in the aqueous phase was telescoped directly into the Stage 5 isolation following the resin salt release.

Stage 5—Process for Isolating RX-3117 Monohydrate

The solution of RX-3117MH was telescoped directly into Stage 5. The combined Stage 4 and Stage 5 with minor modifications to the procedure optimized yield and operability on scale. The RX-3117-MH was dried on a filter under air, which controlled acetonitrile quantities to below the ICH guideline while retaining the water content. This improved process removed the time-demanding requirement to first dry and then re-hydrate the product to afford a crystalline product. The isolated product using the improved process has a purity of (99.83%), which was comparable in purity with the custom synthesis of the product in small quantities.

Other Improvements of the Process for Making Starting Materials of RX-3117

Other process improvements for the synthesis of the starting materials of RX-3117 are possible, Synthesie of ASM11 using different intermediates and protecting groups are shown below in Schemes 2 and 3, respectively.

Synthesis of ASM11 by Bromo Intermediates

Scheme 2

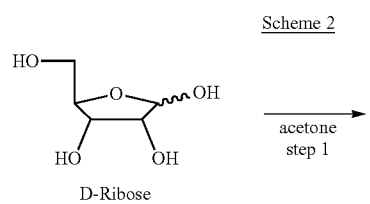

D-Ribose acetone
step 1

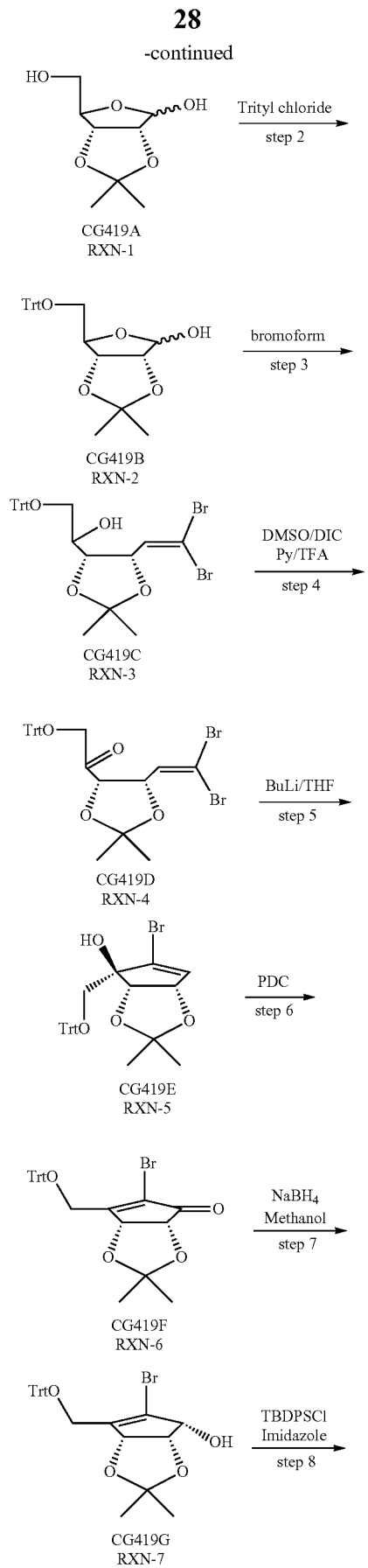

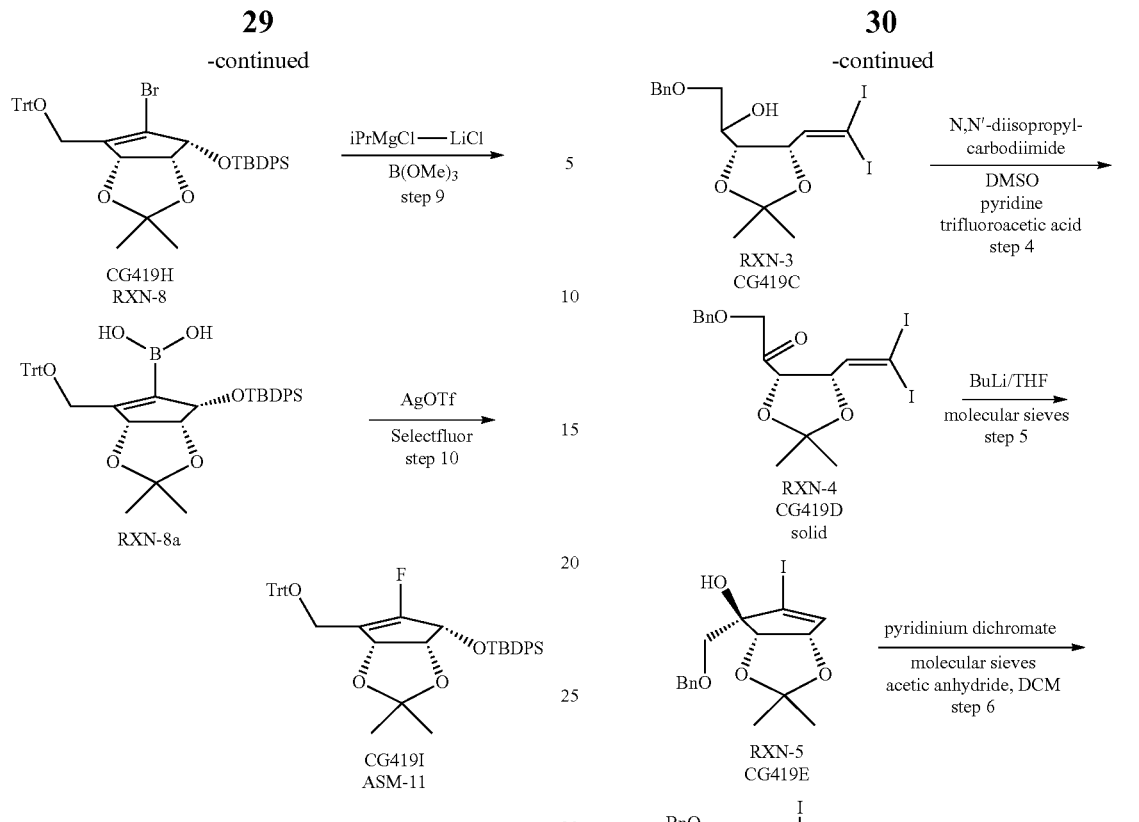

In U.S. Pat. No. 9,150,520, iodoform was used in step 3 of the reaction to convert RXN-2 to RXN-3. In the present invention, the use of bromoform or a mixed bromo-iodomethane to affords bromointermediates instead of iodointermediates. The bormointermediates can be more stable than their iodo derivate. Therefore, the overall yield and purity can increase as a result.

Synthesis of ASM11Bn by Benzyl Protection of 5-Hydroxyl Group

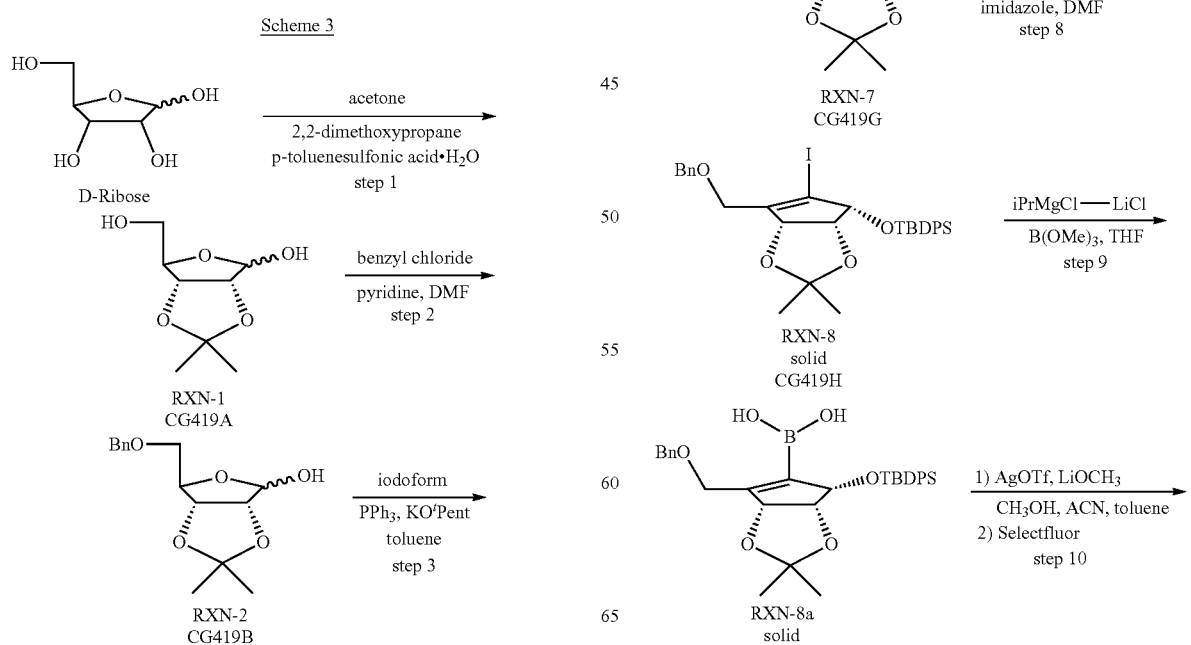

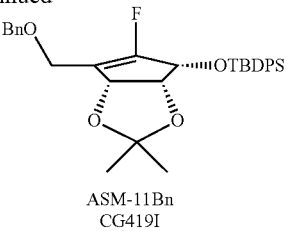

Unexpectedly, changes in protecting groups placed in early intermediates can have dramatic effects on reaction steps conducted later in the process, without requiring modification of numerous steps along the way. For example, changing the trityl protecting group to benzyl in Step 2 could improve the yield on the fluorination in Step 10 of the reaction. These improvements can be made without further modification of the overall procedure.

Synthesis of ASM11 by Ring Closing Metathesis

The inventors of the present invention also developed schemes for the synthesis of ASM11 by the employment of ring closing metathesis. In Scheme 4, a ring closing metathesis reaction is used to form the 5-member ring moiety. Ruthenium of the Grubb's catalyst is recoverable, further improving scale up processes by reducing waste and cost.

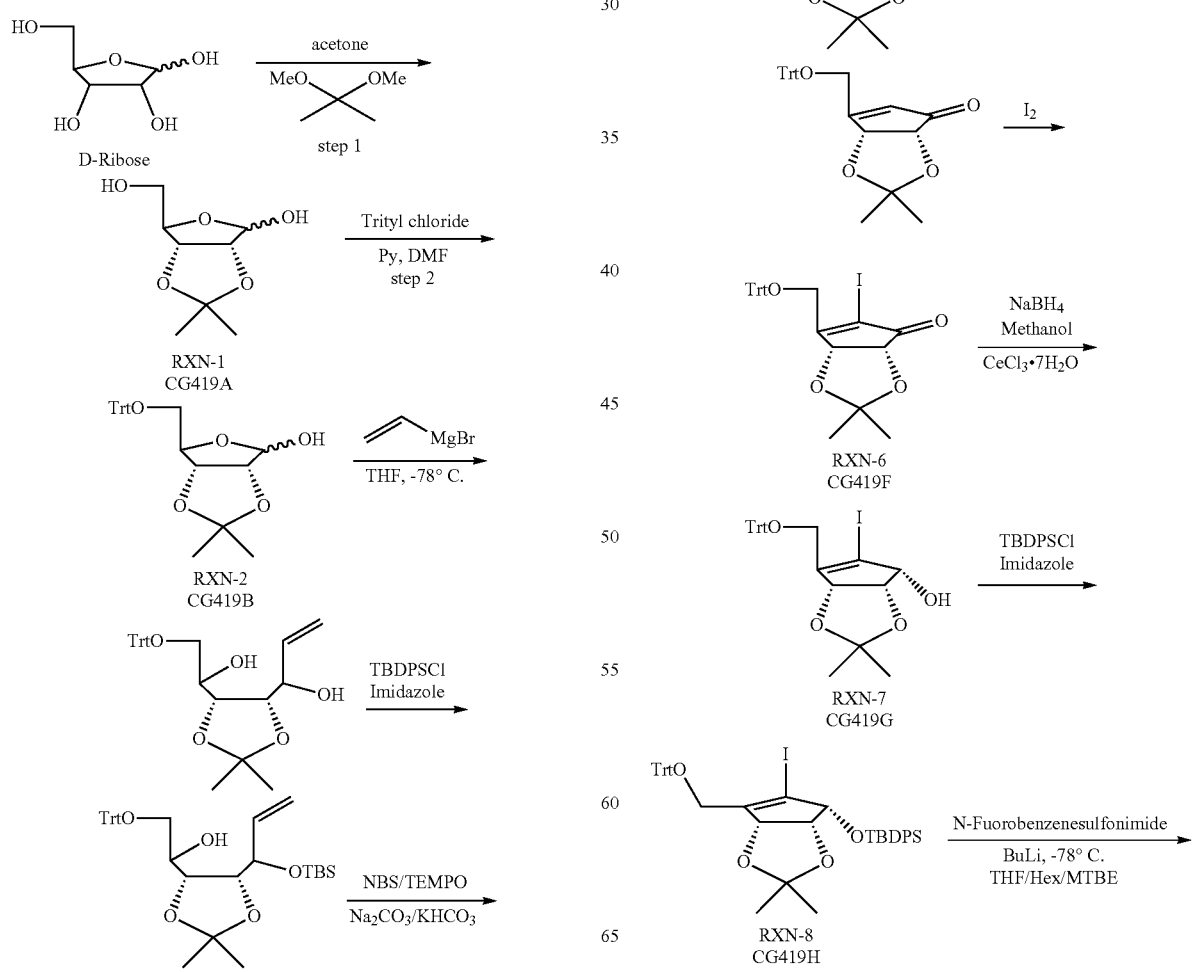

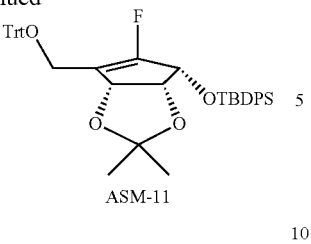

ASM-11

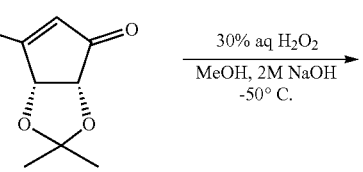

Scheme 6

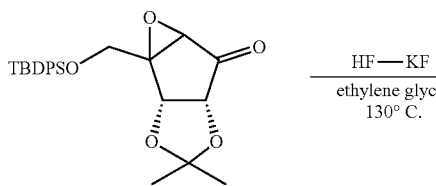

Synthesis of Intermediate RXN-6 by Ring Closing Metathesis

The synthesis of intermediate RXN-6 can be accomplished by ring closing metathesis, including RXN-5 and to introduce the fluorine atom to the five member ring by making a fluorinated RXN-6. As shown in Scheme 5, a ring closing metathesis reaction is used to form the 5-member ring moiety (Fluoro-RXN-6). As in Scheme 4, the ruthenium of the Grubb's catalyst is recoverable.

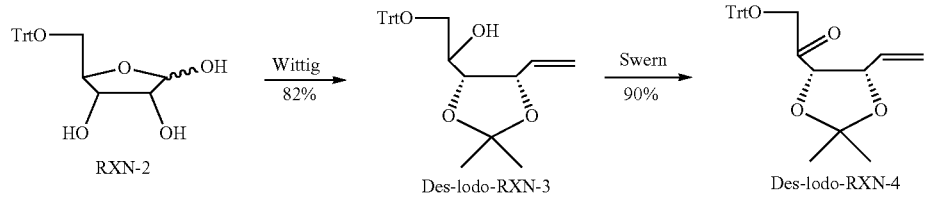

Scheme 5

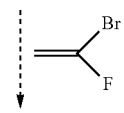

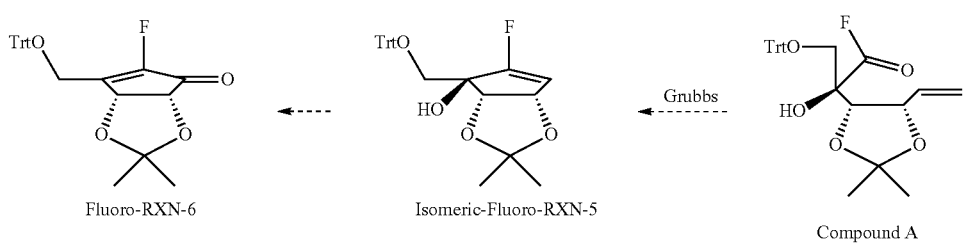

Synthesis of Intermediate RXN-6 by Nucleophilic Fluorination Via an Epoxide

The synthesis of intermediate RXN-6 by an alternative nucleophilic fluorination via an epoxide can be provided. Scheme 6 shows the formation of an epoxide ring from the starting material (3aR,6aR)-6-(((tert-butyldiphenylsilyl) oxy)methyl)-2,2-dimethyl-3a,6a-dihydro-4H-cyclopenta[d] [1,3]dioxol-4-one. The epoxide is opened by nucleophilic fluorination using, for example, potassium fluoride. As an alternative, other fluoride source, for example, tetrabutylammonium fluoride, can also be used to open the epoxide ring. The elimination of water is a difficult step in this process and alternative dehydrating agents, such as, for example, carbomethoxy sulfamoyl triethylammonium salts, can be used to arrive at the modified intermediate Flouro-RXN6-TB-DPS.

-continued

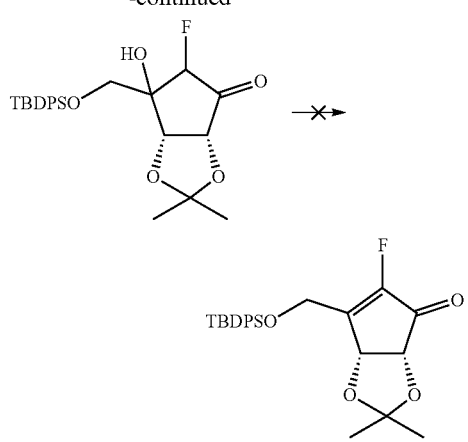

Synthesis of Intermediate RXN6 by Aldol Condensation

The synthesis of intermediate RXN6 can also be accomplished using Aldol Condensation to introduce a fluorine atom to the five member ring by making a fluorinated RXN-6. As shown in scheme 7, the fluorine atom is introduced early on to form the fluorinated derivative of RXN6 (Fluoro-RXN6). An internal Aldol Condensation can form the 5-membered ring with the vinyl fluorine moiety in place.

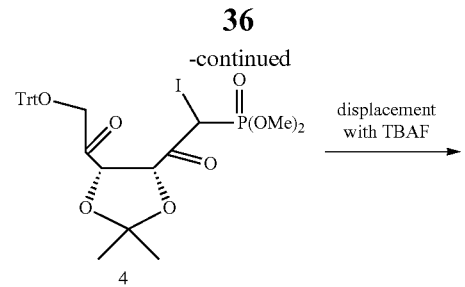

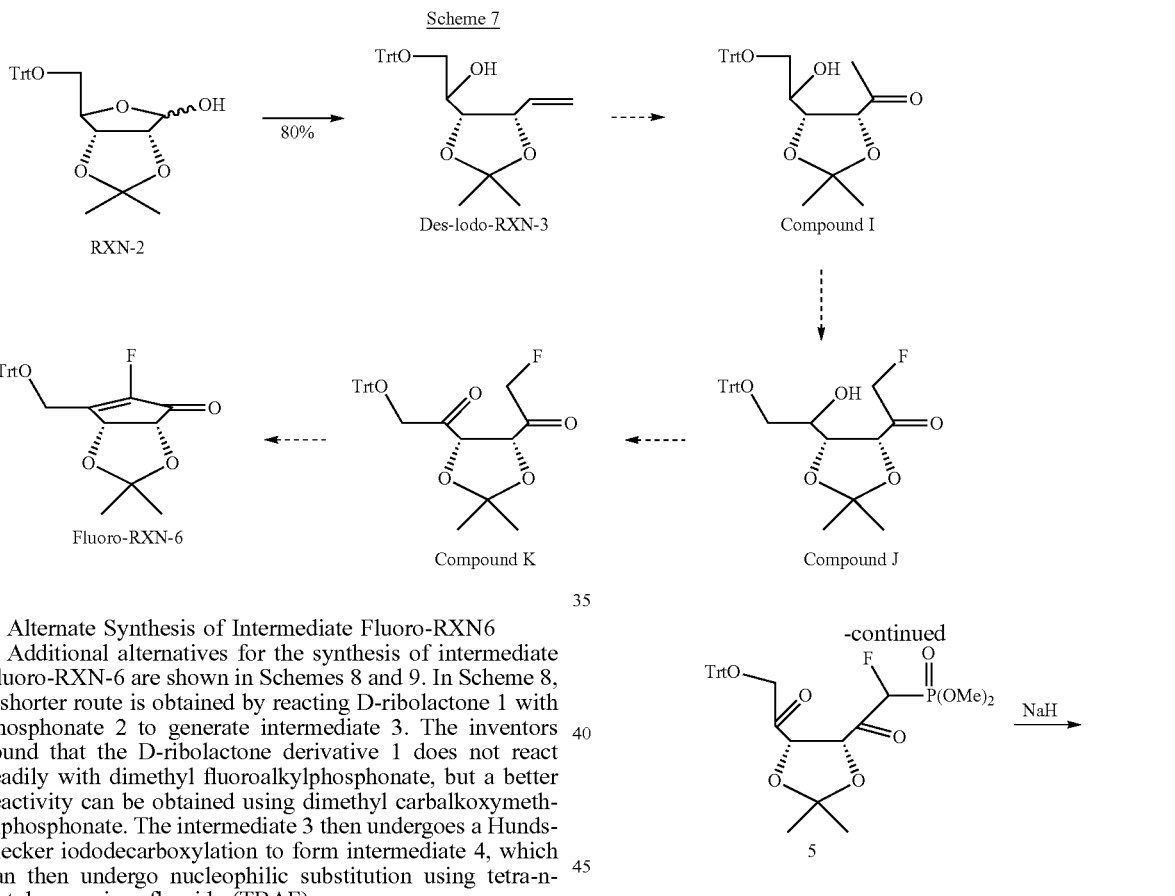

Alternate Synthesis of Intermediate Fluoro-RXN6

Additional alternatives for the synthesis of intermediate Fluoro-RXN-6 are shown in Schemes 8 and 9. In Scheme 8, a shorter route is obtained by reacting D-ribolactone 1 with phosphonate 2 to generate intermediate 3. The inventors found that the D-ribolactone derivative 1 does not react readily with dimethyl fluoroalkylphosphonate, but a better reactivity can be obtained using dimethyl carbalkoxymethylphosphonate. The intermediate 3 then undergoes a Hundsdiecker iododecarboxylation to form intermediate 4, which can then undergo nucleophilic substitution using tetra-n-butylammonium fluoride (TBAF).

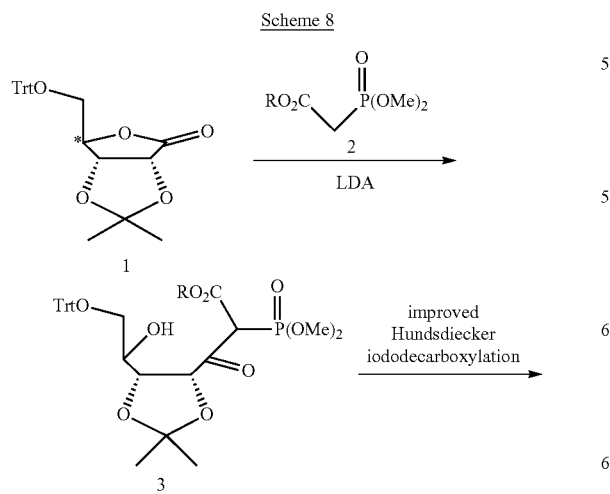

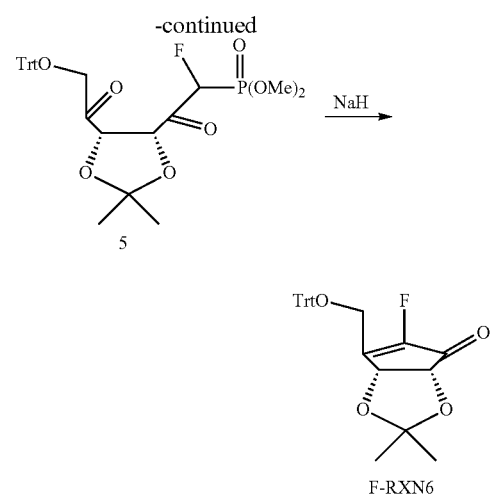

Scheme 9 (below) provides an even shorter route by reacting D-ribolactone 1 with an alkyl phenyl sulfone 7, which is prepared via electrophilic fluorinated-reagents, to form intermediate 8. The D-ribolactone derivative reacts more readily with lithio fluoroalkyl sulfone 7 than with fluoroalkylphosphonates. The intermediate 8 can be converted to intermediate 9, which will undergo elimination to form F-RXN6. Alternatively, a more efficient but more expensive option is to use a fluorinated-tetrazolyl sulfone 10 in place of lithio fluoroalkyl sulfone 7.

Scheme 9
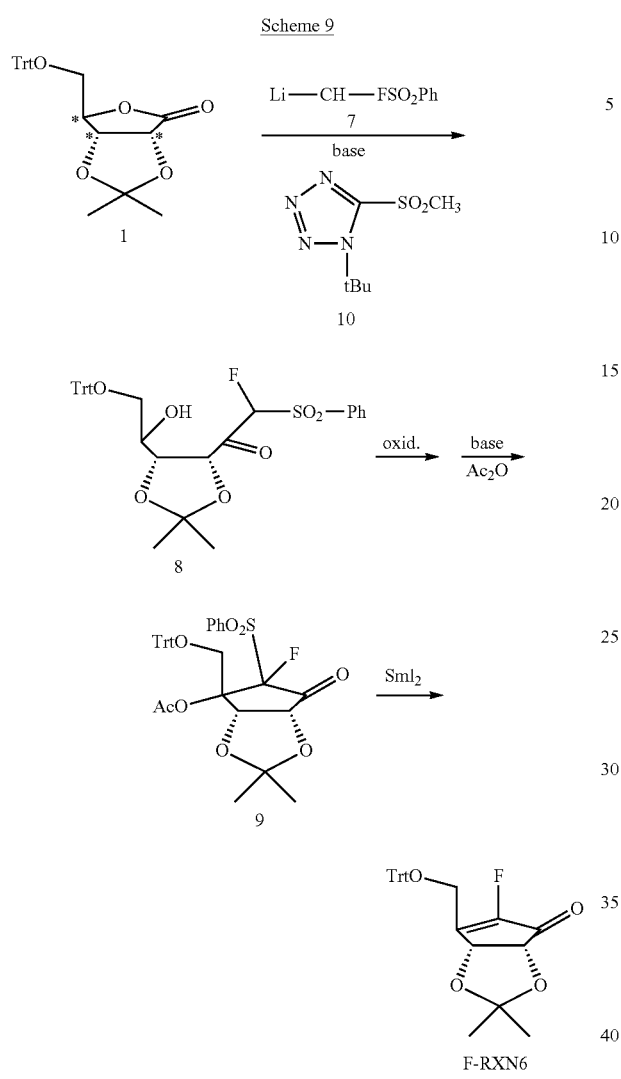
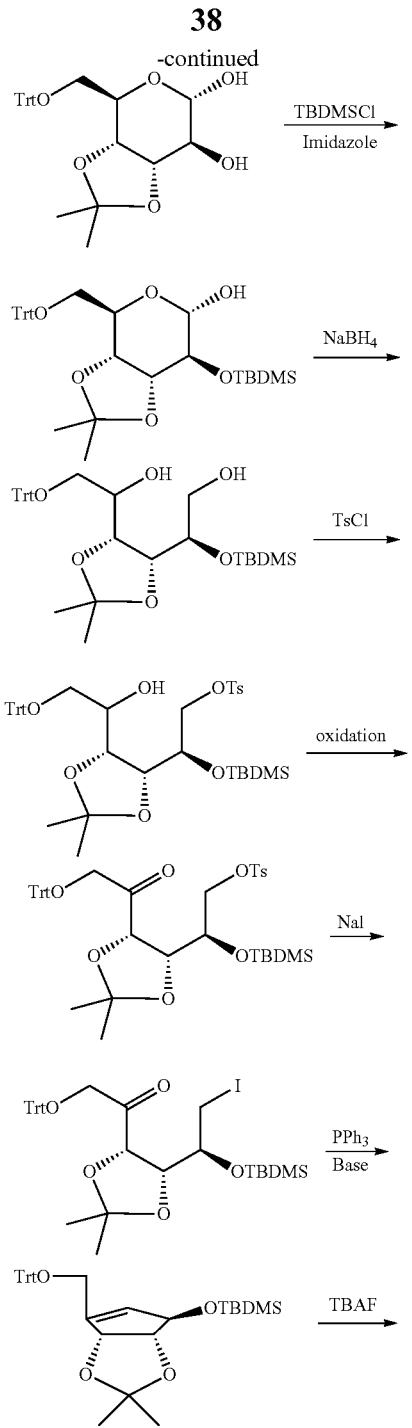
Synthesis Using Different Chiral Sources
The present synthesis can also be achieved by using different chiral sources as starting materials.
In Scheme 10 (below), (2S,3S,4R,5S,6R)-6-(hydroxymethyl)tetrahydro-2H-pyran-2,3,4,5-tetraol is used as an alternative chiral starting material to generate ASM-11.
Scheme 10
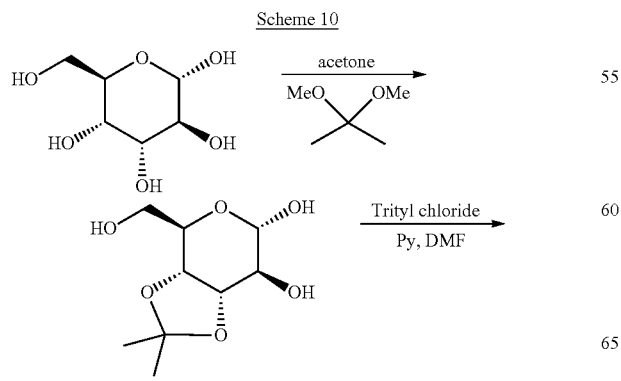
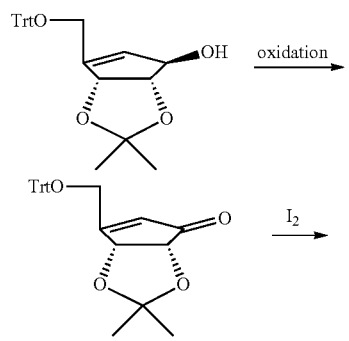

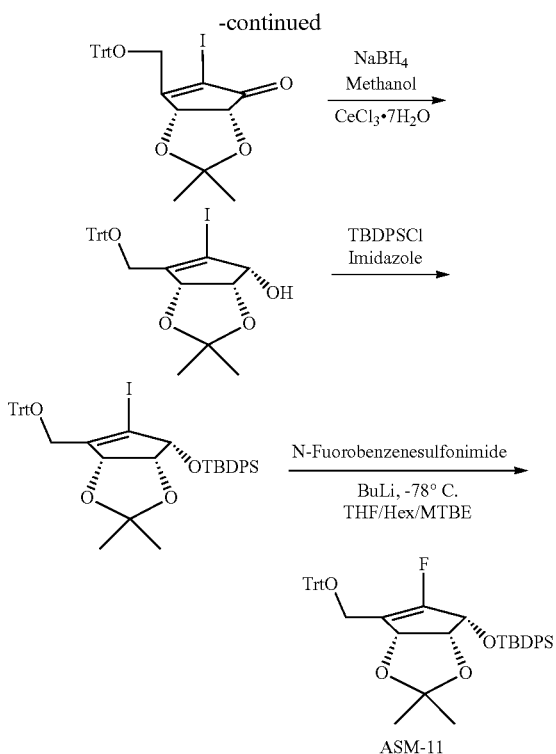

ASM-11

EXAMPLES

The following examples are presented for illustrative purposes and should not serve to limit the scope of the disclosed subject matter.

$IC_{50}$ values for cell-lines A549, SW1573, and SW1573/G used herein are 8.3 μM, 13.7 μM and 7.3 μM, respectively, as reported in Peters et al., "Metabolism, mechanism of action and sensitivity profile of fluorocyclopentenylcytosine (RX-3117)," Investigational New Drugs, December 2013, Vol. 31, No. 6, pp. 1444-1457 (available online at http://link.springer.com/article/10.1007/s10637-013-0025-x).

Example 1: Effect of RX-3117 on Non-Small Cell Lung Cancer Cell Lines

The effect of RX-3117 on cell cycle regulation and cell death in human non-small cell lung cancer (NSCLC) cell lines A549 (adenocarcinoma), SW1573 (alveolar carcinoma) and SW1573/G- (SW1573 cell line resistant to gemcitabine) and H460 (large cell carcinoma) was assessed. The A549 and H460 cell lines were obtained from American Type Culture Collection (Manassas, Va., USA). The SW1573 cell line, obtained from Dr. Johan van Rijn (see Keiser et al., Cancer Research, 49:2988-2993 (1989)), also served as the parental cell line for SW1573/G-. A549, SW1573, and SW1573/G- and H460 were kept in exponential growth in T25 flasks (Greiner Bio-One GmbH, Frickenhausen, Germany) and cultured in Dulbecco's minimal essential medium (DMEM) or RPMI 1640 (A549) supplemented with 10% heat-inactivated fetal bovine serum (FBS) 1% streptomycin and penicillin 20 mM HEPES and maintained in 37° C. water saturated atmospheres of 5% $CO_2$. For the cell cycle distribution, $1.5 \times 10^5$ cells were seeded in a T25 flask (Greiner Bio-One GmbH) and cultured for 72 hours after which 1 μM of RX-3117 was added and incubated for 24 hours. The cells were then harvested. After the treatment, the medium was collected in a 15 ml tube (Greiner Bio-One GmbH). The cells were washed with ice cold PBS and trypsinized (Lonza) at 37° C. The collected medium was used to inactivate trypsin of the corresponding sample and again collected in the 15 ml tube. The cells were centrifuged with the standard centrifuge program, 5 minutes at 4° C. and 12,000 rpm. The medium was removed, pellet washed with 1 ml PBS/0.01% BSA and centrifuged. After removal of the supernatant, the cells were fixed with 1 ml 70% ethanol and incubated at -20° C. for at least 24 hours. Subsequently, the cells were centrifuged, washed with 1 ml PBS/0.1% BSA and transferred to a FALCON FACS tube (BD, Franklin Lakes, N.J., USA). The cells were centrifuged, and the supernatant was removed followed by the addition of 0.5 μg propidium iodide (PI) (Sigma, St. Louis, Mo., USA), 0.1% trisodium citrate (Riedel-de Haen, Sigma-Aldrich Laborchemikalien GmbH, St. Louis, Mo., USA), 0.1% Triton X-100™ (Merck) and 0.1 mg/ml RNase (Sigma) (PI solution) to the samples. Subsequently, for at least 15 minutes, the cells were incubated on ice with the PI solution to stain the DNA before starting the analysis. The cells stained with the PI solution were analyzed by FACSCalibur™ (BD Biosciences, Mount View, Calif., USA). Data was analyzed with CellQuest™ Pro software.

The mechanism of cell cycle arrest was investigated by measuring cell cycle proteins expression using western blotting. The influence of RX-3117 on protein expression during different treatment conditions was analyzed by western blot. Cells were lysed using cell lysis buffer 1× (Cell Signaling, Danvers, Mass., USA) containing 4% protease inhibitor cocktail (Roche Diagnostics, Mannheim, Germany) on ice for 30 minutes and centrifuged for 10 minutes at 4° C. at 14,000 rpm. The protein containing supernatant was collected and the Bio-Rad assay was performed to determine protein amount as described in Lemos et al., Pharmacogenomics, 12(2):159-70 (2011). The following antibodies were used for protein expression: DNMT1 (Cell Signaling, 1:1000 #5032S), DNMT3A (Cell Signaling 1:1000 #2160S), DNMT3B (Abcam, 1; 1000), Chk2 (Cell Signaling 1:1000 #6334P), Chk1 (Cell Signaling 1:1000), p-CDC25C (Cell Signaling 1:1000 #4901S), Cdk1 (Cell Signaling 1:1000 #9112S), Cdk2 (Cell Signaling 1:1000 #2546S), wee1 (Cell Signaling 1:1000), 5139-γH2A.X (Cell Signaling, 1:1000), β actin (Sigma, 1:10,000), Caspase 9 (Cell Signaling, 1:1000), PARP (Roche 2003, 1:1000), p53 (Cell Signaling, 1:1000, #9282). The antibodies were diluted in 1:1 solution Rockland buffer (Rockland Inc., Philadelphia, Pa., USA) and PBS supplemented with 0.05% Tween® 20. The proteins were separated in 20% SDS-PAGE and transferred to a PVDF membrane. For fluorescent signal secondary antibodies goat anti-mouse InfraRedDye and goat anti-rabbit InfraRedDye were used. The proteins were detected by an Odyssey InfraRed Imager (Li-COR Bioscience, Lincoln, Nebr., USA).

Figure 2:
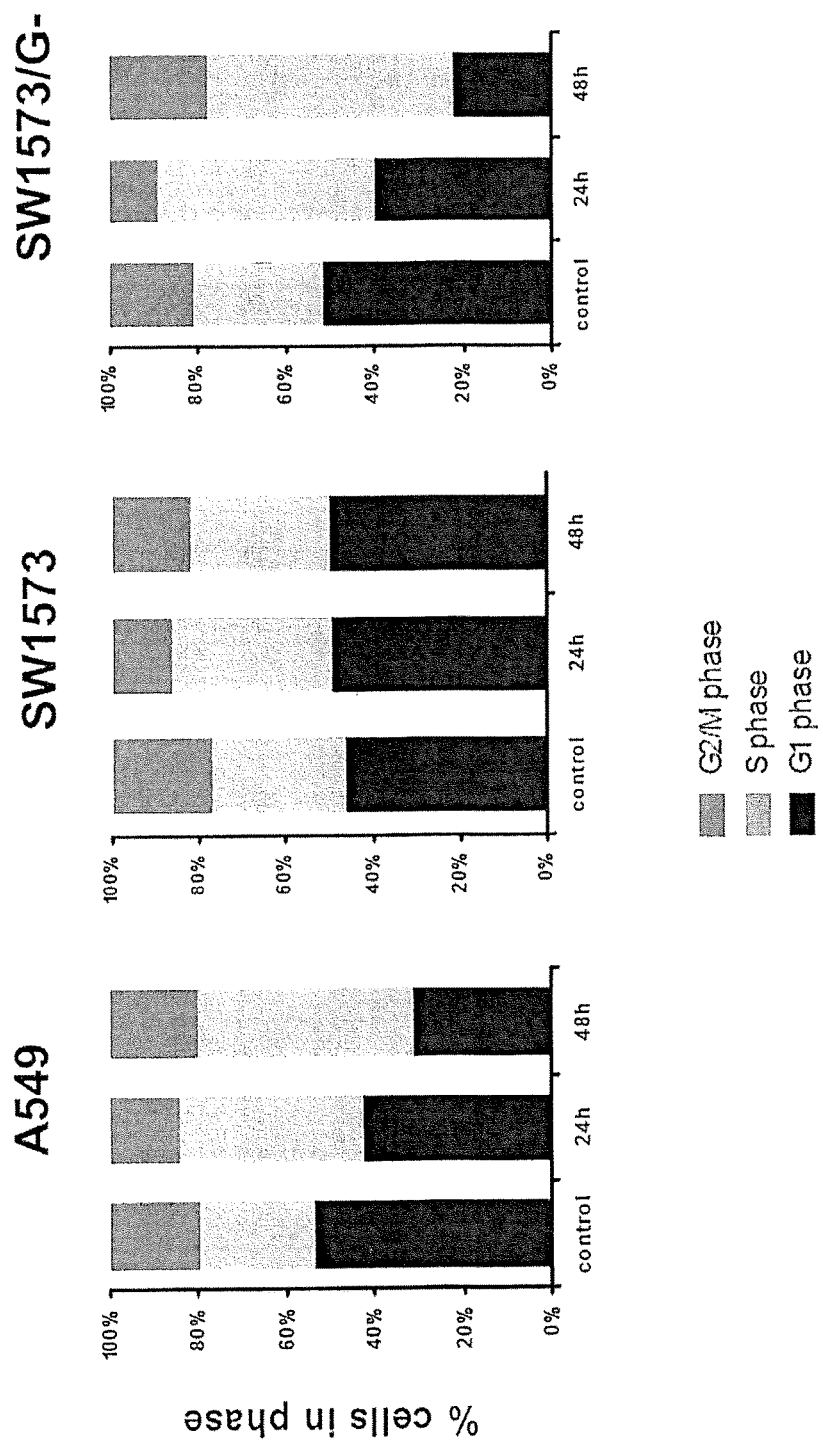
FIG. 2 is a series of bar graphs showing the effect of RX-3117 (5×IC$_{50}$) on A549, SW1573 and SW1573/G-cells in the S-phase after 24 hours and 48 hours. At a higher dose of 5×IC$_{50}$, RX-3117 induced the accumulation of A549, SW1573 and SW1573/G-cells in the S-phase.

Abbreviations used herein denote the following:
BSA=bovine serum albumin
HEPES=2-[4-(2-hydroxyethyl)piperazin-1-yl]ethanesulfonic acid
PBS=phosphate buffered saline
PVDF=polyvinylidene difluoride
RPM=revolutions per minute
SDS-PAGE=sodium dodecyl sulfate polyacrylamide gel electrophoresis Cell Cycle At a dose of 1 μM, RX-3117 induced accumulation of A549, SW1573, SW1573/G- and H460 cells in the G1 phase after 24 hour exposure (FIG. 1). At a higher dose of 5×IC$_{50}$, RX-3117 induced the accumulation of A549, SW1573 and SW1573/G-cells in the S-phase (FIG. 2).

Caspase Activation

Figure 3:
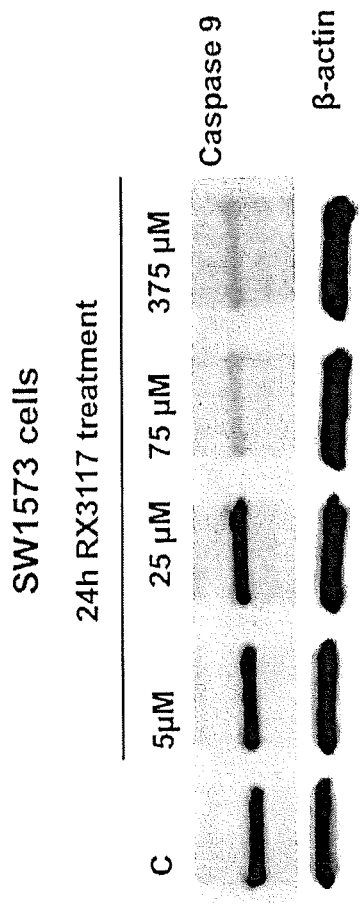
FIG. 3 is a series of western blots showing the effect of increasing concentrations of RX-3117 on pro-caspase 9 activation in SW1573 cells. RX-3117 decreased pro-caspase 9 in SW1573 cells. Reduction of pro-caspase 9 indicates activation of caspase and subsequential apoptosis induction.
Figure 4:
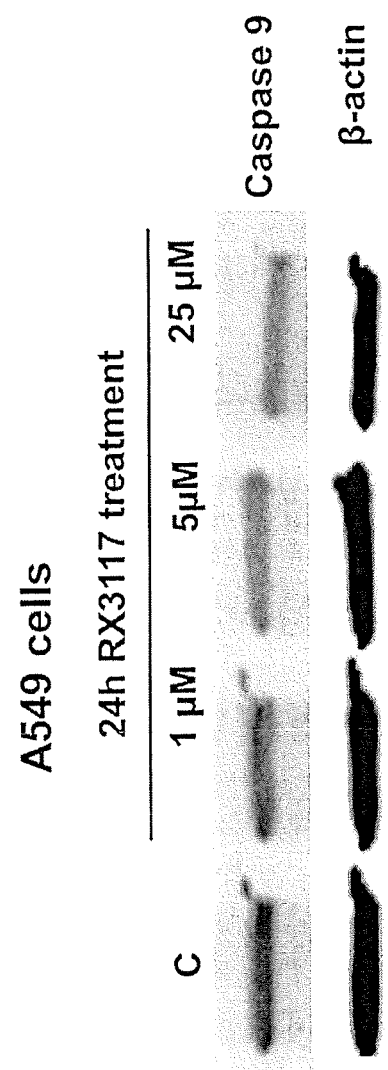
FIG. 4 is a series of western blots showing the effect of increasing concentrations of RX-3117 on pro-caspase 9 activation in A549 cells. RX-3117 decreased pro-caspase 9 in A549 cells.

RX-3117 decreased pro-caspase 9 in SW1573 cells and A549 cells after 24 hour exposure to increasing concentrations of RX-3117. Reduction of pro-caspase 9 indicates activation of caspase and subsequential apoptosis induction (FIGS. 3 and 4).

DNMT Protein

Figure 23:
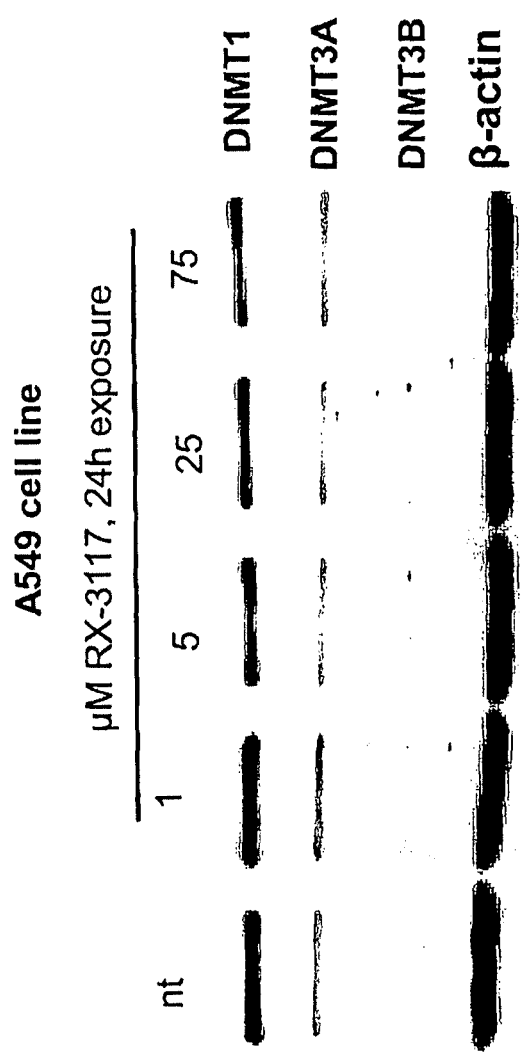
FIG. 23 is a series of western blots showing the effect of RX-3117 at 1 µM, 5 µM, 25 µM, and 75 µM on DNMT1, DNMT3A, DNMT3B, and β-actin expression levels in A549 cells. RX-3117 downregulates maintenance of DNA methyltransferase 1.

RX-3117 down regulates maintenance of DNA methyltransferase 1 (DNMT1) in A549 cells (FIG. 23) at higher dose and increased DNMT3A and DNMT3B expression levels in A549 cells. A proposed mechanism for this down regulation is shown in FIG. 22.

DNA Damage

Figure 5:
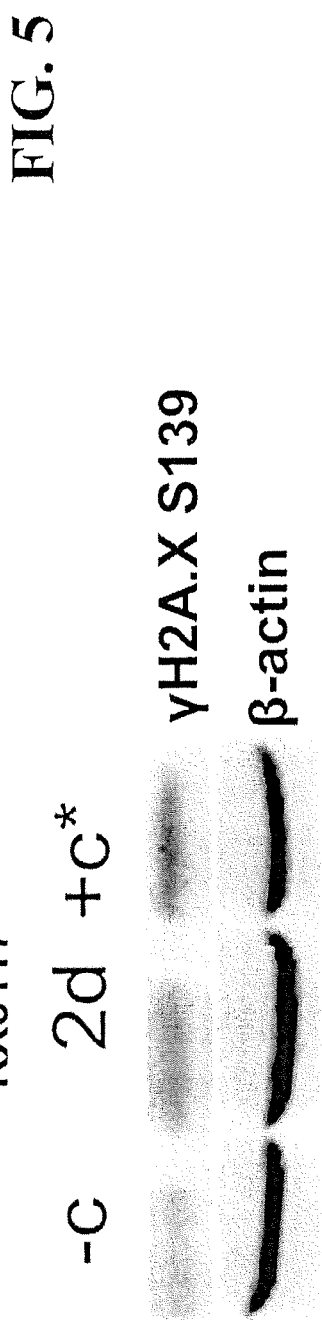
FIG. 5 is a series of western blots showing the double-strand breaks (DSB) induced by RX-3117 as indicated by biomarker γH2A.X (phospho 5139) in SW1573 cells after 48 hours. RX-3117 induces DSB indicated by a marker for DSB phosphor S139 H2A.X after 48 h. C* means DNA damage by 50 μM etoposide after 2 days, which served as a positive control.
Figure 6:
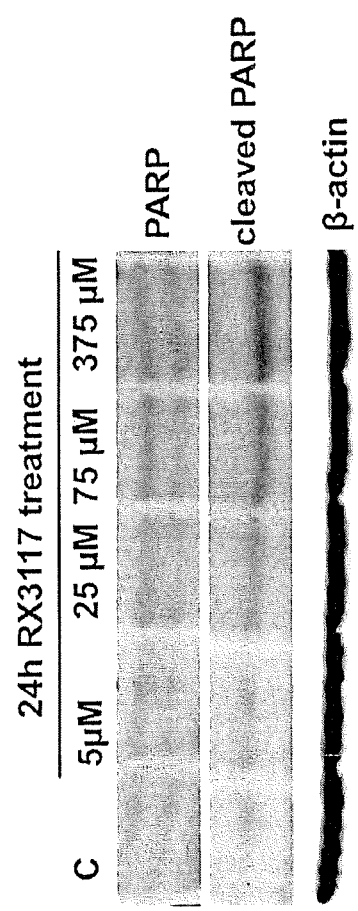
FIG. 6 is a series of western blots showing cleaved PARP induced by increasing concentrations of RX-3117 after 24 hours.
Figure 7:
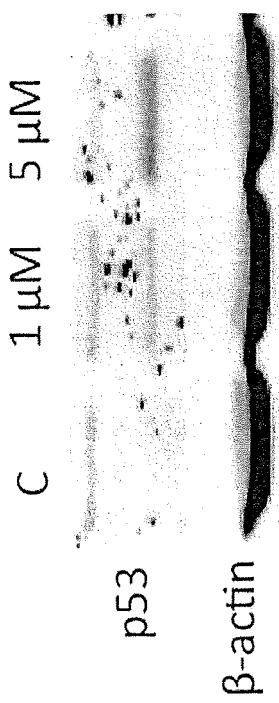
FIG. 7 is a series of western blots showing the effect of RX-3117 at 1 μM and 5 μM on p53 expression levels in A549 cells. At 1 μM and 5 μM, RX-3117 increased p53 expression levels in A549 cell line.
Figure 8:
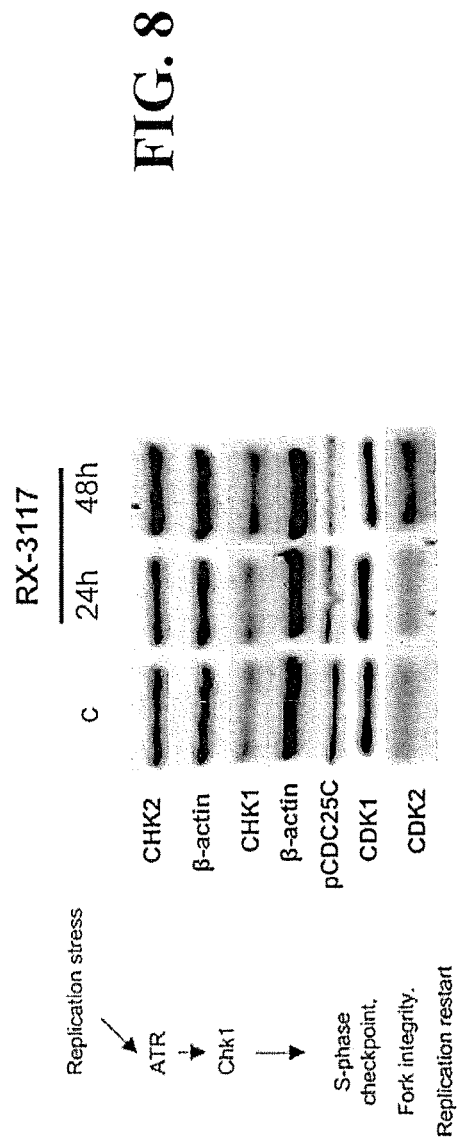
FIG. 8 is a series of western blots showing the effect of RX-3117 at 10 μM on Chk1, Chk2, Cdk1, Cdk2 and p-Cdc25C expression levels in SW1573 cells after 24 and 48 hours. In SW1573 cells Chk1 is increased after 48 h of exposure to 10 μM RX-3117, pCDC25C is decreased and Cdk2 is increased.
Figure 9:
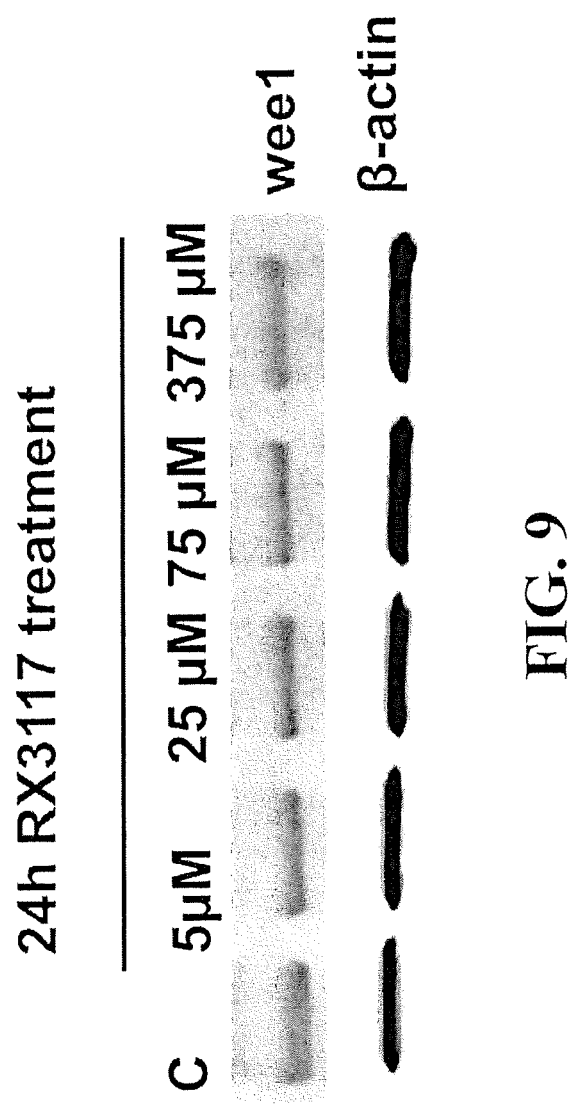
FIG. 9 is a series of western blots showing the effect of increasing concentrations of RX-3117 on wee1 expression levels in SW1573 cells after 24 hours. Increasing concentrations of RX-3117 have an effect on wee1, which is decreased after 24 h in SW1573 cell lines.
Figure 24:
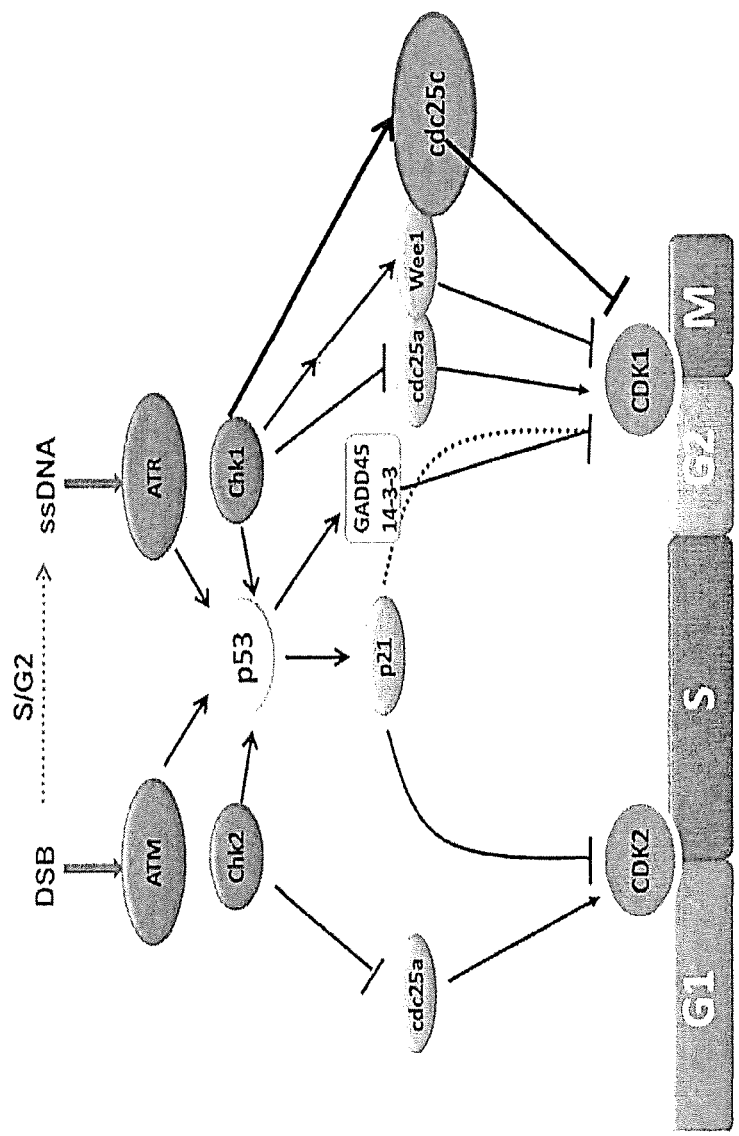
FIG. 24 is a diagram showing the potential effects on cell cycle proteins: regulation of cell cycle by checkpoint kinases Chk1 and Chk2 after damage induction.

RX-3117 induced double-strand breaks (DSB) as indicated by biomarker γH2A.X (phospho 5139) in SW1573 cells after 48 hour exposure (FIG. 5). RX-3117 induced cleaved PARP after 24 hour exposure to increasing concentrations of RX-3117 (FIG. 6). Cleaved PARP indicates activated caspases activity in apoptotic cells. At 1 μM and 5 μM, RX-3117 increased p53 expression levels in A549 cells (FIG. 7). At 10 μM, RX-3117 increased Chk1 and Cdk2 expression levels, while decreasing p-Cdc25C expression levels in SW1573 cells after 48 hour exposure (FIG. 8). DNA damage is induced by RX-3117 triggers the Chk1 pathway. The ATR/Chk1 pathway is induced by DNA replication stress and DSB. RX-3117 decreased wee1 expression levels in SW1573 cells after 24 hour exposure to increasing concentrations of RX-3117 (FIG. 9). FIG. 24 is a diagram showing the potential effects on cell cycle proteins and regulation of the cell cycle by checkpoint kinases Chk1 and Chk2 after damage induction, RX-3117 may have activity along several of these pathways.

Apoptosis Induction

Figure 10:
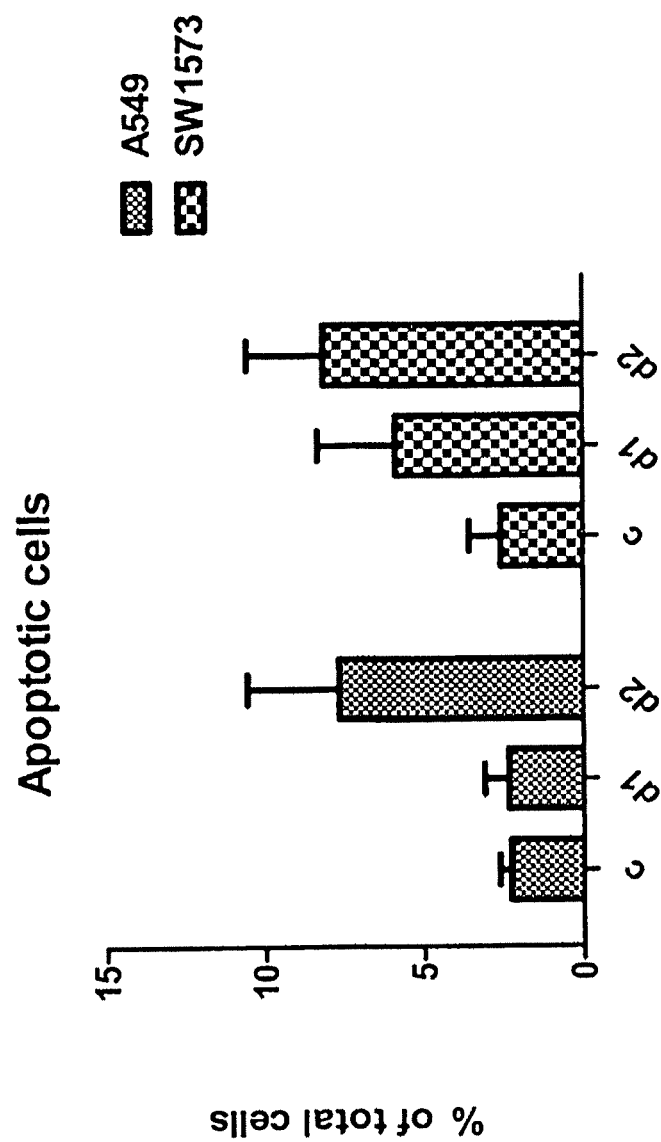
FIG. 10 is a bar graph showing the effect of RX-3117 at 5×IC$_{50}$ on PI stained, apoptotic A549 and SW1573 cells in the sub-G1 phase after 24 hours (d1) and 48 hours (d2).
Figure 11:
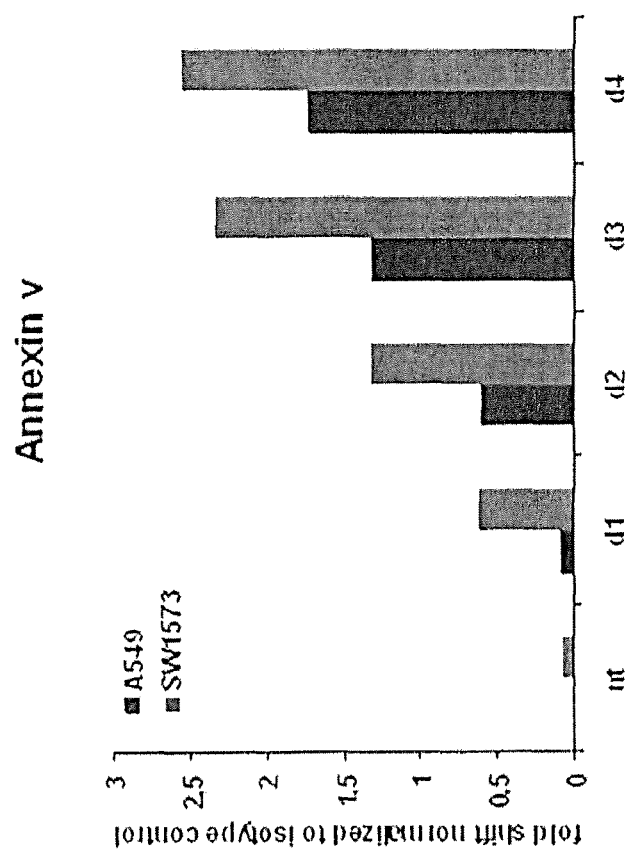
FIG. 11 is a bar graph showing the effect of RX-3117 at 5 μM (for A549) and 10 μM (for SW1573) on Annexin V stained, apoptotic A549 and SW1573 cells in the sub-G1 phase after 24 hours (d1), 48 hours (d2), 72 hours (d3) and 96 hours (d4).

At a dose of 5×IC$_{50}$, RX-3117 induced apoptosis in PI stained A549 and SW1573 cells in the sub-GI phase after 24 and 48 hour exposure (FIG. 10). At 5 μM (for A549) and 10 μM (for SW1573), RX-3117 induced apoptosis in Annexin V stained A549 and SW1573 cells in the sub-GI phase after 24, 48, 72 and 96 hour exposure (FIG. 11).

Results

The results suggest that cell cycle arrest was time, concentration and cell line dependent. In A549, H460 and SW1573 cells, 24 hour exposure to 1 μM RX-3117 increased the accumulation of cells in the G1 phase (about 20-40%) and in the S-phase (to a lesser extent), but decreased the accumulation of cells in the G2/M phase. Thus, low dose of RX-3117 induces G1 accumulation and high dose of RX-3117 induces S phase accumulation. No cell kill was observed at 24 hour exposure, but cell kill was observed at 48 hour exposure (15% in SW1573 and 8% in A549 cells) accompanied by γH2AX induction. In A549 cells, the effect of RX-3117 on the cell cycle distribution was most pronounced at 48 hour exposure with 45% accumulation in S phase. S-phase accumulation is time dependent. Treatment with RX3117 increased p53, Chk1, Chk2 and Cdk2 expression levels, but decreased Cdc25C and p-Cdc25C expression levels. RX-3117 increased wee1 expression levels mostly after 48 hours. RX-3117 appeared to induce apoptosis through SSB and DSB. Cleaved PARP in SW1573 cells indicates upregulated caspase activity in apoptotic cells. Reduction of pro-caspase 9 in A549 cells indicates activation of caspase and subsequential apoptosis induction. In conclusion, DNA damage induced by RX-3117 triggered apoptosis on one hand and increased Chk1 and Chk2 expression levels on the other hand. Without being limited to any mechanism of action, it is believed that the phosphorylated Chk1 and Chk2 may have triggered phosphorylation of Cdc25C and provoked its degradation, which resulted in decreased Cdk1 levels and thus accumulated cells in S-phase.

Example 2: Efficacy of RX-3117 in Syngeneic MC38 Murine Colon Cancer Xenograft Model Following the protocol described below, the effect of RX-3117 on tumor growth in a syngeneic model using female C57BL/6 mice with MC38 murine colon cancer was examined. Tumor growth was measured in a treatment group compared to a control (vehicle treated) group (see Table 1 below for dosing scheme and treatment regimen). The results of this study (Table 2) demonstrate that the addition of RX-3117 to a programmed death receptor 1 (PD-1) inhibitor, RMP1-14, had an additive effect in the inhibition of tumor growth (80% RX-3117 alone, 93% RMP1-14 alone, versus 99% in combination of two agents). Combination of the two agents also resulted in higher number of mice (9 mice) with partial regression and complete regression with 7 animals showing tumor free survival, compared to 4 animals with partial regression and complete regression in the RMP1-14 alone group with 2 showing tumor free survival. All results were obtained without any adverse effects to the mice in the combination group.

Briefly, the method is described as follows. The cells were harvested during exponential growth and re-suspended with phosphate buffered saline. Each test animal received a subcutaneous (s.c.) injection of 1×10$^6$ tumor cells into the right flank and tumor growth was monitored as the average tumor size approaches the target range of 60-100 mm$^3$. Dosing, based on Table 1 started as each animal reached this target range.

TABLE 1

Drugs and Treatment Schedule

| | | | Regimen 1 | | | Regimen 2 | | | |
|---|---|---|---|---|---|---|---|---|---|
| Gr. | N | Agent | mg/kg | Route | Schedule | Agent | mg/kg | Route | Schedule |
| 1# | 10 | Vehicle | — | Po | (5/2) x 3 | — | — | — | — |
| 2 | 10 | RX-3117 | 60 | Po | (5/2) x 3 | — | — | — | — |
| 4 | 10 | anti-PD-1 RMP1-14 | 100* | Ip | biwk x 2 | — | — | — | — |
| 5 | 10 | RX-3117 | 60 | Po | (5/2) x 3 | anti-PD-1 RMP1-14 | 100* | Ip | biwk x 2 |

Control Group,
*μg/animal

TABLE 2

Tumor Growth Inhibition and Survival Benefits of Combining RX-3117 with a PD-1 Inhibitor

| Gr. | Treatment Group | TGI Day 28 | PR | CR | TFS |
|---|---|---|---|---|---|
| 1 | Vehicle | — | 2 | 0 | 0 |
| 2 | RX-3117 (60 mg/kg) | 80% | 0 | 0 | 0 |
| 3 | anti-PD-1 RMP1-14 (100 µg) | 93% | 1 | 3 | 2 |
| 4 | RX-3117 + anti-PD-1 | 99% | 2 | 7 | 7 |

TGI: Tumor growth inhibition; at Day 28; PR: No. of Partial Regressions; CR: No. of Complete Regressions; TFS: No. of Tumor Free Survivors; all at Day 45

Tumors were measured in two dimensions using calipers, and volume calculated using the formula:

$$\text{Tumor Volume (mm}^3) = \frac{w^2 \times l}{2}$$

where w=width and l=length, in mm, of the tumor. Tumor weight may be estimated with the assumption that 1 mg is equivalent to 1 mm$^3$ of tumor volume.

Treatment efficacy was determined using data from Day 45. The MTV (n), the median tumor volume for the number of animals, n, on Day 45, was determined for each group. Percent tumor growth inhibition (% TGI) is defined as the difference between the MTV of the designated control group (vehicle administration) and the MTV of the drug-treated group, expressed as a percentage of the MTV of the control group:

$$\% \, TGI = \left(\frac{MTV_{control} - MTV_{drug\text{-}treated}}{MTV_{control}}\right) \times 100 = [1 - (MTV_{drug\text{-}treated}/MTV_{control})] \times 100$$

The data set for TGI analysis includes all animals in a group, except those that died due to treatment-related (TR) or non-treatment-related (NTR) causes. An agent that produces at least 60% TGI in this assay is considered to be potentially therapeutically active.

The study protocol specifies a tumor growth delay assay based on the median time to endpoint (TTE) in a treated group versus the control group. Each animal was euthanized for tumor progression (TP) when its tumor reaches the 1500 mm$^3$ volume endpoint. The time to endpoint (TTE) for each mouse is calculated with the following equation:

$$TTE = \frac{\log_{10}(\text{endpoint volume}) - b}{m}$$

where b is the intercept and m is the slope of the line obtained by linear regression of a log-transformed tumor growth data set. The data set is comprised of the first observation that exceeds the study endpoint volume and the three consecutive observations that immediately precede the attainment of the endpoint volume. Any animal that did not reach endpoint was euthanized at the end of the study and assigned a TTE value equal to the last day of the study (71 days), In instances in which the log-transformed calculated TTE precedes the day prior to reaching endpoint or exceeds the day of reaching tumor volume endpoint, a linear interpolation is performed to approximate TTE. Any animal determined to have died from treatment-related (TR) causes is assigned a TTE value equal to the day of death. Any animal that died from non-treatment-related (NTR) causes is excluded from TTE analysis.

Treatment efficacy was determined from the number of regression responses. Treatment may cause partial regression (PR) or complete regression (CR) of the tumor in an animal. In a PR response, the tumor volume is 50% or less of its D1 volume for three consecutive measurements during the course of the study, and equal to or greater than 13.5 mm$^3$ for one or more of these three measurements. In a CR response, the tumor volume is less than 13.5 mm$^3$ for three consecutive measurements during the course of the study. Any animal with a CR response on the last day of the study was additionally classified as a tumor-free-survivor.

For toxicity assessments, animals were weighed daily for the first five days of the study and twice weekly thereafter. The mice were observed frequently for overt signs of any adverse, treatment-related side effects, and clinical signs of toxicity are recorded when observed.

Acceptable toxicity is defined as a group mean body-weight loss of less than 20% during the study and not more than one treatment-related (TR) death among ten treated animals. Any dosing regimen resulting in greater toxicity is considered above the maximum tolerated dose (MTD). A death is classified as TR if attributable to treatment side effects as evidenced by clinical signs and/or necropsy, or if due to unknown causes during the dosing period or within fourteen days of the last dose. A death is classified as non-treatment-related (NTR) if there is no evidence that death was related to treatment side effects.

Prism 6.05 (GraphPad) for Windows was employed for statistical and graphical analyses. MTV values for multiple groups are compared with the non-parametric Kruskal-Wallis test and a post hoc Dunn's multiple comparison test. The two-tailed statistical analyses were conducted at P=0.05. Prism reports results as non-significant (ns) at P>0.05, significant (symbolized by "*") at $0.01<P\leq0.05$, very significant ("") at $0.001<P\leq0.01$ and extremely significant ("*") at $P\leq0.001$. Because statistical tests are tests of significance and do not provide an estimate of the size of the difference between groups, all levels of significance are described as either significant or non-significant within the text of this report.

A "box and whiskers" diagram was constructed to show the distribution of individual tumor volumes, by group, on D15. The box represents the 25$^{th}$ to 75$^{th}$ percentile of observations, the horizontal line corresponds to the median value, and the "whiskers" indicate the maximum and minimum values. Group median tumor volumes were plotted as functions of time. Group mean BW changes are graphed as percent change, ±SEM, from D1. Animals that died from NTR causes are excluded from all graphical presentations.

Survival was analyzed by the Kaplan-Meier method, based on TTE values. The logrank (Mantel-Cox) and Gehan-Breslow-Wilcoxon tests determine the significance of the difference between the overall survival experiences (survival curves) of two groups, based on TTE values. The Kaplan-Meier plot and statistical tests share the same data sets, and exclude any animals that are recorded as NTR deaths. A scatter plot is constructed to show TTE values for individual mice, by group; this plot shows NTR deaths, which are excluded from all other figures. Group mean tumor volumes are plotted as functions of time. When an animal exits the study because of tumor size or TR death, its final recorded tumor volume is included with the data used to calculate the median volume at subsequent time points. Tumor growth curves are truncated after two TR deaths occur in the same group. Group mean BW changes over the course of the study are graphed as percent change, ±SEM, from Day 1. Tumor growth and BW change curves are truncated after more than half the assessable mice in a group exits the study.

Example 3: Pharmacokinetics, Safety and Tolerability of RX-3117 in Humans

In a first-in-human, open-label, exploratory study, the pharmacokinetics, safety and tolerability of RX-3117 were evaluated. The study duration was 14-15 days (7-day screening period; 3-day treatment period; 4 (+1)-day safety follow-up period). Nine adult male and female subjects with histologically confirmed, solid tumors enrolled in and completed the study. The subjects received RX-3117 (n=3 subjects per dose) as a single oral dose (50 mg or 100 mg) or a single intravenous dose (20 mg).

Pharmacokinetics (PK)

The absolute bioavailability (F) for oral RX-3117 was 55.67% and 33.42% for the 50 and 100 mg doses, respectively. The mean $T_{max}$ was 2.16 hours and 2.49 hours for the 50 and 100 mg doses, respectively. The mean $C_{max}$ was 303.3 ng/mL and 311.43 ng/mL for the 50 and 100 mg doses, respectively. The greater absolute bioavailability and $C_{max}$ results of the 50 mg dose compared to the 100 mg dose suggests that oral bioavailability of RX 3117 in plasma may not be dose-proportional. The $T_{1/2}$ for the 50 mg and 100 mg doses was 13.95 hours and 20.92 hours, respectively, indicating that RX-3117 may show dose proportionality on some parameters but not on others at the doses tested.

The plasma PK profile of intravenous RX-3117 differed from the plasma PK profile of oral RX-3117. The 20 mg dose of intravenous RX-3117 recovered rapidly after bolus infusion ($T_{max}$=0.25 hours). The 20 mg dose of intravenous RX-3117 had a mean $C_{max}$ of 1143.63 ng/mL, which was approximately a 4-fold increase over the peak concentrations of the oral doses.

Safety and Tolerability

RX-3117 was safe and well-tolerated in all subjects. No adverse event (AE), treatment-emergent adverse event (TEAE) or serious adverse event (SAE) occurred.

The results show that RX-3117 is safe and well-tolerated with oral bioavailability, and support the study of higher doses.

Example 4: Pharmacokinetics, Safety and Tolerability of RX-3117 at Different Oral Doses In an open-label, dose-ranging study, the pharmacokinetics (PK) of RX-3117 at various oral doses was evaluated. Subjects with advanced malignant tumors were administered capsules containing RX-3117 at daily doses of 30 mg (N=1), 60 mg (N=1), 100 mg (N=3), 150 mg (N=3), 200 mg (N=3), 500 mg (N=3), 1000 mg (N=3), 1500 mg (N=4), and 2000 mg (N=5 to date) 3 times a week (TIWK) for 3 weeks with 1 week off during each 4 week cycle. Based on the continued safety profile, and to enhance weekly RX-3117 exposure, more frequent dosing was also implemented. In addition to the TIWK dosing scheme discussed above, subjects also received 500 mg and 700 mg 5 times a week, and 500 mg for 7 times a week for 3 weeks with 1 week off during each 4 week cycle. Dose escalation began with an accelerated design treating 1 subject per dose (Simon et al., *J Natl. Cancer Inst.*, 89(15):1138-47 (1997) followed by a standard 3+3 design using a modified Fibonacci sequence after the occurrence of a single related Grade 2 or greater adverse event. Table 3 summarizes the dosing schedule.

TABLE 3

Dose Escalation - 3 Times per Week

| Dose Group | Actual dose (mg) | Frequency | Total weekly dose (mg) | Total cycle dose (mg) |
| --- | --- | --- | --- | --- |
| 1 | 30 | 3 times per week | 90 | 270 |
| 2 | 60 | 3 times per week | 180 | 540 |
| 3 | 100 | 3 times per week | 300 | 900 |
| 4 | 150 | 3 times per week | 450 | 1,350 |
| 5 | 200 | 3 times per week | 600 | 1,800 |
| 6 | 500 | 3 times per week | 1,500 | 4,500 |
| 7 | 1,000 | 3 times per week | 3,000 | 9,000 |
| 8 | 1,500 | 3 times per week | 4,500 | 13,500 |
| 9 | 2,000 | 3 times per week | 6,000 | 18,000 |
| 10 | 500 | 5 times per week | 2,500 | 7,500 |
| 11 | 700 | 5 times per week | 3,500 | 10,500 |
| 12 | 500 | 7 times per week | 3,500 | 10,500 |

Pharmacokinetics (PK)

PK data are presented in Table 4.

Figure 12:
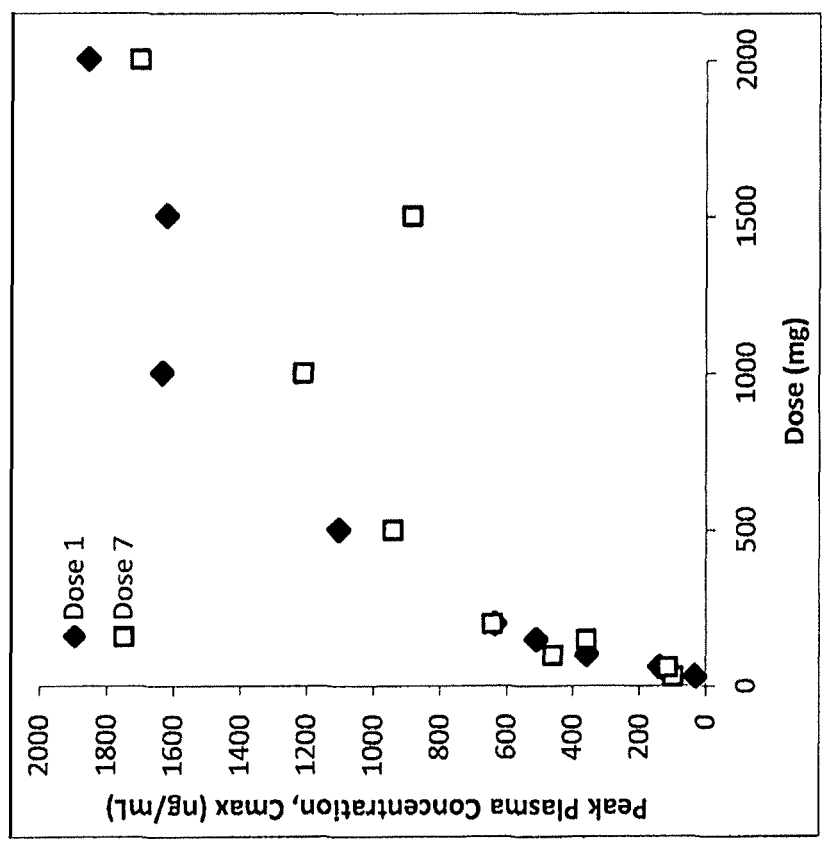
FIG. 12 is a graph showing the peak plasma concentration C$_{max}$ (ng/mL) following dose 1 and dose 7.
Figure 13:
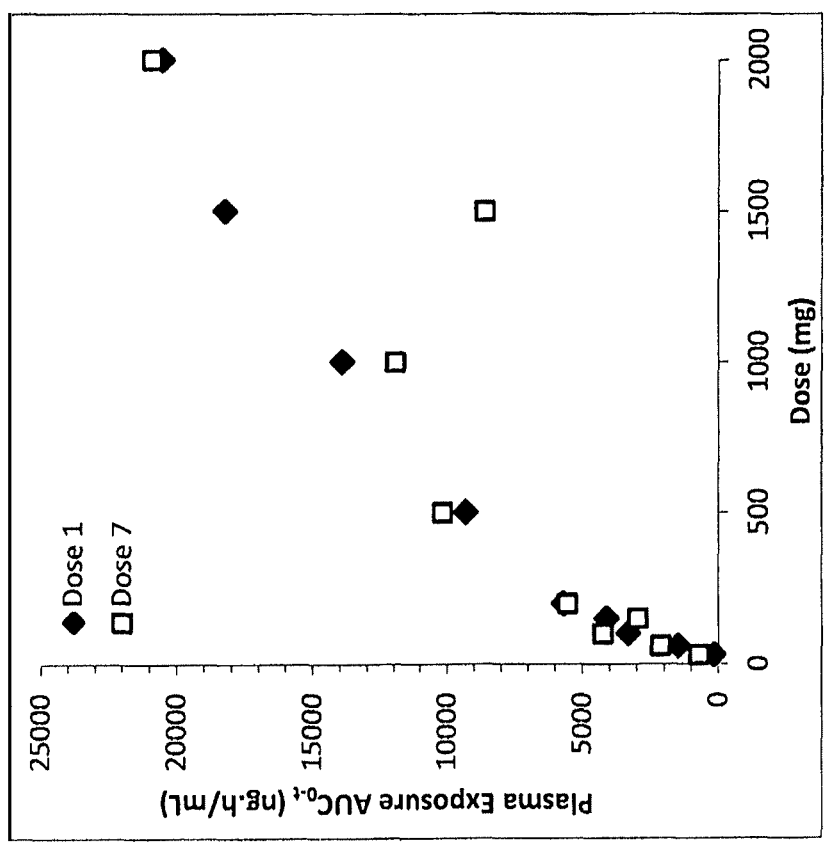
FIG. 13 is a graph showing the plasma exposure in $AUC_{0-t}$ (ng·h/mL) following dose 1 and dose 7.

RX-3117 was rapidly absorbed without a marked lag time, with median $T_{max}$ usually observed at 2 to 3 hours. After $T_{max}$, elimination was biphasic with about half of $AUC_{0-t}$ (0-24 hours) observed in the first 8 hours, and over 80% by 24 hours. Apparent terminal $T_{1/2}$ did not exhibit dose-dependent or time-dependent pharmacokinetics, with mean values over the dose range 60 to 2000 mg ranging from 11.6 to 16.7 hours after the first dose, and from 12.3 to 20.2 hours after the seventh dose (Day 15 of dosing). $C_{max}$ and $AUC_{0-t}$ (0-24 hours) increased fairly linearly with dose, but in a less than proportional manner, possibly reaching a plateau by the 1500 mg dose (FIGS. 12 and 13). Over the dose range of 30 to 2000 mg, mean $C_{max}$ ranged from 32 to 1858 ng/mL after the first dose, and from 99 to 1703 ng/mL after the seventh dose (FIG. 12). Over the same dose range, mean $AUC_{0-t}$ (0-24 hours) ranged from 164 to 20,544 hr·ng/mL after the first dose, and from 702 to 20,919 hr·ng/mL after the seventh dose (FIG. 13). Accumulation was generally minimal.

The PK data show a dose dependent increase in exposure with doses up to 1000 mg TIWK. At doses greater than 500 mg TIWK, the $C_{max}$ and $AUC_{0-t}$ (0-24 hours) after the 7th dose are consistently lower than those measured after the first dose (FIGS. 12 and 13). Due to the plateauing of $C_{max}$ and $AUC_{0-t}$ (0-24 hours) values at doses above 1000 mg, a more frequent dosing schedule was used to enhance weekly exposures (Table 4). Based on the results of this study the maximum tolerated dose (MTD) for RX-3117 was determined to be 700 mg daily at 5 days per week, given for three weeks with 1 week off per 4-week cycle. This MTD was then used for follow-up efficacy studies.

TABLE 4

PK Data after Days 1 and 15 of Study

| Frequency | Dose (mg) | Dose Day | Dose Number | $C_{max}$ (ng/mL) | $T_{max}$ (hr) | $T_{1/2}$ (hr) | $AUC_{0-24}$ (hr*ng/mL) |
| --- | --- | --- | --- | --- | --- | --- | --- |
| 3 per Week | 30 | 1 | 1 | 31.6 | 2 | 3.87 | 252 |
| 3 per Week | 60 | 1 | 1 | 139 | 2 | 16.2 | 1164 |
| 3 per Week | 100 | 1 | 1 | 357 | 2 | 15.4 | 2714 |

TABLE 4-continued

PK Data after Days 1 and 15 of Study

| Frequency | Dose (mg) | Dose Day | Dose Number | $C_{max}$ (ng/mL) | $T_{max}$ (hr) | $T_{1/2}$ (hr) | $AUC_{0-24}$ (hr*ng/mL) |
|---|---|---|---|---|---|---|---|
| 3 per Week | 150 | 1 | 1 | 511 | 3 | 13.9 | 3546 |
| 3 per Week | 200 | 1 | 1 | 637 | 2 | 13.3 | 4719 |
| 3 per Week | 500 | 1 | 1 | 1104 | 2 | 16.7 | 7916 |
| 3 per Week | 1000 | 1 | 1 | 1635 | 2 | 11.6 | 12218 |
| 3 per Week | 1500 | 1 | 1 | 1622 | 3 | 11.8 | 15322 |
| 3 per Week | 2000 | 1 | 1 | 1858 | 3 | 13.3 | 17044 |
| 5 per Week | 500 | 1 | 1 | 1441 | 2 | 7.31 | 12373 |
| 5 per Week | 700 | 1 | 1 | 989 | 3 | 9.05 | 8663 |
| 7 per Week | 500 | 1 | 1 | 1269 | 3 | 8.28 | 10097 |
| 3 per Week | 30 | 15 | 7 | 98.9 | 2 | 8.23 | 702 |
| 3 per Week | 60 | 15 | 7 | 113 | 4 | 15.7 | 1566 |
| 3 per Week | 100 | 15 | 7 | 460 | 2 | 20.2 | 3289 |
| 3 per Week | 150 | 15 | 7 | 360 | 3 | 15.1 | 2437 |
| 3 per Week | 200 | 15 | 7 | 643 | 3 | 16.2 | 4574 |
| 3 per Week | 500 | 15 | 7 | 941 | 3 | 15.3 | 8275 |
| 3 per Week | 1000 | 15 | 7 | 1210 | 3 | 14.9 | 9753 |
| 3 per Week | 1500 | 15 | 7 | 883 | 2 | 13.8 | 7050 |
| 3 per Week | 2000 | 15 | 7 | 1703 | 3 | 12.1 | 17403 |
| 5 per Week | 500 | 15 | 11 | 1212 | 2 | 8.71 | 9201 |
| 5 per Week | 700 | 15 | 11 | 674 | 4 | 11.2 | 6321 |
| 7 per Week | 500 | 15 | 15 | 1363 | 2.5 | 9.45 | 14467 |

Safety and Tolerability

The most frequently observed adverse events were mild to moderate fatigue and nausea, mild diarrhea, mild vomiting, mild anorexia and moderate dehydration. Dose limiting toxicities were limited to Grade 3 anemia, thrombocytopenia.

Example 5: Efficacy, Safety and Tolerability of RX-3117 in Humans

The efficacy, safety and tolerability of RX-3117 at various doses and frequencies were evaluated (see Example 4, above). Subjects with advanced malignant tumors were administered capsules containing RX-3117 at various doses, from TIWK to 7 times per week for 3 weeks with 1 week off during each 4-week cycle. Dose escalation begins with an accelerated design treating 1 subject per dose (Simon et al., *J. Natl. Cancer Inst.*, 89(15):1138-47 (1997) followed by a standard 3+3 design using a modified Fibonacci sequence after the occurrence of a single related Grade 2 or greater adverse event. Table 4 (above) summarizes the dosing schedule.

The subjects were assessed for efficacy, safety and tolerability of RX-3117. Total of 48 subjects were enrolled (30 Females, 18 males). Seventeen subjects experienced stable disease for 1 to 10 cycles; with 10 subjects receiving treatment from 82 to 276 days. A tumor burden reduction was seen in 3 subjects with pancreatic (tumor volume and biomarkers of CA19-9), breast and mesothelioma cancers. The most frequent related adverse events were moderate to severe anemia, mild to moderate fatigue and nausea, mild diarrhea, vomiting, and anorexia.

In another stage of this study, RX-3117 is being evaluated in a Phase Ib/IIa clinical trial in cancer patients with relapsed or refractory pancreatic cancer or advanced bladder cancer (including muscle-invasive bladder cancer). The Phase Ib/IIa clinical trial is a multi-center study that evaluates the safety and efficacy of RX-3117 in these target patient populations. Secondary endpoints include safety and pharmacokinetic analyses. Patients in the trial are receiving a daily oral dose of RX-3117 of 700 mg, five times weekly for three weeks in a 28 day cycle and 4 treatment cycles, or until their disease progresses.

Example 6: The Radiosensitizing Effect of Fluorocyclopentenyl-Cytosine (RX-3117) in Ovarian and Lung Cancer Cell Lines Drugs and Chemicals Stock solutions of RX-3117 were made in deionized water. All other chemicals used were of standard quality and commercially available.

Cell Culture

The human NSCLC cell lines A549 (adenocarcinoma), H460 (large cell carcinoma), SW1573 (alveolar carcinoma), and SW1573/G- (SW1573 cell line resistant to gemcitabine) and the ovarian cancer cell line A2780 were kept in exponential growth in T25 flasks (Greiner Bio-One GmbH, Frickenhausen, Germany) and cultured in Dulbecco's minimal essential medium (DMEM) or RPMI 1640 supplemented with 10% heat-inactivated fetal bovine serum (FBS), 1% streptomycin and penicillin, and maintained at 37° C. under a saturated atmosphere of 5% $CO_2$. Cells were harvested using trypsin EDTA (Invitrogen, Paisley, UK). A Coulter® Z™ series counter was used to count cells.

Clonogenic Assay

Exponential growing A2780, SW1573, A549, H460 and SW1573/G-cells were exposed to 1 µM RX-3117 or untreated (control) for 24 h and irradiated with single doses γ-radiation (0-6 Gy) using a $^{60}Co$ source (Gammacell 200, Atomic Energy of Canada, Ltd). Subsequently, 500 cells/T25 flasks were plated and allowed to form colonies. After ten days colonies were fixed with 100% ethanol and stained with 10% Giemsa stain solution (Merck Chemicals BV, Amsterdam, the Netherlands) for colonies counting. Plating efficiency (PE) was calculated by dividing the number of colonies formed through the number of cells plated and normalized for cytotoxicity induced by control. To illustrate the effect of RX-3117 on radiation, dose modifying factor (DMF) was calculated as described earlier (Bijnsdorp I V, van den Berg J, Kuipers G K, Wedekind L E, Slotman B J, van Rijn J, Lafleur M V M and Sminia P: Radiosensitizing potential of the selective cyclooygenase-2 (COX-2) inhibitor meloxicam on human glioma cells. *J Neurooncol* 85: 25-31, 2007).

Spheroid Assay

The NSCLC cell lines A549 and SW1573 were plated in low attachment 24 well plates (Corning Incorporated, Corning, N.Y.) at a density of 100,000 cells/well and allowed to form spheroids. After three days, single spheroids were transferred to new 24 well low attachment plates (one spheroid/well). Immediately after transfer treatment was started, for A549 and SW1573 cells 1 µM RX-3117 was combined with fractionated 2 Gy irradiation (5 days single 2 Gy dose). Pictures were taken on day 0 (before irradiation) and after 3, 6, 9, and 15 days using a phase contrast microscope (LeicaDMI300B Universal Grab 6.3 software, Digital Cell Imaging Labs). The measurements were taken by ImageJ software (ImageJ 1.45s, Wayne Rasband, National Institutes of Health, Bethesda, Md.) for spheroid volume calculation ($V=4/3\pi(D/2)^3$) as described earlier by Galvani et al. (Galvani E, Giovannetti E, Saccani F, Cavazzoni A, Leon L G, Dekker H, Alfieri R, Carmi C, Mor M, Ardizzoni A, Petronini P G and Peters G J: Molecular mechanisms underlying the antitumor activity of 3-aminopropanamide irreversible inhibitors of the epidermal growth factor receptor in non-small cell lung cancer. *Neoplasia* 15: 61-72, 2013).

Flow Cytometry Analysis

Cell cycle distribution and apoptosis were analyzed by plating cells in flat bottom 6 well plates (Greiner Bio-One GmbH, Frickenhausen, Germany) at the density of 5,000 cells and allowed to attach for 24 h. Thereafter cytotoxic concentrations of 5×$IC_{50}$ were added. The exposure time was 24 h and 48 h and for comparison the control group was included. At each time point total amount of adherent and floating cells were harvested in round-bottom FALCON tubes (BD, Franklin Lakes, N.J., USA). After centrifugation, cell pellets were resuspended in 1.0 ml propidium iodide (PI) solution (50 ug/ml PI, 0.1% sodium citrate 0.1% Triton X-100, 0.1 mg/ml ribonuclease A) or 10 ul Annexin V (cat#31490014, Immunotools) and left on ice for 30 minutes. Subsequently, samples were analyzed using FACSCalibur (BD Biosciences, Mount View, Calif., USA). For data analysis CELLQuest™ software was carried out, using gates on DNA histograms to estimate the amount of cells in sub-G1 phase (apoptotic cells).

Protein Expression Analysis

The influence of RX-3117 on protein expression during different treatment conditions was analyzed by western blot. Cells were lysed using 1× cell lysis buffer (Cell Signaling, Danvers, Mass., USA) containing 4% protease inhibitor cocktail (Roche Diagnostics, Mannheim, Germany) on ice for 30 minutes and centrifuged for 10 minutes at 4° C. at 14,000 rpm. Bio-Rad assay was performed to determine protein amount in the collected supernatant as described earlier (Lemos C, Kathmann I, Giovannetti E, Calhau C, Jansen G and Peters G J: Impact of cellular folate status and epidermal growth factor receptor expression on BCRP/ABCG2-mediated resistance to gefitinib and erlotinib. *Br J Cancer* 100: 1120-7, 2009). The following antibodies were used for protein expression: γH2A.X (cat#9718, Cell Signaling, 1:1000), β-actin (Sigma, 1:10,000), Cdc25C Ser216 (cat#4901, Cell Signaling, 1:1000), Cdk1 Tyr15 (cat#9111, Cell Signaling, 1:1000), Chk1 Thr68 (cat#2197S, Cell Signaling, 1:1000), Histone 3 (cat#4499, Cell Signaling). Antibodies were diluted in 1:1 solution with Rockland buffer (Rockland Inc, Philadelphia, Pa.) and phosphate buffered saline (PBS) supplemented with 0.05 Tween 20. Proteins were separated in 20% SDS-PAGE gel and transferred to polyvinylidene difluoride (PVDF) membrane. For fluorescent signal secondary anti-bodies goat anti-mouse InfraRedDye and goat anti-rabbit InfraRedDye were used. Proteins were detected by an Odyssey InfraRed Imager (Li-COR Bioscience, Lincoln, Nebr.).

Results

Radiosensitizing Effect of RX-3117

To investigate the effect of RX-3117 on radiation, clonogenic assays were performed. First, the inventors examined whether pre- or post-incubation with RX-3117 enhanced the effect of radiation. Pre- and post-treatment with RX-3117 together with 4 Gy were compared in A2780 cells.

Figure 15:
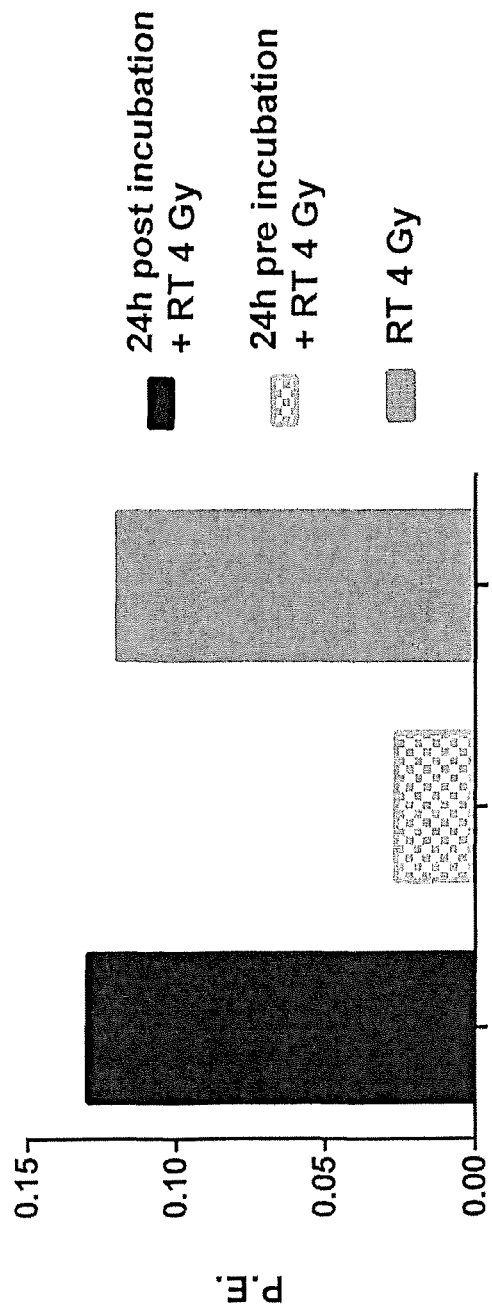
FIG. 15 is a bar graph showing the radiosensitizing effect pre- or post-incubation with RX-3117. The gray bar represents control, irradiated A2780 cells with 4 Gy, the black bar represents incubation with 1 µM RX-3117 for 24 hours after irradiation with 4Gy. The white/gray bar represents 24 hours incubation with 1 µM RX-3117 before irradiation with 4Gy. P.E. represents plating efficiency.

The clonogenic assay data showed that pre-incubation with RX-3117 was the most effective condition for a radio sensitizing effect. Pre-incubation with 1 µM RX-3117 had a five times lower plating efficiency compared to control (FIG. 15).

Figure 16A:
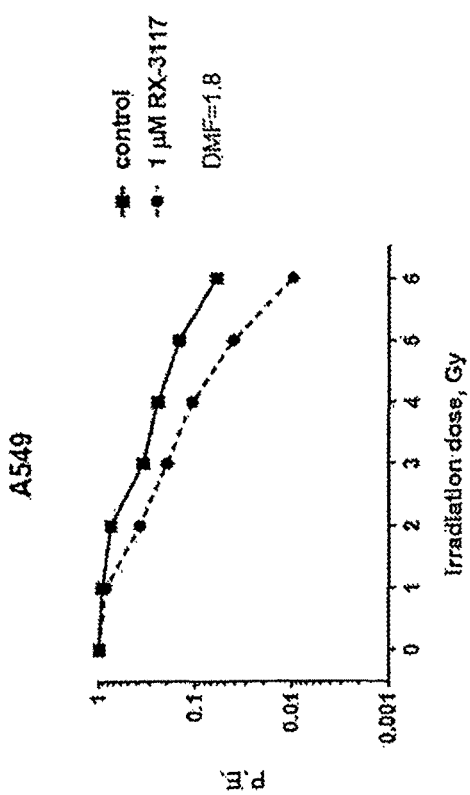
Figure 16B:
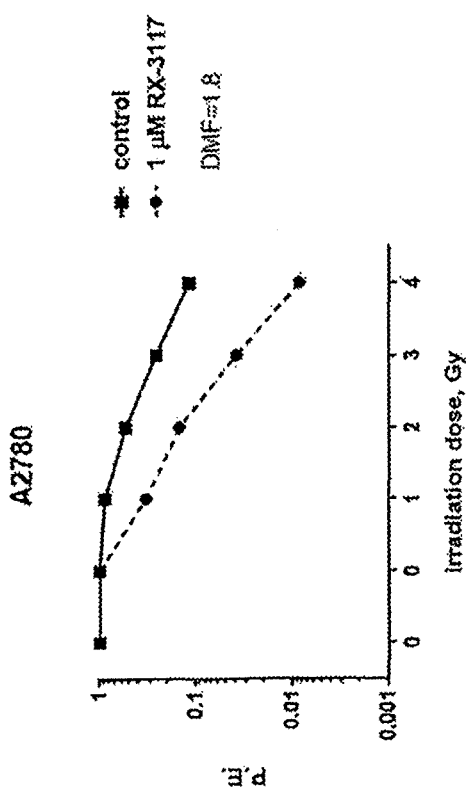

Using the pre-incubation schedule, the potential radiosensitizing effect was investigated in A2780 cells and the non-small cell lung cancer cell lines A549, SW1573 and SW1573/G- and H460. In general, all cell lines showed a radiosensitizing effect when treated with RX-3117 and radiation. The greatest radiosensitizing was observed in the A2780 and A549 cell lines with a DMF of 1.8 and SW1573 with DMF of 1.5 (FIGS. 16A, 16B, 16D). The gemcitabine resistant cell line SW1573/G- had a DMF of 1.4 (FIG. 16E), but H460 cells showed a poor radiosensitizing effect. Since fractionated radiation is the standard procedure in the clinic, a fractionated dose of 2 Gy irradiation during 5 days in SW1573 cells was also studied. Incubation with 1 µM of RX-3117 prior to fractionated radio therapy of 5 times 2 Gy showed the lowest colonies outgrowth (FIG. 16F).

Figure 17A:
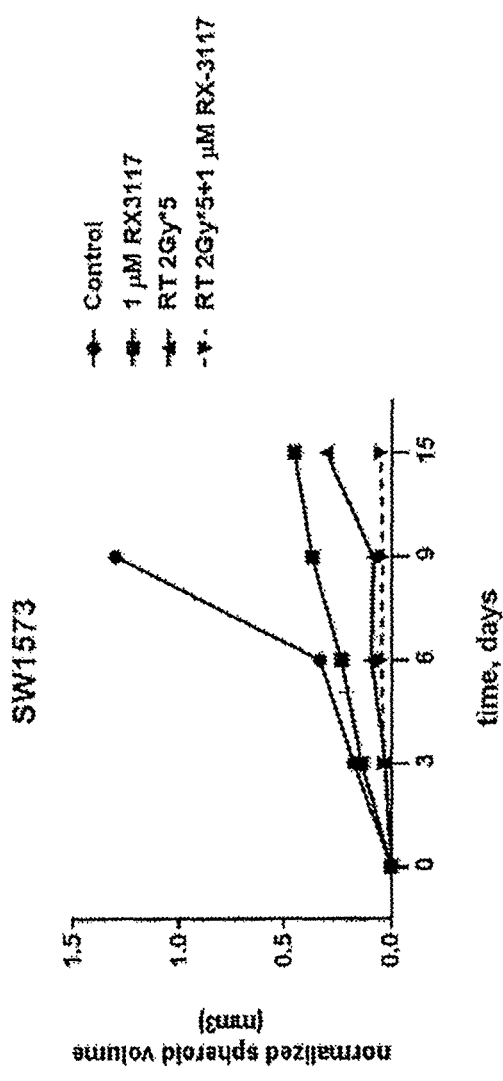
FIGS. 17A-17B is series of graphs showing the radiosensitizing effect of RX-3117 on spheroids.
Figure 17B:
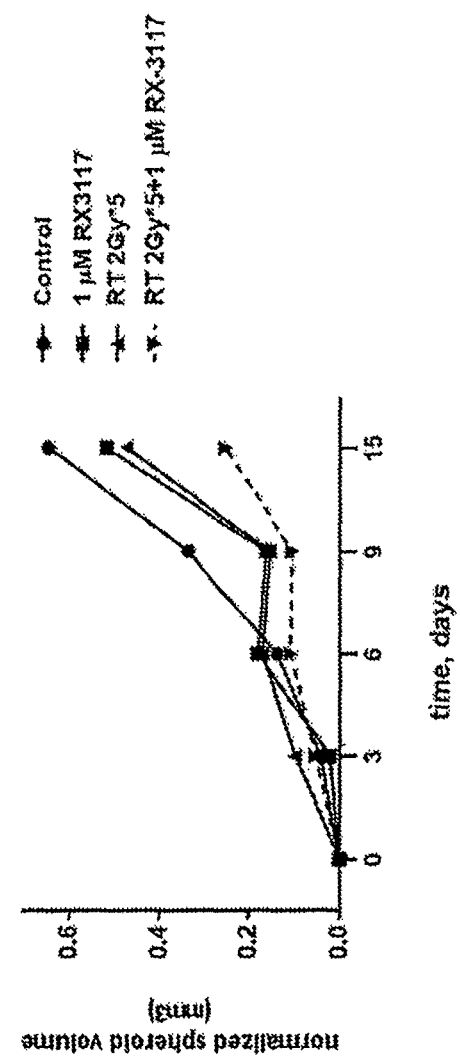

The radiosensitizing ability of RX-3117 in combination with irradiation in a 3-dimensional model using a spheroid assay was also investigated. The sphere formation assay revealed a radiosensitizing effect of RX-3117 on spheres in SW1573 and A549 spheroids (FIG. 17). SW1573 spheres were highly affected by both 1 µM RX-3117 alone and by radiotherapy (RT) alone (2 Gy 5 days) and the effect was enhanced with the combination. In A549 cells, RX-3117 treatment or irradiation alone had only a small effect on the volume growth while 1 µM RX-3117 enhanced the effect of 5 days irradiation with 2 Gy (FIG. 17).

Apoptosis Initiation

The potential of RX-3117 to induce apoptosis was studied in the NSCLC cell lines. The amount of apoptotic cells were measured by Annexin V staining (FIG. 18) after 24 h, 48 h and 72 h of exposure. Annexin V cell membrane staining showed a gradual increase in apoptotic cells for A549 cells and SW1573 cells, which was more pronounced for SW1573 cells than for A549.

DNA Damage Initiation

DNA damage is a hallmark for cell death. DNA damage was studied by evaluation of γH2A.X expression. In the A2780 cell line gradually increasing RX-3117 concentrations starting by 0.1 µM to 10 µM RX-3117 showed induction of γH2A.X S139 in a dose dependent manner (FIG. 18A). In the SW1573 cell line the double strand break damage marker was increased after 48 h of exposure to 0.3 µM of RX-3117 (FIG. 18B). A combination of 0.3 µM of RX-3117 and irradiation showed more pronounced γH2A.X S139 protein expression (FIG. 18B). As expected radiation caused an immediate increase of the expression of γH2A.X; in the presence of RX-3117 the repair was delayed.

Figures 19A, 19B:
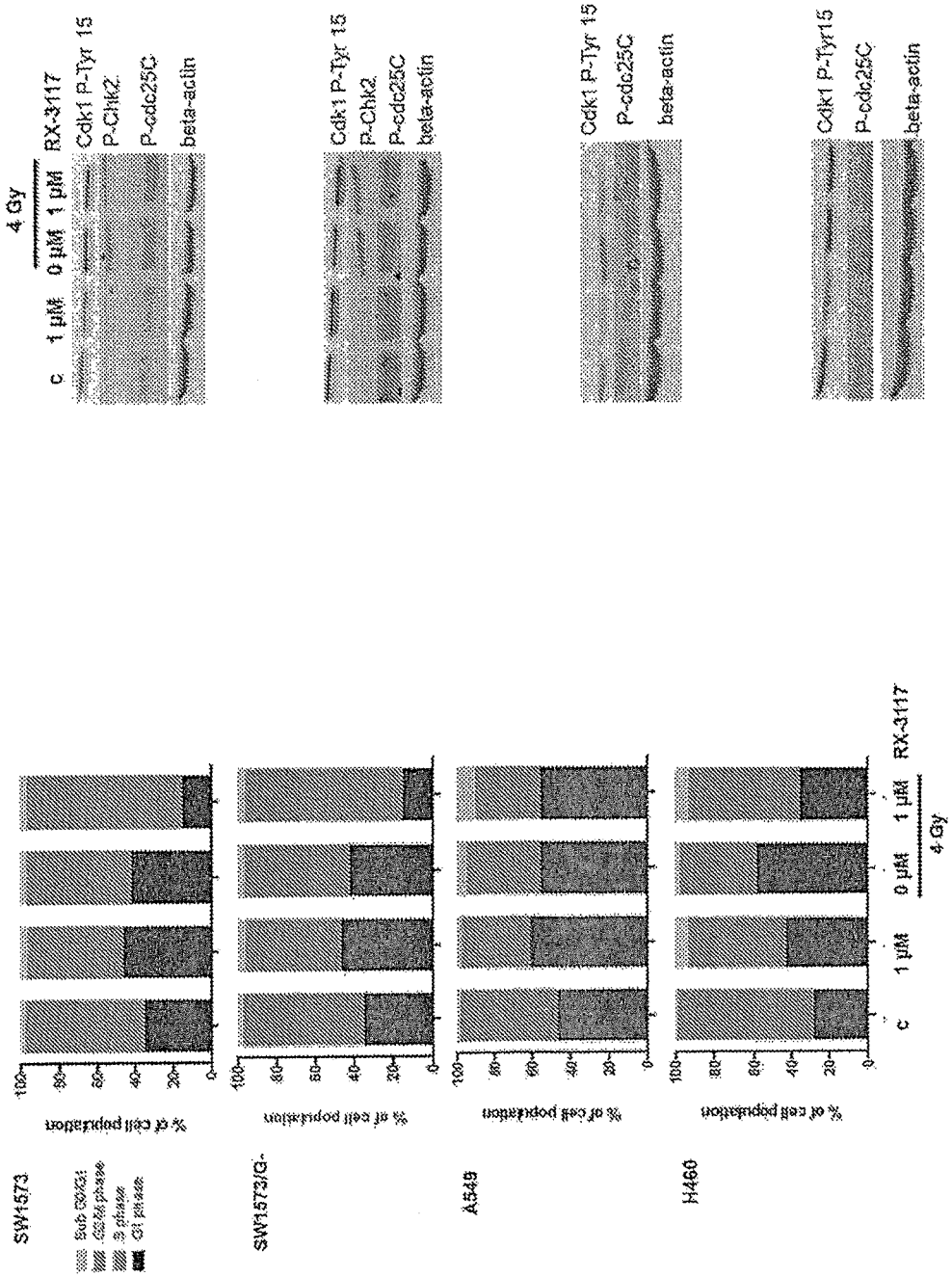
FIGS. 19A-19B is a series of histograms (A) bar graphs and western blots (B) showing disturbance in cell cycle distribution by RX-3117 and radiation in cell lines.

Effect of Treatment with RX-3117 and Radiation on Cell Cycle Distribution and Cell Death Since a disturbance in cell cycle distribution has been reported to be implicated in the radiosensitizing effect of other nucleoside analogs (Shewach D S and Lawrence T S: Antimetabolite radiosensitizers. *J Clin Oncol* 25: 4043-50, 2007), the effect of RX-3117 in combination with radiation was investigated using FACS analysis in the NSCLC cells. At the relatively low concentration of 1 µM RX-3117 a small but just significant ($p<0.05$) cell line dependent increase of the S-phase was found in 3 out of 4 cell lines. In all cell lines an increase in the G1 phase was found (FIG. 19A) and a strong decrease of the G2/M phase was found. Radiation at 4 Gy caused a clear decrease of the amount of cells in the S-phase, an increase in the G2/M phase in both SW1573 cells and no effect in A549 cells, but a decrease in the H460 cells (FIG. 19A). The combination of radiation and RX-3117 led to an increased number of cells in the S-phase in both SW1573 variants, but a decrease in H460 cells. In A549 cells cell kill (sub G1) was clearly increased, but not in the other cells (FIG. 19A).

Figure 20:
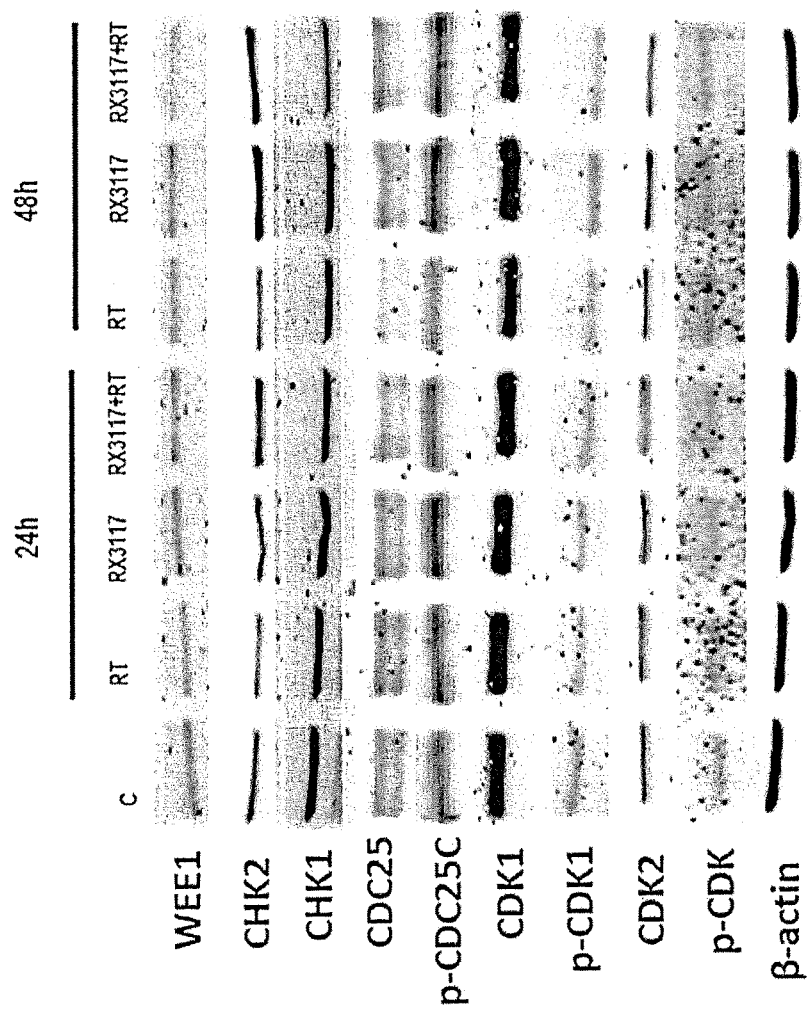
FIG. 20 is a series of western blots showing the effect of RX-3117 and radiation on the expression of cell cycle proteins in SW1573 cells. Cells were radiated (RT) in the presence and absence of RX-3117. Expression was measured by western blotting using the Odyssey system.

In order to understand some of these phenomena the effect of RX-3117 and radiation on the expression of some essential cell cycle proteins was also investigated. (FIG. 19B, and FIG. 20). In SW1573 the effect of both RX-3117 and radiation were examined on various cell cycle checkpoint proteins (FIG. 20). Radiation caused an interesting decrease in wee1, Chk2, CDC25c and p-CDC25c after 48 hr. In both SW1573 cells radiation caused an increase in the phosphorylation of Chk2 (FIG. 19B). In almost all cell lines (except the gemcitabine resistant SW-1573/G) RX-3117 decreased the phosphorylation of Cdk1; similarly radiation increased the phosphorylation of cdc-25C (but not in SW1573/G-) in 24 hr (FIG. 19B). In combination with RX-3117 this effect was maintained (FIG. 19B).

Example 7: Inhibition of DNA Methyltransferase by RX-3117 Leads to Upregulation of Hypomethylated Targets RX-3117 resembles azacytidine (aza-CR) and aza-deoxycytidine (aza-CdR). RX-3117 is taken up by the human equilibrative nucleoside transporter (hENT) and activated by uridine-cytidine kinase 2 (UCK2) to RX-3117-MP (FIG. 21). RX-3117 is taken up by the human equilibrative nucleoside transporter (hENT) and activated by uridine-cytidine kinase 2 (UCK2) to RX-3117-MP. RX-3117 downregulates DNA methyltransferase 1 (DNMT1) (Choi W. J., et al., *J Med. Chem.* 55 (2012) 4521-4525; Peters G. J., et al., *Invest New Drugs* 31 (2013) 1444-1457). DNMT1 is responsible for maintaining methylation in newly synthesized DNA in the S-phase and methylates cytosine residues in hemimethylated DNA. The rate of deamination of RX-3117 is much slower than gemcitabine.

RX-3117 is an orally bioavailable novel cytidine analog which is currently being evaluated in Phase I clinical study. The maximal tolerated dose is higher than 2,000 mg/day. Downregulation of DNMT1 by RX-3117 has been shown in various cell lines with different histological backgrounds. Currently both UCK2 and DNMT1 are being evaluated as potential biomarkers. In this example, the effect of RX-3117 on DNMT1 at the DNA, RNA, protein and enzyme activity, and reactivation of suppressed target genes, including p16INK4A, methylguanine methyltransferase (MGMT) and the proton coupled folate transporter (PCFT) were determined. PCFT includes transports folic acid, methotrexate (MTX) and pemetrexed (PMX) at pH 5.5 and 7.4, and the gene is highly methylated. In addition, the function of proteins for which the gene is known to be regulated by methylation are studied, including: proton-coupled folate transporter (PCFT). Expressions of E-cadherin (an adhesion molecule), p16INK (a tumor suppressor protein), and O-6 Methylguanine DNA methyltransferase (MGMT) (a DNA repair gene) in A549 cell line were also studied.

Methods

In this study, the following cell lines were used: (1) CCRF-CEM cells and its MTX resistant variant CEM-MTX, characterized by a deficiency of the reduced folate carrier (RFC) (Jansen G., et al., JBC 273 (1998) 30189-30198). The PCFT gene in CEM cells is highly methylated. (Gonen N., et al., BBRC 376 (2008) 787-92.); (2) CEM cells cultured in RPMI medium with 10% fetal bovine serum (FBS); and (3) A549 and SW1573 non-small cell lung cancer (NSCLC) and A2780 ovarian cancer cell lines cultured in DMEM medium with 10% FBS.

DNMT1 protein expression was measured by Western Blotting after exposure to RX-3117 for 24 or 48 hr. DNMT1 RNA expression was measured by real-time PCR after 24 and 48 hr exposure to RX-3117. DNMT enzyme activity was measured in isolated nuclei after exposure 1 µM RX-3117 or 5 µM aza-CdR using a DNA methyltransferase assay kit provided by EpiGentek using the ability of a CpG dinding domain to bind to methylated DNA. In A549 cells the effect of 5 µM RX-3117 on overall methylation was measured with a specific antibody against 5-methyl-cytosine. Bands on Western blots were visualized using appropriate InfraRed-Dye using an Odyssey InfraRed imager.

MTX transport was measured using radiolabeled MTX in CEM wild type and CEM-MTX cell lines. CEM cells have a high RFC activity. CEM-MTX are completely deficient in RFC-mediated transport. CEM cells have a highly methylated PCFT transporter and a very low PCFT mediated transport (Gonen N., et al., BBRC 376 (2008) 787-92). MTX transport at pH 7.4 is predominantly RFC mediated and less than 2% by PCFT. Folic acid was used to inhibit PCFT mediated transport. L-leucovorin (L-LV) was added to completely inhibit RFC mediated transport. CEM and CEM-MTX cells were exposed to 29.6 µM RX-3117 and to 0, 19 µM aza-CdR as a positive control. MTX transport was measured after 24 hr to the drugs in a 3 minutes uptake assay using 2 µM [3',5,'7-3H]-MTX.

Statistics were done using the Student's t-test.

Results

Figure 25C:
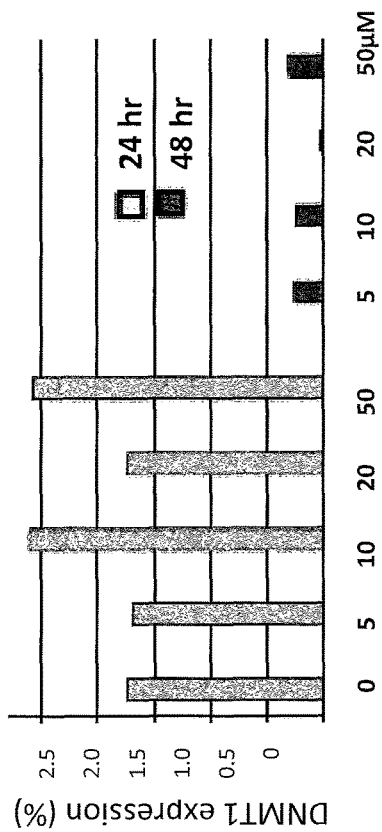
Figure 25D:
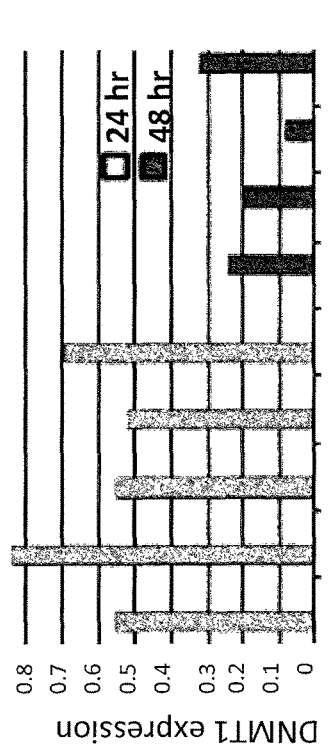

In the moderately sensitive non-small cell lung cancer (NSCLC) cell lines such as A549 and SW1573, 5-50 µM RX-3117 downregulated DNMT1 protein expression by 5-20% after 24 hour exposure and >90% after 48 hr (FIGS. 25A and B). DNMT1 mRNA was not affected after 24 hours exposure but was affected moderately after 48 hr (FIGS. 25 C and D).

Figures 26A, 26B:
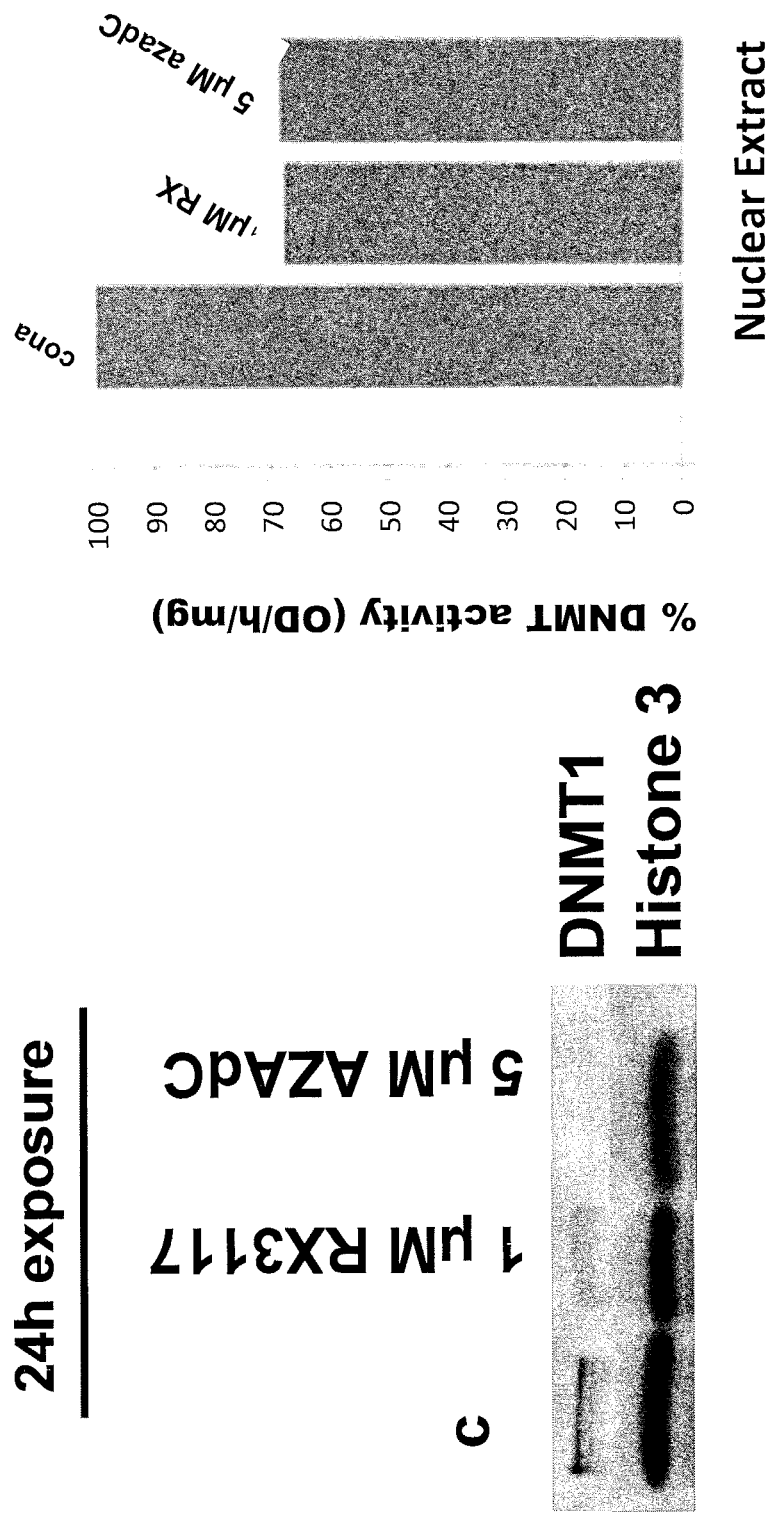
FIGS. 26A-26B is a western blot and a graph showing the effect of RX-3117 (1 µM) and aza-dC (5 µM) on A2780 ovarian cancer cells for 24 hr. Nuclear extracts were isolated and DNMT1 expression was measured by western blot (FIG. 26A) and activity (FIG. 26B) by a commercial kit as described in the Methods.

In the sensitive ovarian cancer cell line A2780, protein down regulation was already observed after 24 hr at 1 µM RX-3117 (FIGS. 26 A and B). DNMT1 activity was inhibited by 1 µM RX-3117 by 32% which was similar to the percent inhibition with 5 µM of the reference compound 5-aza-2'-deoxycytidine (DAC, 31%).

Figure 27A:
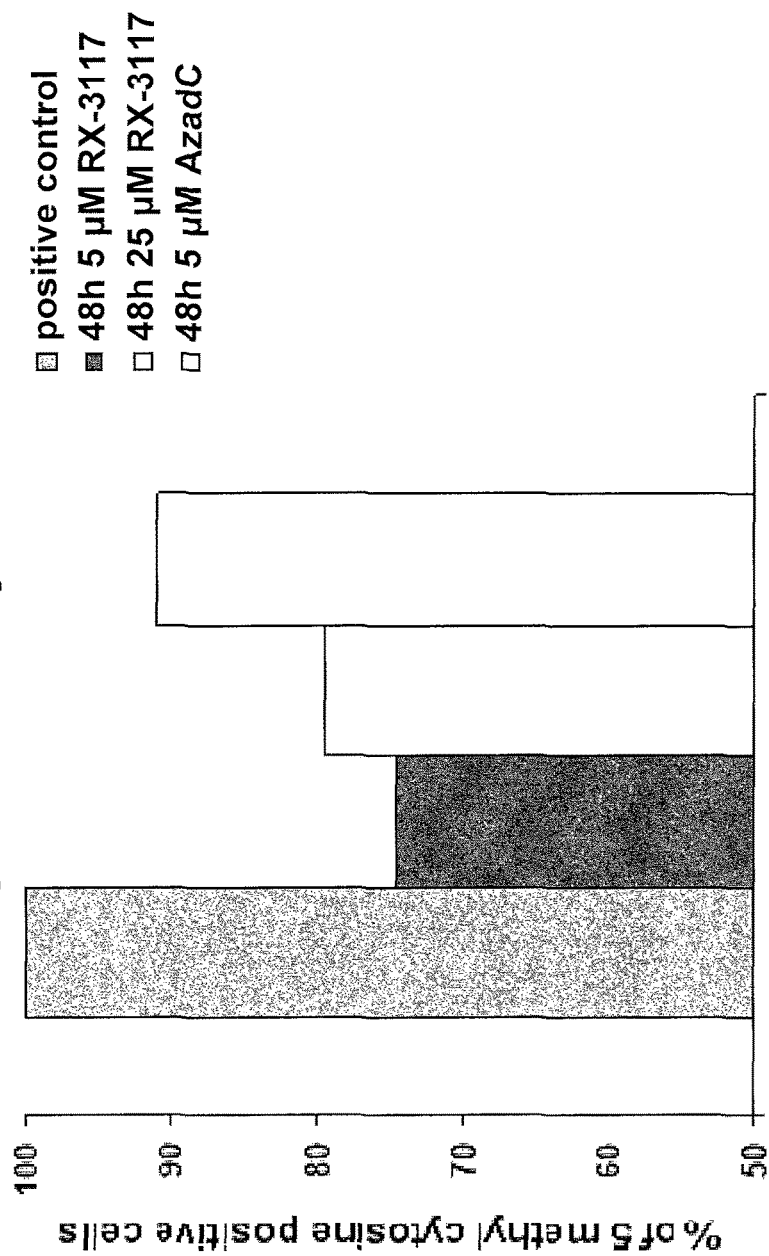
FIGS. 27A-27C shows the effects of RX-3711 and aza-dC on A549 cells. Global methylation was measured using FACS (FIG. 27A) or immunofluorescence (FIG. 27B) with an antibody against 5-methyl-cytosine. Control cells were set at 100% (FIG. 27A). The western blots (FIG. 27C) shows the expression of MGMT and E-cadherin in A549 cells, and p16 in SW1573 cells after exposure to RX-3117 and aza-dC.
Figure 27B:
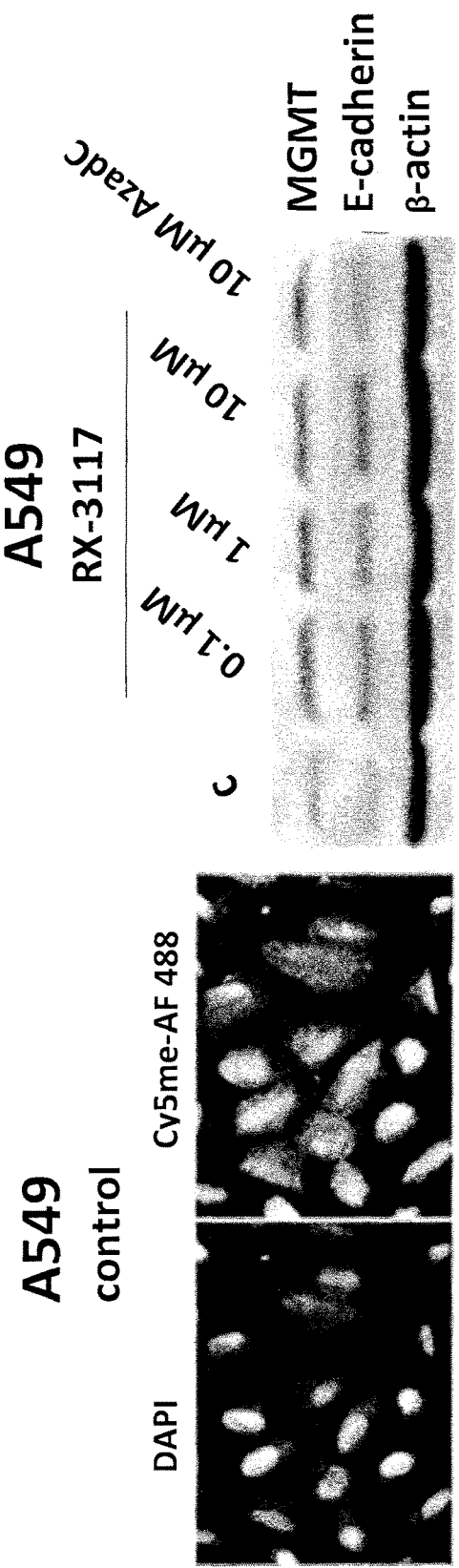
Figure 27C:
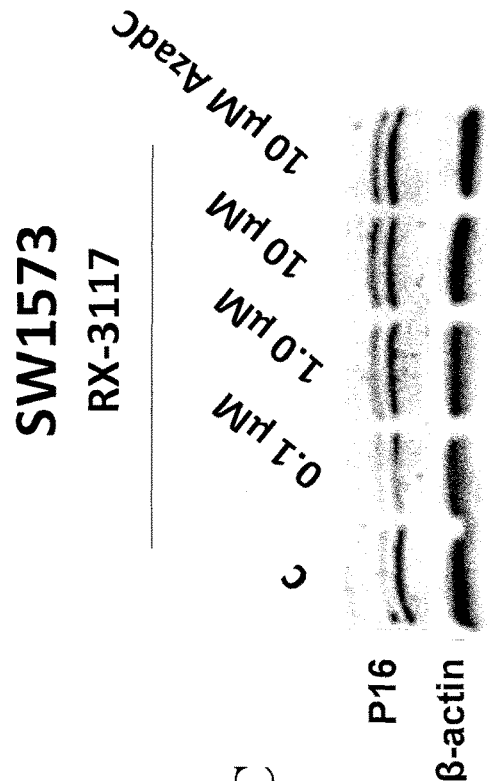

In A549 cells, 5 µM RX-3117 decreased overall methylation of DNA (detected by an antibody against 5-methylcytosine) by 25% after 48 hr exposure, while 5 µM DAC only inhibited 9% (FIG. 27A). For several genes known to be affected by methylation, protein expression and activity were evaluated. A549 cells were exposed to RX-3117 and measured using immunofluorescence with an antibody against 5-methyl-cytosine (FIG. 27B). In A549 and SW 1573 cells a 24 hr exposure to 5 µM RX-3117 increased the expression of the cell cycle protein p16INK4A and of the DNA repair enzyme MGMT. FIG. 27C shows the expression of MGMT, E-cadherin, and p16INK4 after exposure to RX-3117 and aza-dC.

Figure 28B:
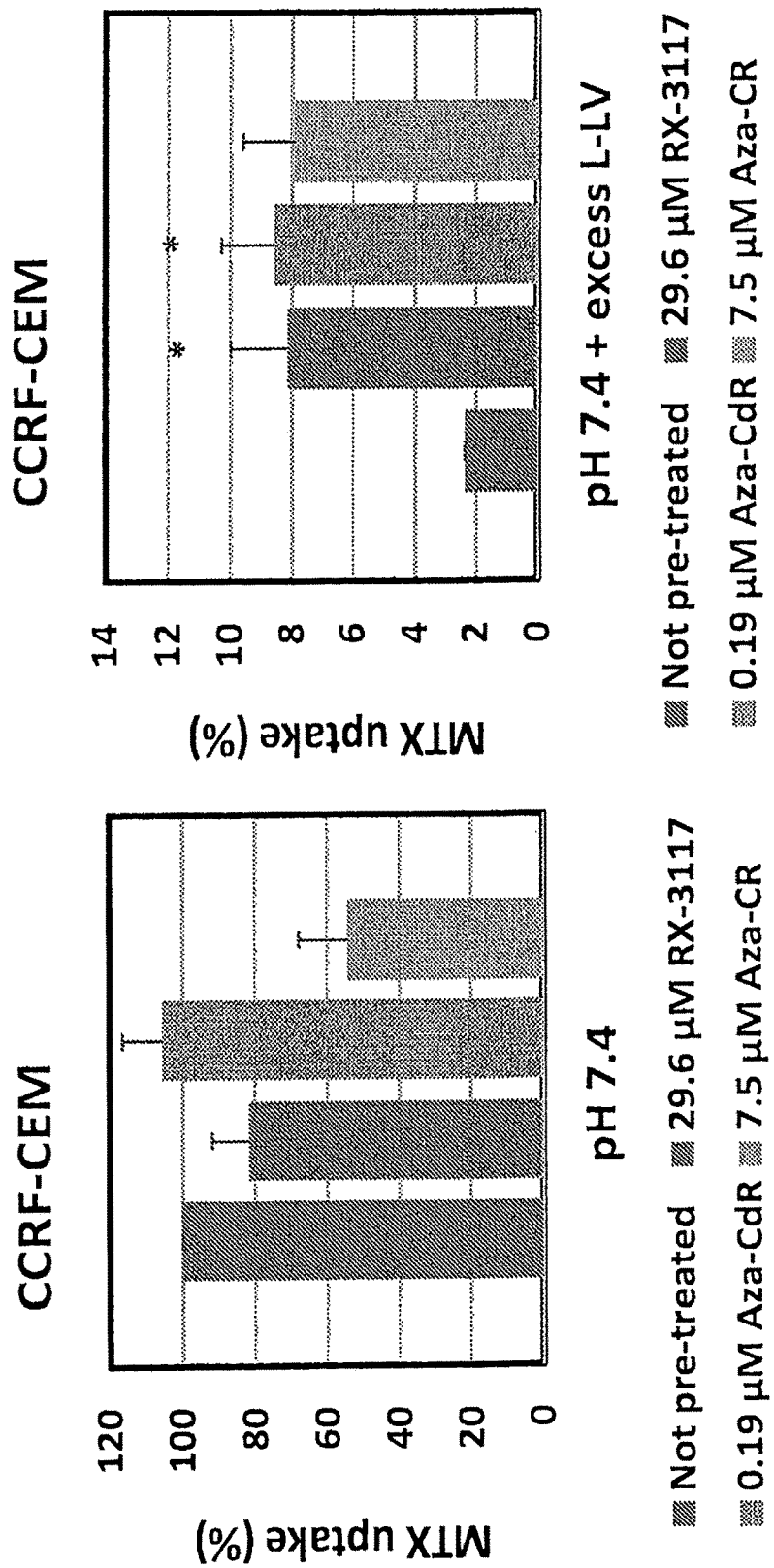
Figure 28C:
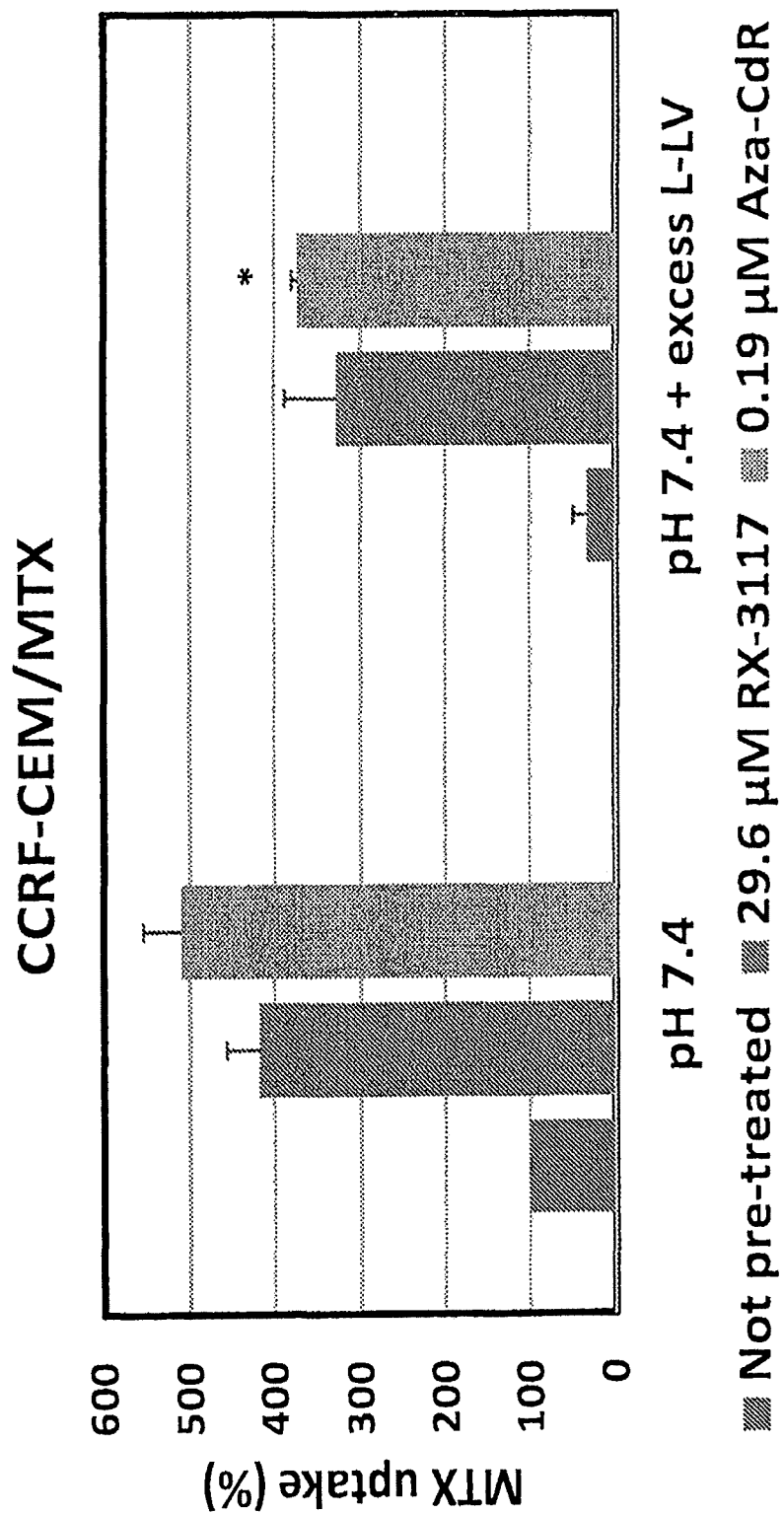

For PCFT, functional activity of RX-3117 was evaluated in CCRF-CEM leukemic cells which have a highly methylated PCFT promoter and in CEM-MTX cells which are deficient for the reduced folate carrier (RFC). PCFT is a specific folate transporter responsible for uptake of folic acid and the folate analogs methotrexate (MTX) and pemetrexed. Incubation of both CEM and CEM-MTX cells with either 29.6 µM RX-3117 or DAC as a positive control markedly increased PCFT mediated transport of MTX. This was more pronounced in CEM-MTX cells, 10-11-fold increase for both RX-3117 and DAC, compared to a 4-fold increase in CEM cells. Folic acid (FA) was added to inhibit PCFT and L-LV to inhibit RFC mediated MTX transport. Aza-CdR and Aza-CR were included as a positive control. (FIGS. 28 A, B and C).

Conclusion

In conclusion, RX-3117 downregulates DNMT1 protein and RNA expression by decreasing DNA methylation. RX-3117 mediated hypomethylation increases the expression of MGMT, E-cadherin, PCFT, and the tumor suppressor gene p16INK4A. PCFT mediated transport of MTX. These data underline DNMT1 inhibition as a novel mechanism of RX-3117. RX-3117 is a new epigenetic modulator.

Example 8: Evaluation of UCK2 Protein Expression as a Potential Predictive Biomarker of RX-3117

Background

A novel, orally bioavailable nucleoside analogue, RX-3117, is a prodrug activated intracellularly by Uridine Cytidine Kinase 2 (UCK2) that is thought to be expressed predominantly in tumor tissue. RX-3117 is currently being evaluated in a Phase Ib/IIa multi-center, open-label clinical study in patients with advanced pancreatic and bladder cancer. In this study, the relation between UCK2 tissue protein expression and the efficacy of RX-3117 in mice xenograft models and also UCK2 protein expression in a panel of human cancer tissues relative to normal tissue were studied.

Methods

The UCK2 protein expression in tumor tissues was analyzed by immunoblotting using clone 22-1 rabbit monoclonal antibody. The validated procedure for the immunohistochemistry (IHC) of UCK2 with clone 22-1 was performed in a panel of human formalin-fixed paraffin-embedded (FFPE) cancer and normal tissues.

Results

The immunoblotting protein level of UCK2 normalized to beta-actin and corresponding tumor growth inhibition (oral RX-3117 dose of 500 mg/kg, TIWK) were 57 and 67% in MiaPaCa2, 30 and −5% in BxPC3, 199 and 92% in Colo-205, 21 and 90% in Caki-1, 2 and 39% in A549, and 146 and 79% in H460, respectively. These data indicate an antitumor efficacy trend in a UCK2-dependent manner. The IHC of UCK2 showed that positive staining of UCK2 in cancer tissues was observed in 20/20 bladder cancer tissues (100% frequency), 19/20 CRC tissues (95% frequency), 18/20 NSCLC tissues (90% frequency), and 19/20 pancreatic cancer tissues (95% frequency). Average H-Scores of UCK2 in cancer tissues vs. normal tissues were 104 vs. 9 in lung, 97 vs. 20 in bladder, 67 vs. 41 in pancreas and 39 vs. 21 in colon, respectively.

Conclusions

The current data showed a correlation trend between UCK2 protein expression level and degree of antitumor activity of RX-3117 in xenograft models. It also supports a higher UCK2 protein expression level in human cancer tissues compared to their normal tissues. This suggests that RX-3117 activity may be specific to tumor tissue, and quantification of UCK2 expression in human cancer tissues may be useful as a predictive biomarker to select patients for their sensitivity to RX-3117 in future clinical studies.

Example 9: Synthesis of RX-3117 Monohydrate

Preparation of INT14 from ASM11 by Continuous Reaction of Stage 1 to 3 in Fixed Reactors ASM 11, tert-butyl(((3aR,4R,6aR)-5-fluoro-2,2-dimethyl-6-((trityloxy)methyl)-4,6a-dihydro-3aH-cyclopenta[d][1,3]dioxol-4-yl)oxy)diphenylsilane, (37.65 kg, 1 wt, 1 eq, 55 mol) was dissolved in 2-methyl tetrahydrofuran (4.0 vol, 3.4 wt). TBAF (tetra-n-butylammonium fluoride) 1.0 M in THF (tetrahydrofuran, (1.61 vol, 1.45 wt, 1.1 eq.) was added to the reaction vessel in one portion (mild exotherm addition controlled) over 15 to 45 min, maintaining 18 to 23° C. 2-Methyl tetrahydrofuran (1.0 vol, 0.9 wt) was charged to the vessel as a line rinse maintaining 18 to 23° C. and the resulting solution stirred at 18 to 23° C. for 6 hr until complete by $^1$H NMR. The reaction mixture was charged with 8% w/w sodium hydrogen carbonate (3.0 vol) and stirred at 18 to 23° C. for 5 to 10 min (caution: mild exotherm) and allowed the phases to separate and remove the lower aqueous phase (2×2.0 vol). The first 8% w/w sodium hydrogen carbonated extraction gave a milky aqueous layer and extended settle time did not clear the emulsion. Investigations showed the emulsion was confined to the aqueous layer and had a low organic content, thus the process was continued. The total separation of the first extraction was 5 hours 29 minutes. The second 8% w/w sodium hydrogen carbonate extraction separated without issue taking only 52 minutes. The aqueous phase was extracted with 2-methyl tetrahydrofuran (2.0 vol, 1.7 wt) and line was rinsed with 2-methyl tetrahydrofuran (2.0 vol, 1.7 wt). The combined organic phase that contained INT12 was heated to 40 to 50° C. and concentrated to ca. 4 vol at 40 to 50° C. under reduced pressure. Sampling was performed for analysis and analyzed by Karl-Fischer until water content was ≤0.2% w/w. The process yielded a 158.8 kg net weight of INT12 ASM11-alcohol in 2-methyltetrahydrofuran containing 15.3% w/w INT12 ASM11-alcohol, equating to a 99.0% total yield. A 92.83% area purity INT12 ASM11-alcohol ((3aS,4R,6aR)-5-fluoro-2,2-dimethyl-6-((trityloxy)methyl)-4,6a-dihydro-3aH-cyclopenta[d][1,3]dioxol-4-ol) was determined by HPLC analysis.

The INT12 solution was returned to the vessel, cooled to 0 to 5° C. and charged with triethylamine (0.41 vol, 0.30 wt, 2.0 eq). After rinsing the line with 2-methyltetrahydrofuran (1.0 vol, 0.9 wt), the solution was charged with methanesulphonyl chloride (0.17 vol, 0.25 wt, 1.5 eq) diluted in 2-methyl tetrahydrofuran (1.0 vol. 0.9 wt) (cautiously mix in the header vessel) maintaining 0 to 5° C. over at least 30 min (Exothermic). Additional 2-methyl tetrahydrofuran (0.5 vol, 0.4 wt) was added as a line rinse maintaining 0 to 5° C. The contents of the vessel were stirred at 0 to 5° C. until the reaction was complete by $^1$H NMR after 1 hour. The representative sample was removed after 1 hour and would have been checked approximately every 2 hours thereafter if necessary from the reaction vessel and analyzed to check the remaining INT12. After checking 100% conversion by $^1$H NMR analysis, water (4.0 vol) was charged maintaining 0 to 10° C. and the reaction mixture warmed to 18 to 23° C. and stirred for 5 to 10 min at 18 to 23° C. The upper organic phase in the vessel was separated and charged with 8% w/w sodium hydrogen carbonate solution (4.0 vol) maintaining 18 to 23° C. The resulting biphasic solution was stirred at 18 to 23° C. for 1 to 2 h and the separated organic phase charged with 20% w/w aqueous ammonium chloride (2.0 vol) and 2-methyl tetrahydrofuran (2.0 vol, 1.7 wt). As required, the temperature was adjusted to 18 to 23° C. The 20% w/w ammonium chloride wash resulted in a vigorous gas evolution, probably due to a reaction with residual sodium hydrogen carbonate from the previous step. After stirring at 18 to 23° C. for 5 to 10 min and the upper organic phase was separated and charged with purified water (2.0 vol) adjusted to 18 to 23° C. The separated organic phase that contained INT13 was concentrated under reduced pressure at 35 to 45° C. to ca. 2 vol. Sampling was performed for analysis. The process yielded a 78.4 kg net weight of INT13 ASM11-mesylate in 2-methyltetrahydrofuran containing 34.9% w/w INT13 ASM11-mesylate, equating to a 94.9% total yield. A 62.91% area purity INT13 ASM11-mesylate ((3aR,4R,6aR)-5-fluoro-2,2-dimethyl-6-((trityloxy)methyl)-4,6a-dihydro- 3aH-cyclopenta[d][1,3]dioxol-4-yl methanesulfonate) was determined by HPLC analysis, with 32.23% area TBDPS by-product present.

Continuously, the INT13 solution was charged with DMSO (3.8 vol, 4.2 wt) and heated to 40 to 45° C. to concentrate the organic phase at ≤45° C. under reduced pressure until no more solvent (2-methyltetrahydrofuran) distilled. The concentration was continued for 5 hours and 25 minutes and the IPC by $^1$H NMR showed a 2-methyltetrandrofuran content of 8.3% w/w. After cooling the solution to 27 to 33° C., cesium carbonate (1.2 wt) and cytosine (0.41 wt) were charged. The reaction mixture was heated to 33 to 37° C. and stirred until complete by HPLC. Sampling for N/O-alkylation ratio analysis was performed after 24 hours and at appropriate time points thereafter from the reaction vessel. After 33 hours and 47 minutes the reaction was deemed complete with an IPC result of 99.5% conversion. The ratio of the N- to O-isomers was at 99.03:0.97. On completion, the mixture was charged with isopropyl acetate (2.0 vol, 1.7 wt) and purified water (4.0 vol, 4.0 wt) maintaining ≤50° C. (water addition is exothermic). After stirring for 5 to 15 minutes the biphasic mixture was allowed to settle for 10 minutes and then separated the upper organic phase. The aqueous phase was re-extracted two times to recover all the product with isopropyl acetate (2.0 vol, 1.7 wt each) by stirring at 40 to 50° C. for 5 to 15 min and again allowing settling for 10 minutes before separating. The combined organic phase was cooled to 25 to 30° C. and charged with 10% v/v acetic acid (3.0 vol) and 26% w/w brine solution (1.0 vol) maintaining 25 to 30° C. and the biphasic solution was stirred at 25 to 30° C. for 30 to 60 min. The upper organic phase was washed three times with 10% v/v acetic acid (3.0 vol) and 26% w/w brine solution (1.0 vol) maintaining 25 to 30° C. In each wash step the upper organic solution was sampled by $^1$H NMR analysis. The organic phase was washed again with ca. 3% w/w brine solution (3×2.0 vol) at 25 to 30° C. and sampled for acetic acid content by $^1$H NMR. The organic phase that contained INT14 was heated to 35 to 45° C. and concentrated to ca. 5 vol at 35 to 45° C. under reduced pressure. The solution was charged with isopropyl acetate (3.0 vol, 2.6 wt) and concentrated to ca. 5 vol at 35 to 45° C. under reduced pressure. The solution was charged again with isopropyl acetate (5.0 vol, 4.4 wt), adjusted to 57 to 63° C., stirred at 57 to 63° C. for 1.5 to 3 h and checked by HPLC for crystallization/precipitation. The slurry was cooled to 35 to 45° C. and concentrated to ca. 5 vol at 35 to 45° C. under reduced pressure. The slurry was cooled further to 18 to 23° C. over 1.0 to 2.0 h and charged with n-heptane (7.0 vol, 4.8 wt) maintaining 18 to 23° C. over 30 to 90 min. After 1 to 2 h at 18 to 23° C. and 1 to 2 h at 0 to 5° C., the slurry was filtered through 20 µm cloth and washed with premixed n-heptane/isopropyl acetate (5:1, 2×1.0 vol) at 0 to 5° C. The product that contained INT14 was dried under vacuum at up to 55° C. and assayed by $^1$H NMR. Pass criteria was ≤2.0% w/w isopropyl acetate and ≤2.0% w/w n-heptane. The process yielded a 24.27 kg net weight of INT14, 4-amino-1-((3aS,4S,6aR)-5-fluoro-2,2-dimethyl-6-((trityloxy)methyl)-4,6a-dihydro-3aH-cyclopenta[d][1,3]dioxol-4-yl)pyrimidin-2(1H)-one, (45 mol, 93.25% purity), equivalent to 82% total and 64% w/w yield.

Preparation of RX-3117 Monohydrate from INT14 by Continuous Reaction of Stage 4 to 5 in Fixed Reactors INT14, 4-amino-1-((3aS,4S,6aR)-5-fluoro-2,2-dimethyl-6-((trityloxy)methyl)-4,6a-dihydro-3aH-cyclopenta[d][1,3]dioxol-4-yl)pyrimidin-2(1H)-one, (24.27 kg, 45 mol, 1.0 wt) was charged to a vessel followed by methanol (7.5 vol, 5.9 wt) and the temperature of the reaction mixture was adjusted to 18 to 23° C. To the reaction vessel, 2 M HCl (1.1 vol, 1.2 eq) was added maintaining temperature <50° C. The slurry mixture was heated to 45 to 55° C. and stirred at 45 to 55° C. (target 50° C.) for 2 to 2.5 h. The vessel volume was noted and the reaction mixture was distilled under reduced pressure maintaining 45 to 55° C. and maintaining constant volume by the addition of MeOH (5.0 vol, 4.0 wt). The mixture was sampled and continued to charge MeOH (2.5 vol 2.0 wt) maintaining constant volume by distillation at 45 to 50° C. until ≤1.0% area acetonide intermediate was present by HPLC. Once the conversion was completed, the reaction mixture was allowed to cool to 25 to 30° C. The reaction mixture was concentrated to 5 volumes under reduced pressure maintaining 35 to 45° C. The reaction mixture was cooled to 25 to 30° C. To the reaction vessel was charged with TBME (methyl tert-butyl ether) (5.0 vol, 3.7 wt) and water (5.0 vol) maintaining 25 to 30° C. The bi-phasic solution was stirred at 25 to 30° C. for 10 to 20 min and the phases were separated at 25 to 30° C. retaining the lower aqueous phase. The retained lower phase was transferred to the vessel and recharged with TBME (5.0 vol, 3.7 wt) maintaining 25 to 30° C. After stirring the biphasic solution at 25 to 30° C. for 10 to 20 min, the lower aqueous phase was separated. The lower aqueous phase was returned to the vessel and line was rinsed with water for injection (0.5 vol, 0.5 wt). The removal of trityl alcohol was checked by $^1$H NMR assay with 0.3% w/w/trityl alcohol content. If the assay result was not ≤0.5% w/w trityl alcohol, the aqueous phase was charged with TBME (5.0 vol, 3.7 wt) and stirred at 25 to 30° C. for 10 to 20 min then repeated the separation. The combined aqueous solution was adjusted to 18 to 23° C., charged with pre-treated Ambersep 900 (OH form) resin (⅝$^{ths}$ of the bulk treated material) and stirred for 15 min to check the pH. If the pH was <8.0, more Ambersep 900 resin (OH form) was added and stirred the solution for 30 to 45 min at 18 to 23° C. The slurry was filtered and washed with water for injection (2×4.0 vol) for 15 to 30 min per wash. The resin filter cake on the filter washed with water for injection (3×4.0 vol) further for 15 to 30 min per wash until a result of ≤1.0% was obtained by HPLC assay in each wash. The mother liquors and any wash obtained containing ≥1.0% were clarified via a 1 µm filter. The solution was heated to 40 to 45° C. and concentrated to 1.5 vol under reduced pressure at 40 to 45° C. After cooling the aqueous solution to 18 to 23° C. over 2 to 3 h and the mixture was aged for 60 min and charged with acetonitrile (9.5 vol) maintaining 18 to 23° C. at an approximately constant rate over 1.5 to 2 h. The slurry was aged at 18 to 23° C. for 2 h and cooled at 0 to 5° C. for 90 min. The solid was filtered through 20 µm cloth and washed with MeCN/water (5:1, 1.5 vol) and dried under an air atmosphere until MeCN content is <400 ppm by GC. The process yielded 8.20 kg (99.83% purity) net weight of RX-3117 monohydrate, 4-amino-1-((1S,4R,5S)-2-fluoro-4,5-dihydroxy-3-(hydroxymethyl)cyclopent-2-en-1-yl)pyrimidin-2(1H)-one 1H$_2$O, (29.8 mol, 99.83% purity), equivalent to 66% total and 34% w/w yield.

Figure 29:
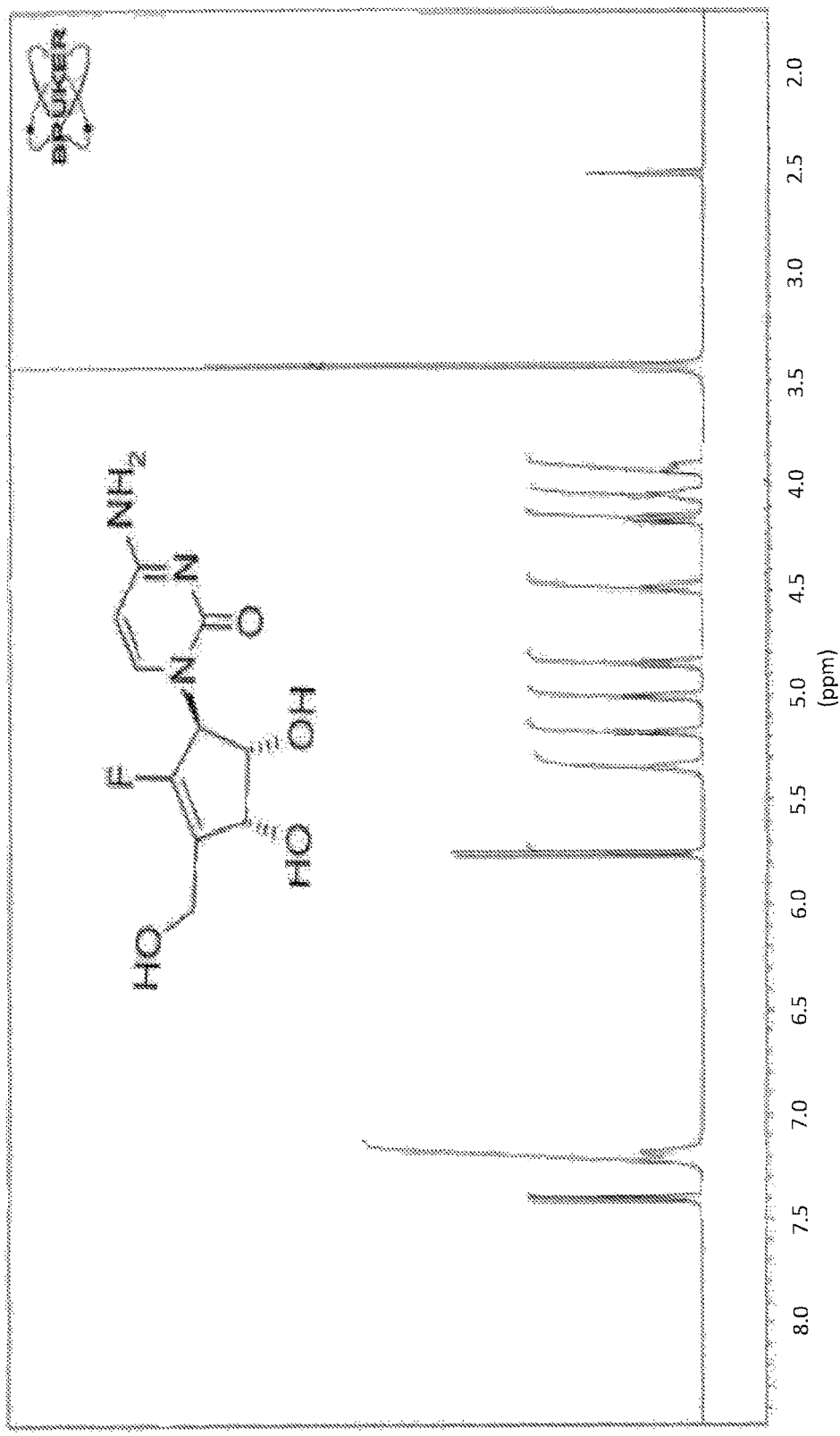
FIG. 29 is a $^1$H NMR of RX-3117 made using the process described in Example 9.

FIG. 29 is a $^1$H NMR showing RX-3117 made using the process described in Example 9. $^1$H-NMR (400 MHz, DMSOd$_6$), δ 7.40 ppm, (d, J=7.3 Hz, 1H) CH cytosine, δ 7.20 ppm, (broad d, J=9.1 Hz, 2H) NH$_2$, δ 5.74 ppm, (d, J=7.3 Hz, 1H) CH cytosine, δ 5.30 ppm, broad s, 1H, CH, δ 5.15 ppm, (d, J=7.1 Hz, 1H) (OH), δ 5.00 ppm, (d, J=6.1 Hz, 1H) (OH), δ 4.80 ppm, (q, J=5.3 Hz, 1H)(OH), δ 4.48 ppm, (q, J=5.3 Hz, 1H) CH, δ 4.17 ppm, (dd, J=9.1 Hz, 3.8 Hz, 1H) CH, δ 4.13 ppm, (dt, J=6.1 Hz, 5.8 Hz, 1H) CH, δ 3.91 ppm, (broad d, J=12.9 Hz, 2.8 Hz, 1H) CH.

Figure 30:
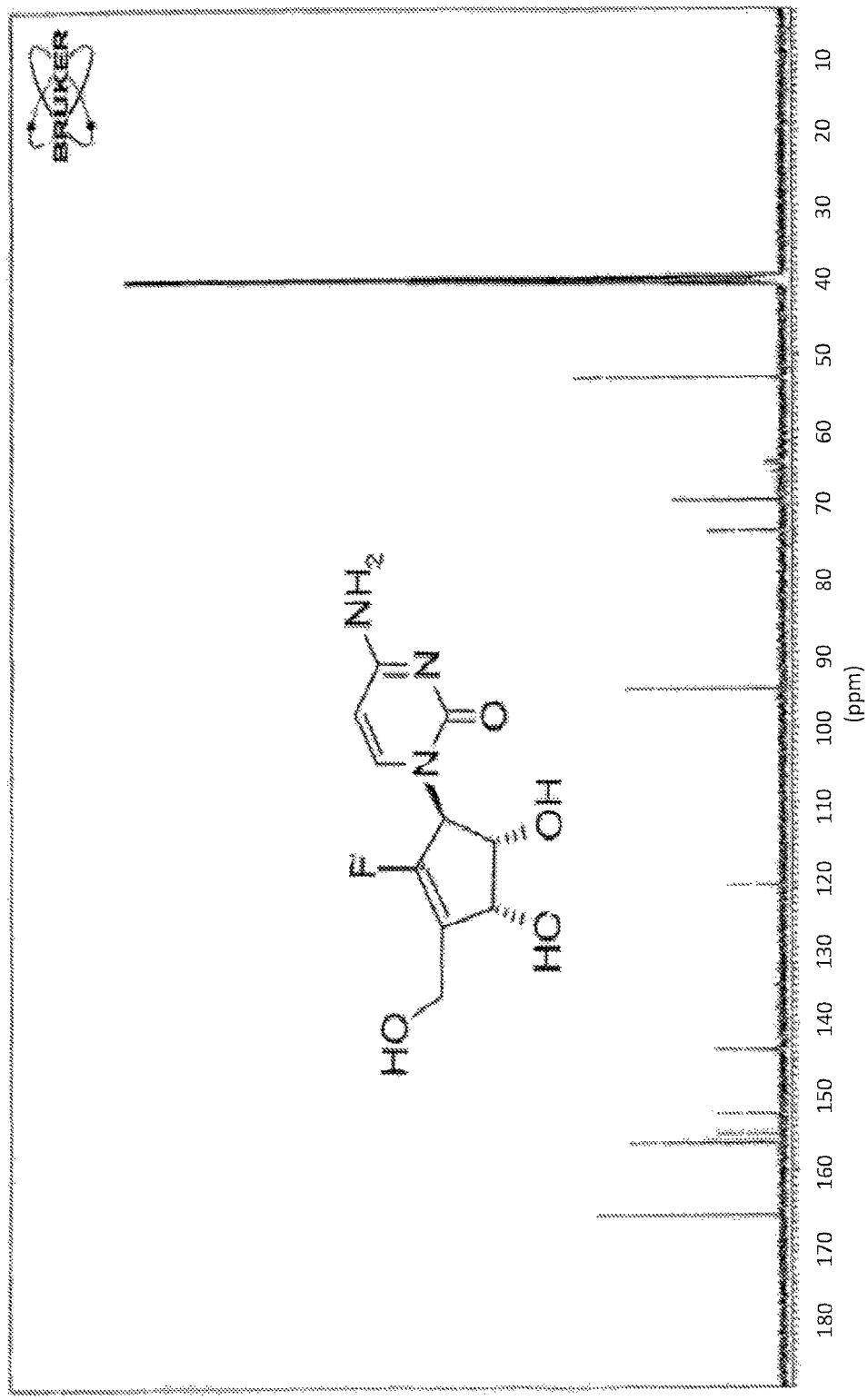
FIG. 30 is a $^{13}$C NMR of RX-3117 made using the process described in Example 9.

FIG. 30 is a $^{13}$C NMR of RX-3117 made using the process described in Example 9.

Figure 31:
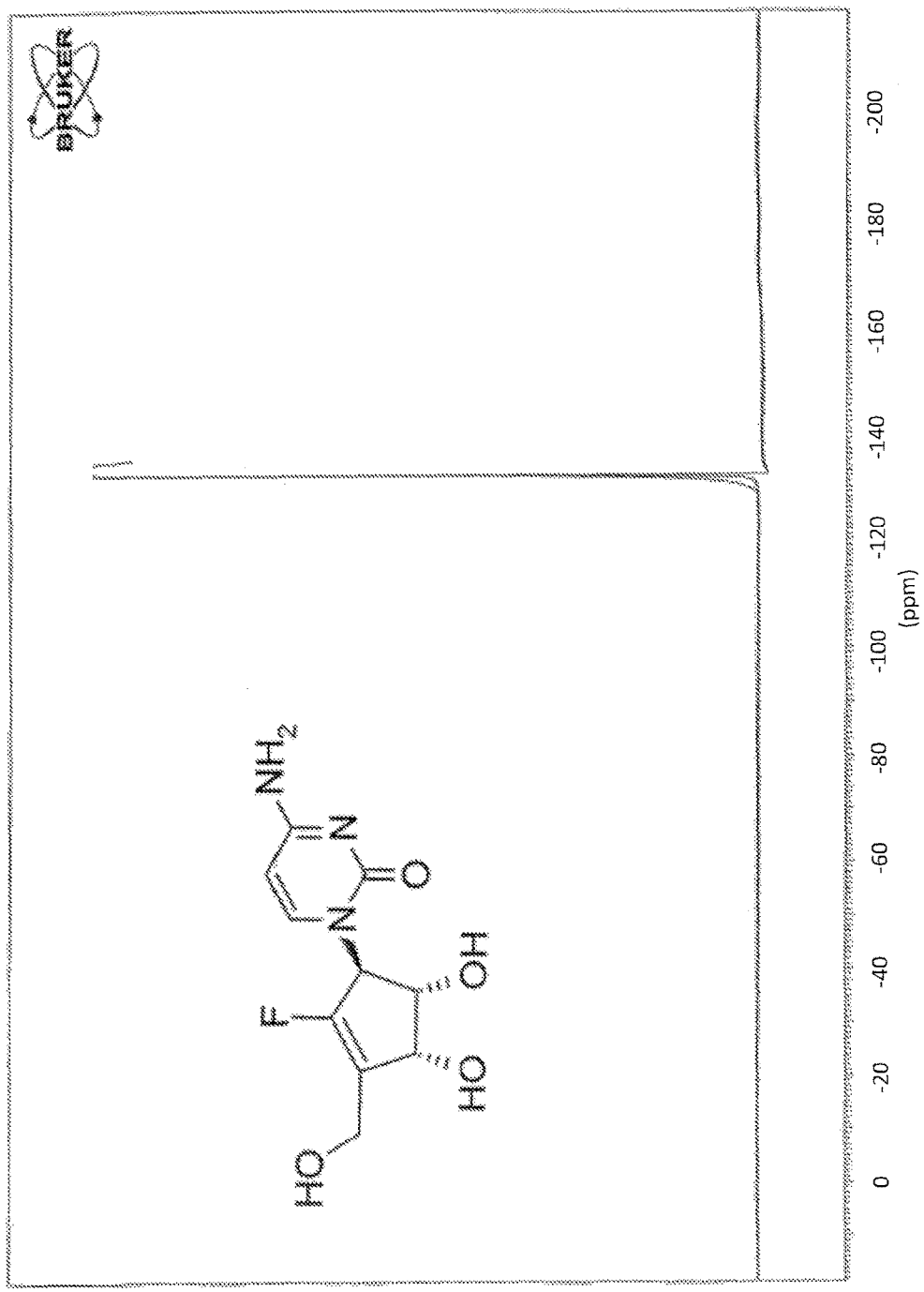
FIG. 31 is a $^{19}$F NMR of RX-3117 made using the process described in Example 9.

FIG. 31 is a $^{19}$F NMR of RX-3117 made using the process described in Example 9.

Figure 32:
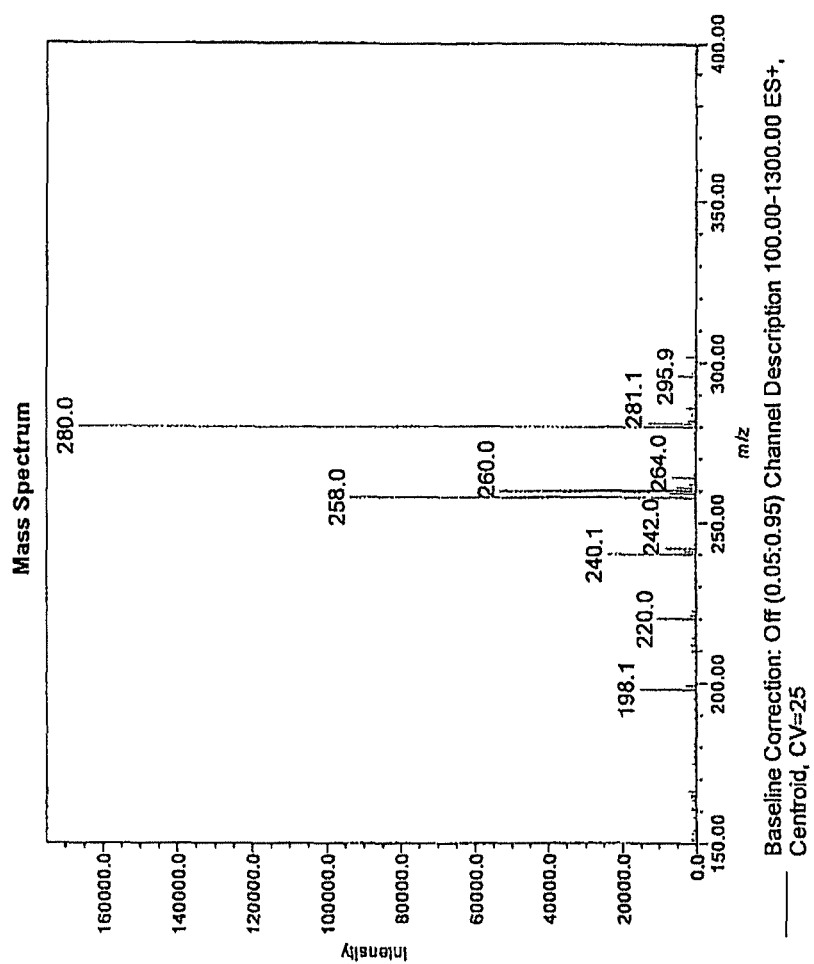
FIG. 32 is a Mass Spectrum of RX-3117 made using the process described in Example 9.

FIG. 32 is a Mass Spectrum of RX-3117 made using the process described in Example 9. The mass spectrum was done using the ES+ filter that shows the protonated species of RX-3117 (M+H) as well as an RX-3117 plus sodium adduct (M+Sodium) at m/z=280.0 (a common species seen during this analysis method). The sodium comes from the analysis method, not the manufacturing process.

Figure 33:
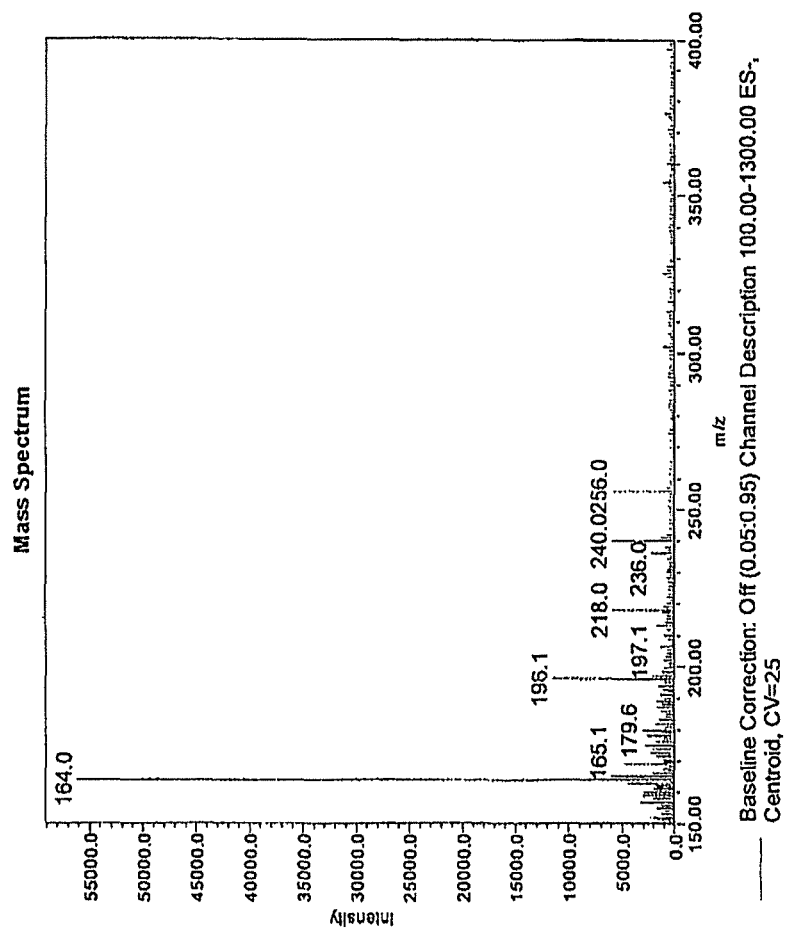
FIG. 33 is a Mass Spectrum (with an ES-filter) of RX-3117 made using the process described in Example 9.

FIG. 33 is a Mass Spectrum of RX-3117 made using the process described in Example 9. The mass spectrum was done using the ES-filter that shows the M-H species of RX-3117 during the analysis process. The ES- and ES+ filter methods together provide complete mass spectrum evidence for RX-3117.

Figure 34:
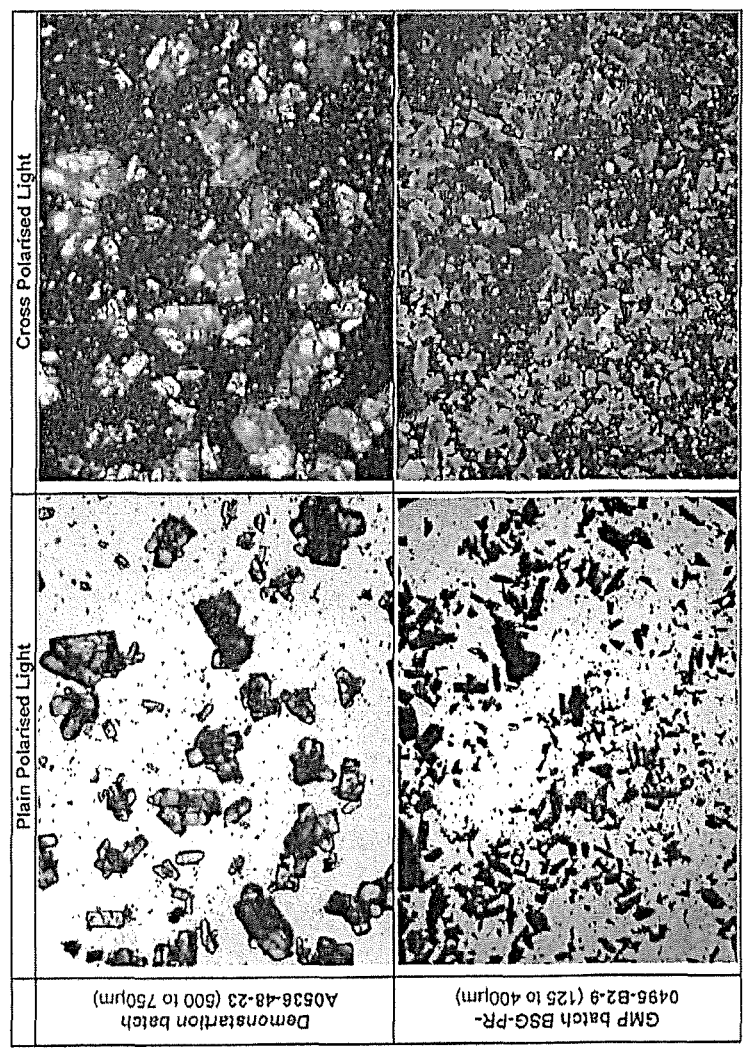
FIG. 34 is a microscopic comparison of RX-3117 made according to the process of Example 9 (Top row) and prepared using a laboratory scale process (bottom row) under plain polarized light (left column) and cross polarized light (right column.
Figure 35:
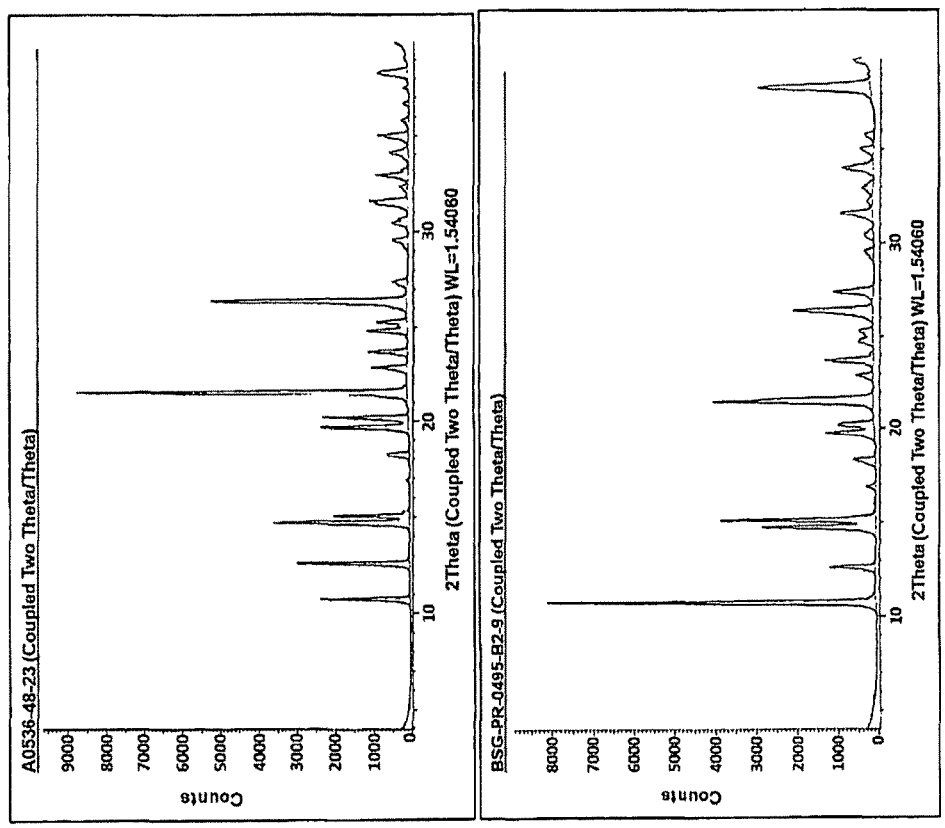
FIG. 35 is an X-Ray Powder Diffraction data comparing RX-3117 made using a laboratory scale process (top spectrum) and RX-3117 made using the process described in Example 9 (bottom spectrum).

In order to verify crystalline properties of material prepared according to the large scale synthetic process above, a microscopic comparison and was made to crystals prepared by a laboratory scale high purity process, as well as a comparison of the X-Ray Powder Diffraction patterns. FIG. 34 is a microscopic comparison of RX-3117 made according to the process of Example 9 (Top row) and prepared using a laboratory scale process (bottom row) under plain polarized light (left column) and cross polarised light (right column). FIG. 35 is an X-Ray Powder Diffraction data comparing RX-3117 made using a laboratory scale (top spectrum) and RX-3117 made using the process described in Example 9 (bottom spectrum). As can be seen, there is no significant difference in the crystal structures.

It will be apparent to those skilled in the art that specific embodiments of the disclosed subject matter may be directed to one or more of the above- and below-indicated embodiments in any combination.

While the invention has been disclosed in some detail by way of illustration and example, it is apparent to those skilled in the art that changes may be made and equivalents may be substituted without departing from the true spirit and scope of the invention. Therefore, the description and examples should not be construed as limiting the scope of the invention.

All references, publications, patents, and patent applications disclosed herein are hereby incorporated by reference in their entirety.

The invention claimed is:

1. A method of treating a human subject in need thereof with a compound of formula (I)

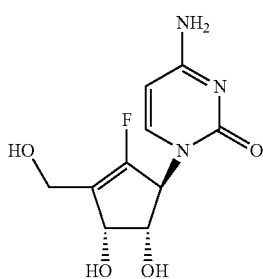

or a hydrate, a solvate, or a pharmaceutically acceptable salt thereof, comprising the steps of:
  collecting a sample of tumor cell or tissue from the subject;
  (ii) measuring the level of UCK2 expression in the tumor cell or tissue; and
  (iii) administering to the subject the compound of formula (I) at a dosage of about 300-1,000 mg/day, if an increased expression of UCK2 is measured in the tumor cell or tissue.

2. The method of claim 1, wherein the increased expression level is determined when the amount of UCK2 expression is greater than a predetermined level of UCK2 in a non-tumor cell.

3. The method of claim 2, wherein the non-tumor cell is a non-tumor cell of the subject.

4. The method of claim 1, wherein the increase in the expression level is by 5% or more.

5. The method of claim 1, wherein the tumor cell is ovarian cancer; metastatic breast cancer; adenocarcinoma of the pancreas; gastrointestinal cancer such as colorectal adenocarcinoma or cancer of the esophagus, stomach, pancreas, small bowel, hepatobiliary tract, colon, rectum or anus; bladder cancer such as metastatic bladder cancer, muscle invasive bladder cancer or non-muscle invasive bladder cancer; cervical cancer; lung cancer; non-small cell lung cancer; or renal cell carcinoma.

6. The method of claim 1, wherein the tumor cell is a lung cancer cell.

7. The method of claim 1, wherein the tumor cell is a non-small cell lung cancer cell.

8. A method of treating a human subject in need thereof with a compound of formula (I)

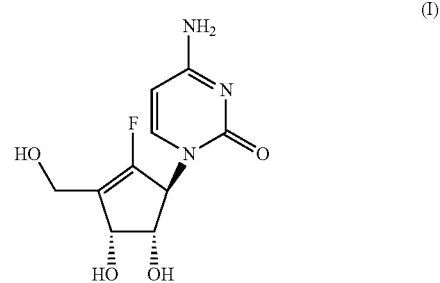

or a hydrate, a solvate, or a pharmaceutically acceptable salt thereof, comprising the steps of:
  (i) collecting a sample of tumor cell or tissue from the subject;
  (ii) measuring one of a protein kinase or p53 expression level in the sample;
  (iii) contacting the tumor cell or tissue with a compound of formula (I);
  (iv) measuring one of protein kinase or p53 expression level in the tumor cell or tissue after said contacting with the compound of formula (I); and
  (v) administering to the subject the compound of formula (I) at a dosage of about 300-1,000 mg/day, if an increase in protein kinase or p53 expression level is detected.

9. The method of claim 8, wherein said contacting the tumor cell or tissue with a compound of formula (I) by comprises administering the compound of formula (I) to the subject.

10. The method of claim 8, wherein said measuring protein kinase or p53 expression level in the tumor cell or tissue after contacting with the compound of formula (I) comprises collecting a second sample of tumor cell or tissue from the subject and measuring one of a protein kinase or p53 expression level in the second sample.

11. The method of claim 8, wherein the increase of protein kinase or p53 expression is by 5% or more.

12. The method of claim 8, further comprising the step of measuring protein Cdc25C or p-Cdc25C expression level in steps (ii) and (iv), wherein a decrease in protein Cdc25C or p-Cdc25C expression level indicates likelihood of efficacy.

13. The method of claim 12, wherein the decrease in protein Cdc25C or p-Cdc25C expression level is by 5% or more.

14. The method of claim 12, wherein the subject is administered the compound of formula (I) if the increase in protein kinase or p53 expression level and a decrease in the protein Cdc25C or p-Cdc25C expression level are detected.

15. The method of claim 8, wherein the protein kinase or p53 expression level is an expression level of a checkpoint kinase.

16. The method of claim 15, wherein the checkpoint kinase is Chk1 or Chk2.

17. The method of claim 8, wherein the protein kinase or p53 expression level is an expression level of p53.

\* \* \* \* \*